(12) United States Patent
Arai et al.

(10) Patent No.: US 9,867,811 B2
(45) Date of Patent: Jan. 16, 2018

(54) METHOD OF TREATING ATHEROSCLEROSIS IN HIGH TRIGLYCERIDE SUBJECTS

(75) Inventors: Yoshie Arai, Gifu (JP); Margaret Elizabeth Brousseau, Dracut, MA (US); Jessie Gu, Frammingham, MA (US); Tomoko Hayashi, Kanagawa (JP); Hironobu Mitani, Ibaraki Pref. (JP); Muneto Mogi, Waltham, MA (US); Kazuhiko Nonomura, Ibaraki Pref. (JP); Ken Yamada, Brookline, MA (US)

(73) Assignee: NOVARTIS AG, Basel (CH)

( * ) Notice: Subject to any disclaimer, the term of this patent is extended or adjusted under 35 U.S.C. 154(b) by 275 days.

(21) Appl. No.: 14/128,877

(22) PCT Filed: Jul. 6, 2012

(86) PCT No.: PCT/IB2012/053479
§ 371 (c)(1),
(2), (4) Date: Dec. 23, 2013

(87) PCT Pub. No.: WO2013/008164
PCT Pub. Date: Jan. 17, 2013

(65) Prior Publication Data
US 2014/0134262 A1 May 15, 2014

Related U.S. Application Data

(60) Provisional application No. 61/505,584, filed on Jul. 8, 2011, provisional application No. 61/657,061, filed on Jun. 8, 2012.

(51) Int. Cl.
| | |
|---|---|
| *A61K 31/421* | (2006.01) |
| *A61K 31/41* | (2006.01) |
| *A61K 31/44* | (2006.01) |
| *A61K 31/4439* | (2006.01) |
| *A61K 31/444* | (2006.01) |
| *A61K 31/4709* | (2006.01) |
| *A61K 31/506* | (2006.01) |
| *A61K 31/55* | (2006.01) |
| *A61K 31/505* | (2006.01) |
| *A61K 31/5377* | (2006.01) |
| *A61K 45/06* | (2006.01) |

(52) U.S. Cl.
CPC .......... *A61K 31/421* (2013.01); *A61K 31/41* (2013.01); *A61K 31/44* (2013.01); *A61K 31/444* (2013.01); *A61K 31/4439* (2013.01); *A61K 31/4709* (2013.01); *A61K 31/505* (2013.01); *A61K 31/506* (2013.01); *A61K 31/5377* (2013.01); *A61K 31/55* (2013.01); *A61K 45/06* (2013.01)

(58) Field of Classification Search
None
See application file for complete search history.

(56) References Cited

U.S. PATENT DOCUMENTS

2005/0059810 A1  3/2005  Kimiya et al.
2006/0063803 A1  3/2006  Ruggeri et al.
2007/0015758 A1  1/2007  Baruah et al.
2007/0213314 A1  9/2007  Chang et al.
2009/0023729 A1  1/2009  Nakamura et al.
2009/0029994 A1  1/2009  Nakamura et al.
(Continued)

FOREIGN PATENT DOCUMENTS

JP  2009-51827 A  3/2009
JP  2009-51828 A  3/2009
(Continued)

OTHER PUBLICATIONS

Oh et al., Management of Hypertriglyceridemia, 2007, American Family Physician, vol. 75, No. 9, pp. 1365-1371.*
Miller et al.:"Triglycerides and Cardiovascular Disease: A Scientific Statement From the American Heart Association", Circulation 2011; vol. 123, pp. 2292-2333.
Wolfe et al., 2004, "Cholesteryl ester transfer protein and coronary artery disease: An observation with therapeutic Implications", Circulation 110(11):1338-1340. XP002686456. ISSN: 0009-7322 DOI: 10.1161/01. CIR.0000143047.52724.BB See abstract and in particular p. 1339 right hand column. first paragraph.
Boekholdt et al., 2004, "Plasma levels of cholesteryl ester transfer protein and the risk of future coronary artery disease in apparently healthy men and women: the prospective EPIC (European Prospective Investigation into Cancer and nutrition)-Norfolk population study", CRC 1(11):1418-1423. XP002686457. PUBMED: 15337694. ISSN: 1524-4539 CETP inhibition may reduce the risk of cardiovascular events. but only in patient having increased TG levels (See abstract and p. 1422 right-hand column. conclusions).
(Continued)

*Primary Examiner* — Kortney L Klinkel
*Assistant Examiner* — Tori M Strong
(74) *Attorney, Agent, or Firm* — Sophie Binet Cross

(57) ABSTRACT

The present invention provides a compound of Formula I:

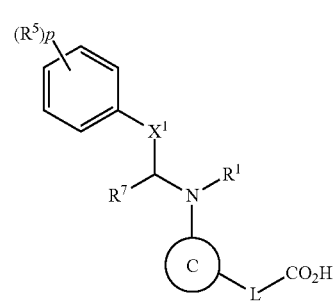

for use in the treatment, amelioration and/or prevention of diseases and conditions associated with CETP activity, such as atherosclerosis and dyslipidemia, in a subject with high triglyceride level; wherein $R^1$, $X^1$, $R^7$, $R^5$, C, L and p are defined herein. The present invention further provides a combination of pharmacologically active agents for use in the treatment, amelioration and/or prevention of diseases and conditions associated with CETP activity, such as atherosclerosis and dyslipidemia, in a subject with high triglyceride levels.

12 Claims, No Drawings

(56) References Cited

U.S. PATENT DOCUMENTS

| | | |
|---|---|---|
| 2009/0082352 A1 | 3/2009 | Tadaaki et al. |
| 2009/0118287 A1 | 5/2009 | Mogi et al. |

FOREIGN PATENT DOCUMENTS

| | | | |
|---|---|---|---|
| WO | 2002/088069 A2 | 11/2002 | |
| WO | 2005/097806 A1 | 10/2005 | |
| WO | 2006002342 | 1/2006 | |
| WO | 2006/014413 A1 | 2/2006 | |
| WO | 2006056854 | 6/2006 | |
| WO | 2007/079186 A2 | 7/2007 | |
| WO | 2007/081569 A2 | 7/2007 | |
| WO | 2007/081571 A2 | 7/2007 | |
| WO | 2007073934 | 7/2007 | |
| WO | 2007/092642 A2 | 8/2007 | |
| WO | 2007128568 | 11/2007 | |
| WO | 2007/145834 A2 | 12/2007 | |
| WO | 2008009435 | 1/2008 | |
| WO | 2008/099278 A2 | 8/2008 | |
| WO | 2009/027785 A2 | 3/2009 | |
| WO | 2009059943 | 5/2009 | |
| WO | WO 2009059943 A1 * | 5/2009 | ........... C07D 401/14 |
| WO | 2009071509 | 6/2009 | |
| WO | 2011002696 | 1/2011 | |

OTHER PUBLICATIONS

Borggreve et al., 2007, "High plasma cholesteryl ester transfer protein levels may favour reduced incidence of cardiovascular events in men with low triglycerides", European Heart Journal 28(8):1012-1018. XP002686458. Apr. 2007 LNKDPUBMED: 17409111. ISSN: 0195-668X CETP concentration is predictive of cardiovascular diseases only in patients having high plasma TG (see abstract and p. 1013. right hand column).

Wolfe M L et al: "Cholesteryl ester transfer protein and coronary artery disease: An observation with therapeutic implications", Circulation Sep. 14, 2004 US LNKD-DOI: 10.1161.CIR.0000143047. 52744.BB, vol. 110, No. 11, Sep. 14, 2004 (Sep. 14, 2004), pp. 1338-1340, ISSN: 0009-7322.

Boekholdt S Matthijs et al: Plasma levels of cholesteryl ester transfer protein and the risk of future coronary artery disease in apparently healthy men and women: the prospective EPIC (European Prospective Investigation into Cancer and nutrition)-Norfolk population study., Circulation Sep. 14, 2004 LNKD-PUBMED:15337694, vol. 110, No. 11, Sep. 14, 2004 (Sep. 14, 2004), pp. 1418-1423.

Borggreve Susanna E et al: "High plasma cholesteryl ester transfer protein levels may favour reduced incidence of cardiovascular events in men with low triglycerides", European Heart Journal Apr. 2007 LNKD-PUBMED:17409111, vol. 28, No. 8, Apr. 2007 (Apr. 2007), pp. 1012-1018.

Cannon C et al.: "Design of the Define trial: Determining the EFficacy and Tolerability of CETP INhibition with AnacEtrapib", American Heart Journal, vol. 158, Issue 4, Oct. 2009, pp. 513-519. e3.

The ACCORD Study Group: "Effects of Combination Lipid Therapy in Type 2 Diabetes Mellitus", The New England Journal of Medicine, Apr. 29, 2010, vol. 362, No. 17, pp. 1563-1574.

* cited by examiner

METHOD OF TREATING ATHEROSCLEROSIS IN HIGH TRIGLYCERIDE SUBJECTS

BACKGROUND OF THE INVENTION

This invention relates to method of use of inhibitors of cholesteryl ester transfer protein (CETP) in subjects with high triglyceride level, for raising certain plasma lipid levels, including high density lipoprotein (HDL)-cholesterol and for lowering other plasma lipid level, such as low density lipoprotein (LDL)-cholesterol and accordingly for the treating diseases which are affected by low levels of HDL cholesterol and/or high levels of LDL-cholesterol, such as atherosclerosis, dyslipidemia and cardiovascular diseases.

Atherosclerosis and its clinical consequences, coronary heart disease, is the leading cause of mortality in the industrialized world. It has long been recognized that variations in circulating lipoprotein profiles correlate with the risk of atherosclerosis and coronary heart disease. While elevated LDL-C may be the most recognized form of dislipidemina, low HDL-C is also a known risk factor for coronary heart disease.

Metabolic control of lipoprotein levels is a complex and dynamic process involving many factors. Among the many factors, one important metabolic control in man in the cholesteryl ester transfer protein (CETP).

CETP is a 74KD glycopeptide, it is secreted by the liver and is a key player in facilitating the transfer of lipids between the various lipoproteins in plasma. The primary function of CETP is to redistribute cholesteryl esters (CE) and triglycerides between lipoprotein particle, including high density lipoproteins (HDL), low density lipoprotein (LDL), very low density lipoprotein (VLDL), and chylomicrons. See Assmann, G et al., "HDL cholesterol and protective factors in atherosclerosis," *Circulation*, 109: 1118-1114 (2004). The net result of CETP activity is a lowering of HDL cholesterol and an increase in LDL cholesterol. This effect on lipoprotein profile has been shown to be pro-atherogenic, especially in subjects whose lipid profile constitutes an increased risk for coronary heart disease. Numerous epidemiologic studies correlating the effects of natural variation of CETP activity with respect to coronary heart disease risk have been performed (See Hirano, K. I. et al. (2000), "Pros and Cons of inhibiting cholesteryl ester transfer protein", *Curr. Opin. Lipidol.* 11(6), 589-596). These studies have clearly demonstrated an inverse correlation between plasma HDL-C concentration and CETP activity (see Inazu A., et al. (2000), "Cholesteryl ester transfer protein and atherosclerosis", *Curr. Opin. Lipidol.* 11(4), 389-396), leading to the hypothesis that pharmacologic inhibition of CETP lipid transfer activity is beneficial to humans in increasing levels of HDL-C while lowering those of LDL.

Anacetrapib, a CETP inhibitor developed by Merck, is currently in Phase III clinical development for the treatment of dyslipidemia and coronary heart disease. In vitro data indicate that anacetrapib does not retain its potency of CETP inhibition in plasma obtained from subjects with elevated triglyceride levels. This may translate into reduced efficacy of anacetrapib in patients with high triglycerides, whom constitute a significant portion of dyslipidemic subjects. Overall, 31% of the adult US population has an elevated plasma triglyceride concentration (≥150 mg/dL) (Carroll MD. Trends in serum lipids and lipoproteins of adults, 1960-2002. Journal of the American Medical Association 2005; 294:1773-81). High (≥200 mg/dL) and very high (≥500 mg/dL) fasting triglyceride levels are found in 16.2% and 1.1% of adults, respectively. Therefore, there is a clear need for improved therapy for the treatment and prevention of diseases and conditions related to CETP activity in a patient with high plasma triglycerides. To date, Merck has not provided any information on the efficacy of Anacetrapib in patients stratified by plasma triglyceride concentration.

SUMMARY OF THE INVENTION

The aim of the present invention is to provide a method of treating, preventing or ameliorating atherosclerosis or dyslipidemia, or a method of raising HDL-C and/or lowering LDL-C, in a subject with high triglycerides level comprising, administering to the subject a therapeutically effective amount of a compound of the following formula I:

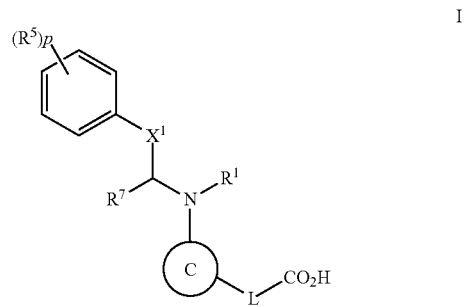

or a pharmaceutically acceptable salt thereof wherein:
C is a core structure selected from:

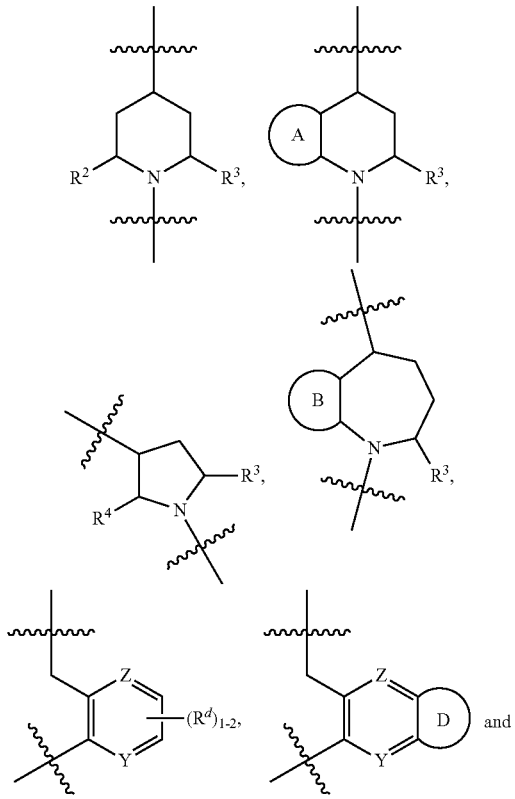

-continued

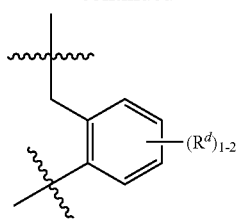
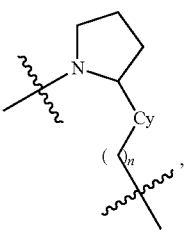
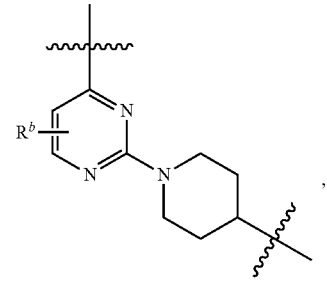

Y and Z are independently CH or N;

Rings A and B are independently phenyl or 5- or 6-membered heteroaryl wherein phenyl and hereroaryl are optionally substituted with 1 to 3 substituents independently selected from $C_{1-7}$alkyl, $C_{1-7}$alkoxy, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

D is $C_{3-7}$cycloalkyl, phenyl, 5- or 6-membered heteroaryl wherein phenyl and hereroaryl are optionally substituted with 1-3 substituents independently selected from 1 to 3 substituents independently selected from $C_{1-7}$alkyl, $C_{1-7}$alkoxy, CN, NO$_2$, $C_{3-7}$cycloalkyl-$C_{1-7}$alkyl, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

L is a linker selected from $C_{1-7}$alkyl (straight or branched) or a linker selected from:

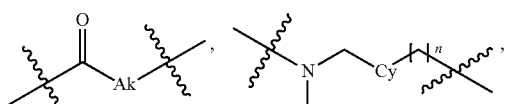
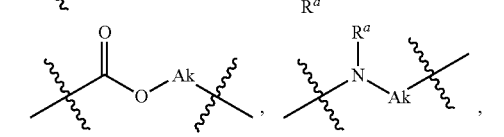
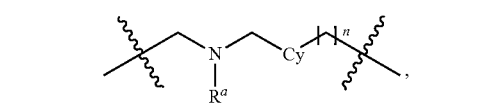
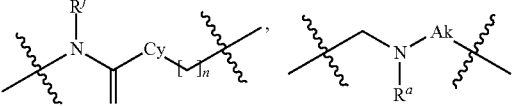
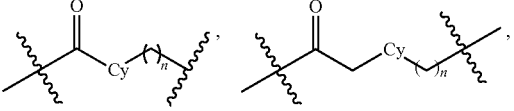
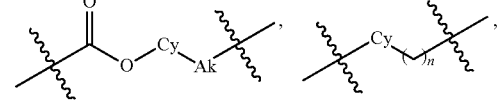

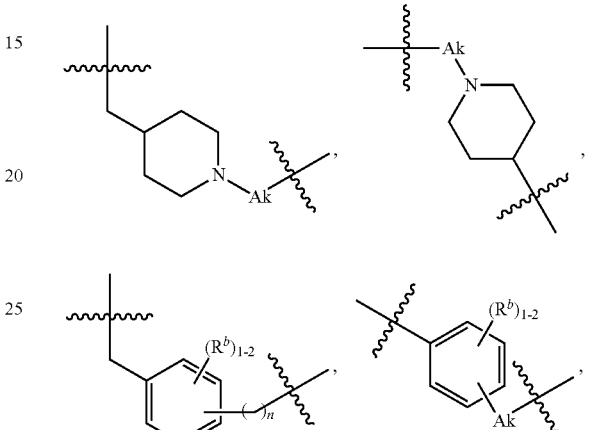
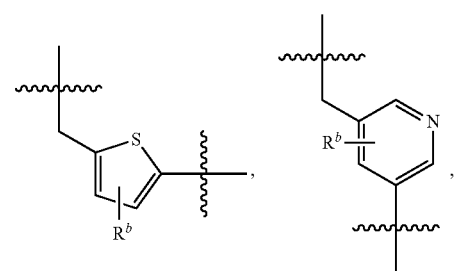
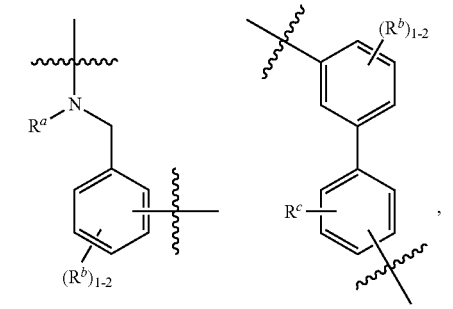
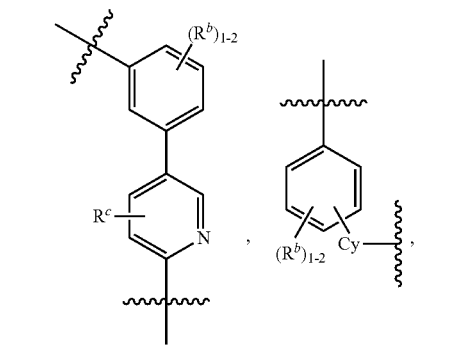

-continued

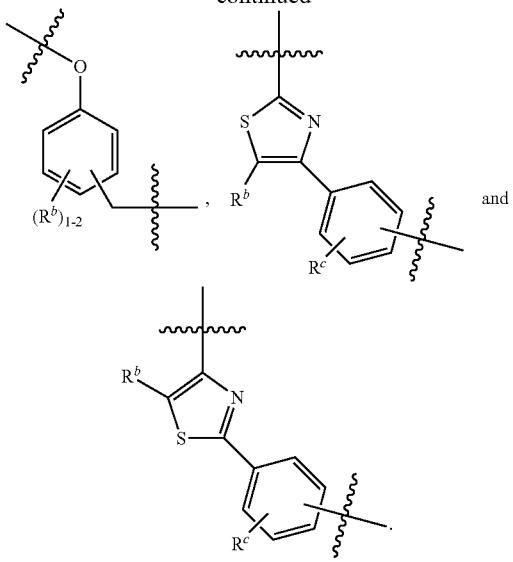

with the proviso that core C and L do not form a N—N bond or a N—O bond;

$X^1$ is absent or is $CR^6$ wherein $R^6$ forms with $R^1$ the following ring:

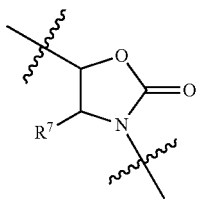

$R^1$ is C(O)O-alkyl, C(O)-alkyl or 5- or 6-membered heteroaryl optionally substituted with 1 to 3 substituents independently selected from $C_{1-7}$alkyl, hydroxy-$C_{1-7}$alkyl, $C_{1-7}$alkoxy optionally substituted with $C_{1-7}$alkoxy, hydroxy, halo or —S(O)$_2C_{1-4}$alkyl, amino, $C_{1-7}$alkylamino, di-$C_{1-7}$alkylamino, amino-$C_{1-7}$alkyl, $C_{1-7}$alkylamino-$C_{1-7}$alkyl, di-$C_{1-7}$-alkylamino-$C_{1-7}$alkyl, (hydroxy$C_{1-7}$alkyl)amino, halo, benzyloxy, 5- or 6-membered heterocyclyl or 5- or 6-membered heteroaryl wherein each heteroaryl and heterocyclyl are optionally substituted with 1 to 3 substituents independently selected from oxo, $C_{1-7}$alkyl, $C_{1-7}$alkanoyl and hydroxy;

$R^5$ in each instance, is independently halo, halo-$C_{1-7}$alkyl, $NO_2$ or CN;

p is 0, 1 or 2;

n is 0, 1 or 2;

$R^2$, $R^3$ and $R^4$ are independently H, $C_{1-7}$alkyl, halo-$C_{1-7}$alkyl, $C_{1-7}$alkoxy-$C_{1-7}$alkyl or $C_{6-10}$aryl-$C_{1-7}$alkyl;

$R^7$ is H or $C_{1-7}$alkyl;

$R^a$ is H, $C_{1-7}$alkyl or $C_{3-7}$cycloalkyl, C(O)—$C_{1-7}$alkyl, C(O)O—$C_{1-7}$alkyl;

$R^b$, $R^c$ and $R^d$ are independently H, $C_{1-7}$alkyl, $C_{3-7}$cycloalkyl, CN, halo-$C_{1-7}$alkyl, $C_{1-7}$alkoxy, halo, halo-$C_{1-7}$alkoxy, $C_{3-7}$cycloalkyloxy, phenyl, 5- or 6-membered ring heteroaryl, or hydroxy;

$R^f$ is H, $C_{1-7}$alkyl or $C_{3-7}$cycloalkyl;

Ak is $C_{1-6}$ linear or branched alkyl;

Cy is $C_{3-7}$ cycloalkyl.

DETAILED DESCRIPTION OF THE INVENTION

Definition

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-7}$alkyl" refers to a hydrocarbon having from one to seven carbon atoms. The term "alkylene" refers to a divalent alkyl radical, wherein alkyl is as previously defined.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. More preferably, the polyhaloalkyl is $CF_3$. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-7}$alkyl" refers to a hydrocarbon having one to seven carbon atoms and being substituted by one or more halo groups.

As used herein, the term "hydroxyalkyl" is an alkyl as defined herein, substituted with hydroxy.

As used herein, the term "aminoalkyl" refers to an alkyl as defined herein, substituted with amino (—$NH_2$). Similarly, the term "alkylaminoalkyl" refers to an alkyl substituted with alkylamino (alkyl-NH—)

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "haloalkoxy" refers to an alkoxy as defined herein, that is substituted by one or more halo groups as defined herein. Preferably the haloalkoxy can be monohaloalkoxy, dihaloalkoxy or polyhaloalkoxy including perhaloalkoxy.

As used herein, the term "alkoxyalkyl" refers to an alkyl as defined herein, substituted with alkoxy as defined herein. The term "$C_{1-7}$alkoxy-$C_{1-7}$alkyl" refers to a hydrocarbon having one to seven carbon atoms, which hydrocarbon is substituted with an alkoxy having 1 to 7 carbon atoms.

As used herein, the term "hydroxyalkoxy" refers to an alkoxy as defined herein, substituted with hydroxy. The term "hydroxy $C_{1-7}$alkoxy" refers to an alkoxy having 1 to 7 carbon atoms, substituted with hydroxy.

As used herein, the term "amino" refers to —NH$_2$. The term "alkylamino" refers to alkyl-NH— and the term "dialkylamino" refers to (alkyl)$_2$N—; wherein alkyl is as defined therein.

As used herein, the term "cycloalkyl" refers to saturated or partially unsaturated monocyclic hydrocarbon group. The term "$C_{3-7}$ cycloakyl" refers to a saturated or partially unsaturated monocyclic hydrocarbon group containing 3-7 carbon atoms. Exemplary monocyclic hydrocarbon groups include cyclopropyl, cyclobutyl, cyclopentyl, cyclopentenyl, cyclohexyl and cyclohexenyl.

As used herein, the term "cycloalkylalkyl" refers to an alkyl as defined herein, substituted with a cycloalkyl. The term "$C_{3-7}$cycloalkyl $C_{1-7}$alkyl" refer to a hydrocarbon having 1 to 7 carbon atoms, substituted with a cycloalkyl having 3 to 7 carbon atoms in the ring.

As used herein, the term "cycloalkoxy" or "cycloalkyloxy" refer interchangeably to cycloalkyl-O—, wherein cycloalkyl is as defined herein.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "$C_{6-10}$ aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-CH$_2$CH$_2$—. The term "$C_{6-10}$aryl-$C_{1-7}$alkyl" refers to a hydrocarbon having one to seven carbon atoms, which hydrocarbon is substituted with an aryl having 6 to 10 carbon atoms.

As used herein, the term "benzyloxy" refers to benzyl-O—, wherein benzyl is phenylCH$_2$—.

As used herein, the term "alkanoyl" refers to alkyl-C (O)—, wherein alkyl is as defined herein.

The term "Heteroaryl" includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. Monocyclic heteroaryl includes 5- or 6-membered heteroaryl, containing 1 to 5 heteroatoms independently selected from O, N or S wherein S and N may be oxidized to various oxidation states. For bicyclic heteroaryl system, the system is fully aromatic (i.e. all rings are aromatic).

Typical monocyclic 5- or 6-membered heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl, pyrimidin-5-yl. The term "heteroaryl" also refers to a group in which a heteroaromatic ring is fused to one or more aryl rings, where the radical or point of attachment is on the heteroaromatic ring or on the fused aryl rings. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

As used herein, the term "heterocyclyl" or "heterocyclo" refers to an optionally substituted, saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "halogen" or "halo" includes fluoro, bromo, chloro and iodo. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In one embodiment the heteroatoms is selected from N, O and S.

$R_{1-2}$ means 1 or 2 R groups. Therefore, for example, $(R^b)_{1-2}$ represents 1 or 2 $R^b$ groups and similarly, $(R^d)_{1-2}$ represents 1 or 2 $R^d$.

Compounds for the Method of the Invention:

Various embodiments of the invention are described herein. It will be recognized that features specified in each embodiment may be combined with other specified features to provide further embodiments.

In embodiment 1, the invention pertains to a compound of the following formula I:

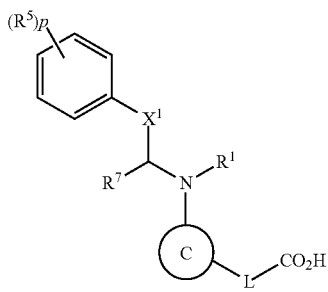

or a pharmaceutically acceptable salt thereof wherein:
C is a core structure selected from:

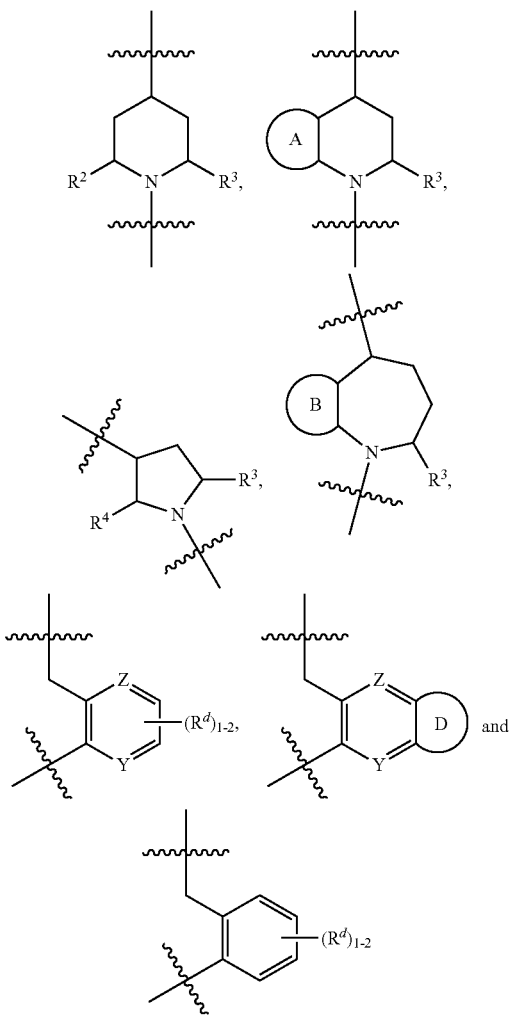

Y and Z are independently CH or N;
Rings A and B are independently phenyl or 5- or 6-membered heteroaryl wherein phenyl and hereroaryl are optionally substituted with 1 to 3 substituents independently selected from $C_{1-7}$alkyl, $C_{1-7}$alkoxy, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;
D is $C_{3-7}$cycloalkyl, phenyl, 5- or 6-membered heteroaryl wherein phenyl and hereroaryl are optionally substituted with 1-3 substituents independently selected from 1 to 3 substituents independently selected from $C_{1-7}$alkyl, $C_{1-7}$alkoxy, CN, $NO_2$, $C_{3-7}$cycloalkyl-$C_{1-7}$alkyl, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

L is a linker selected from $C_{1-7}$alkyl (straight or branched) or a linker selected from:

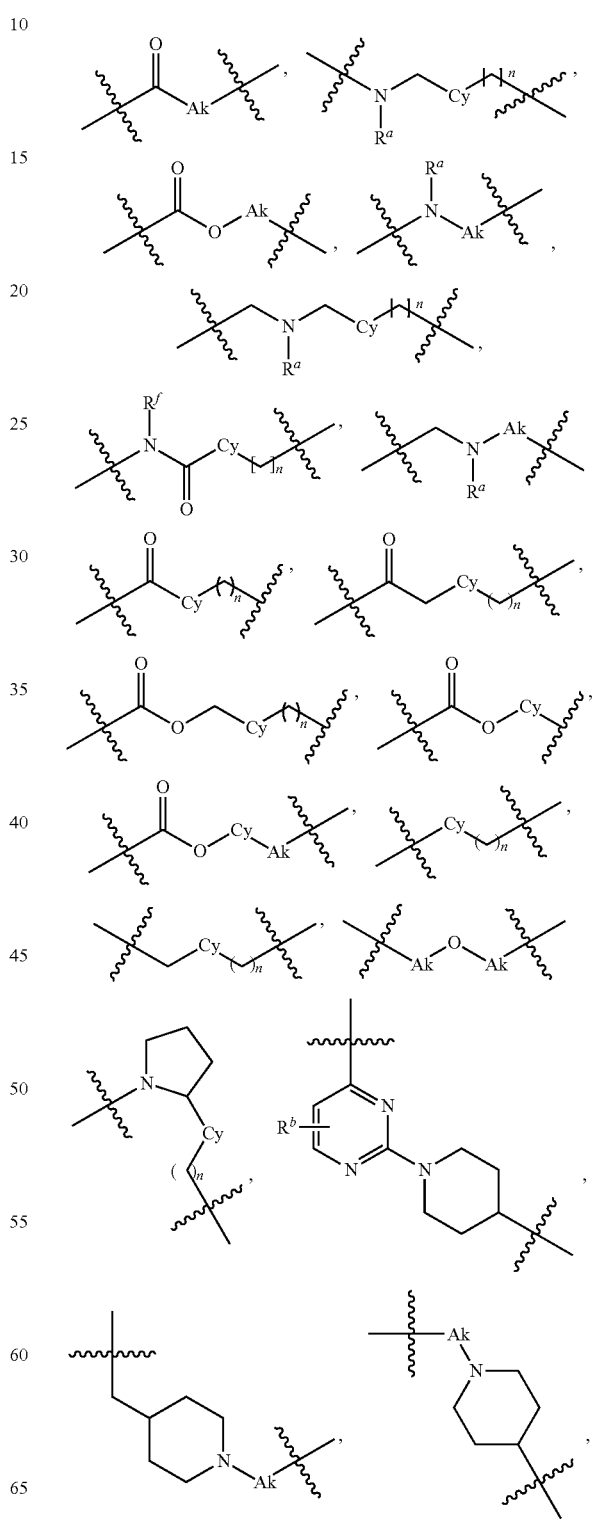

-continued

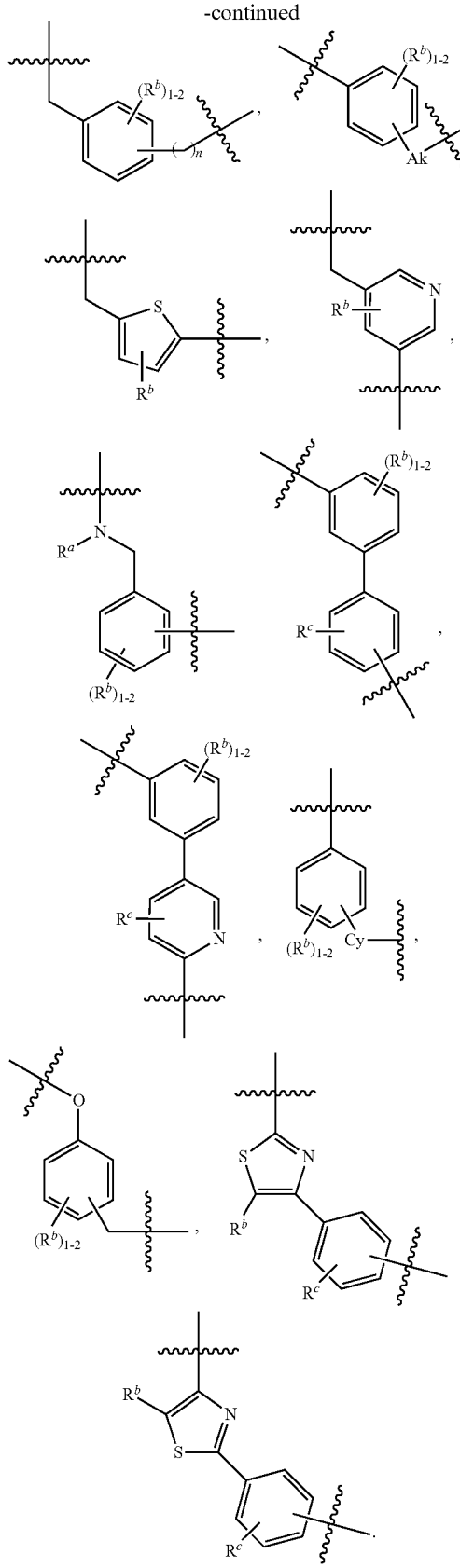

with the proviso that core C and L do not form a N—N bond or a N—O bond;

$X^1$ is absent or is $CR^6$ wherein $R^6$ forms with $R^1$ the following ring:

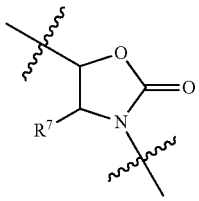

$R^1$ is C(O)O-alkyl, C(O)-alkyl or 5- or 6-membered heteroary optionally substituted with 1 to 3 substituents independently selected from $C_{1-7}$alkyl, hydroxy-$C_{1-7}$alkyl, $C_{1-7}$alkoxy, amino, $C_{1-7}$alkylamino, di-$C_{1-7}$alkylamino, amino-$C_{1-7}$alkyl, $C_{1-7}$alkylamino-$C_{1-7}$alkyl, di-$C_{1-7}$alkylamino-$C_{1-7}$alkyl, (hydroxy$C_{1-7}$alkyl)amino, hydroxy-$C_{1-7}$alkoxy, halo, benzyloxy, 5- or 6-membered heterocyclyl or 5- or 6-membered heteroaryl wherein each heteroaryl and heterocyclyl are optionally substituted with 1 to 3 substituents independently selected from oxo, $C_{1-7}$alkyl, $C_{1-7}$alkanoyl and hydroxy;

$R^5$ in each instance, is independently halo, halo-$C_{1-7}$alkyl, $NO_2$ or CN;

p is 0, 1 or 2;

n is 0, 1 or 2;

$R^2$, $R^3$ and $R^4$ are independently H, $C_{1-7}$alkyl, halo-$C_{1-7}$alkyl, $C_{1-7}$alkoxy-$C_{1-7}$alkyl or $C_{6-10}$aryl-$C_{1-7}$alkyl;

$R^7$ is H or $C_{1-7}$alkyl;

$R^a$ is H, $C_{1-7}$alkyl or $C_{3-7}$cycloalkyl, C(O)—$C_{1-7}$alkyl, C(O)O—$C_{1-7}$alkyl;

$R^b$, $R^c$ and $R^d$ are independently H, $C_{1-7}$alkyl, $C_{3-7}$cycloalkyl, CN, halo-$C_{1-7}$alkyl, $C_{1-7}$alkoxy, halo, halo-$C_{1-7}$alkoxy, $C_{3-7}$cycloalkyloxy, phenyl, 5- or 6-membered ring heteroaryl, or hydroxy;

$R^f$ is H, $C_{1-7}$alkyl or $C_{3-7}$cycloalkyl;

Ak is $C_{1-6}$ linear or branched alkyl;

Cy is $C_{3-7}$ cycloalkyl; for use in the treatment, prevention and/or amelioration of atherosclerosis or dyslipidemia, or for use in raising HDL-C and/or in lowering LDL-C, in a subject with high triglycerides level.

In embodiment 1A, the invention provides a method of treating, preventing or ameliorating atherosclerosis or dyslipidemia, or a method of raising HDL-C and/or lowering LDL-C, in a subject with high triglycerides level comprising, administering to the subject a therapeutically effective amount of a compound of the following formula I:

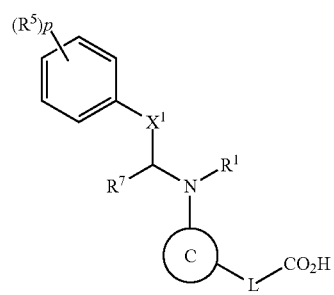

or a pharmaceutically acceptable salt thereof wherein:

C is a core structure selected from:

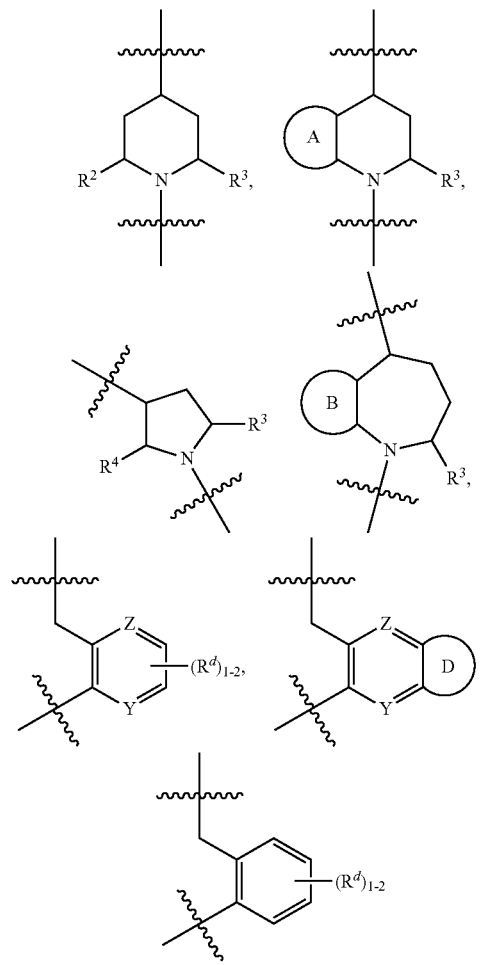

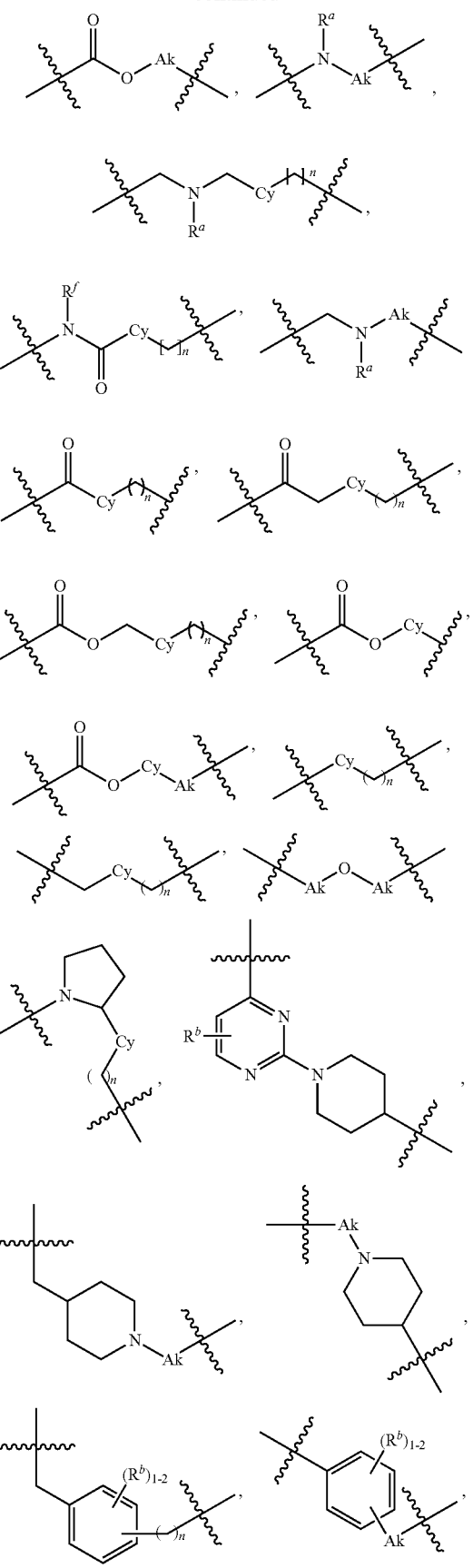

Y and Z are independently CH or N;

Rings A and B are independently phenyl or 5- or 6-membered heteroaryl wherein phenyl and hereroaryl are optionally substituted with 1 to 3 substituents independently selected from $C_{1-7}$alkyl, $C_{1-7}$alkoxy, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

D is $C_{3-7}$cycloalkyl, phenyl, 5- or 6-membered heteroaryl wherein phenyl and hereroaryl are optionally substituted with 1-3 substituents independently selected from 1 to 3 substituents independently selected from $C_{1-7}$alkyl, $C_{1-7}$alkoxy, CN, $NO_2$, $C_{3-7}$cycloalkyl-$C_{1-7}$alkyl, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

L is a linker selected from $C_{1-7}$alkyl (straight or branched) or a linker selected from:

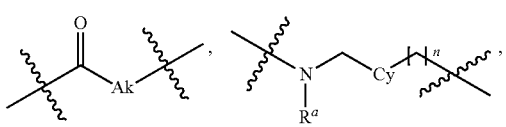

-continued

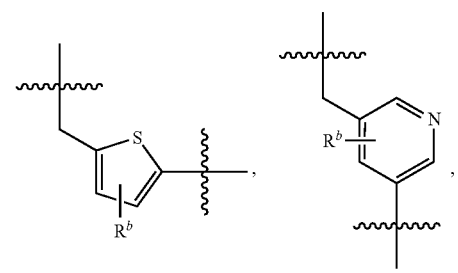

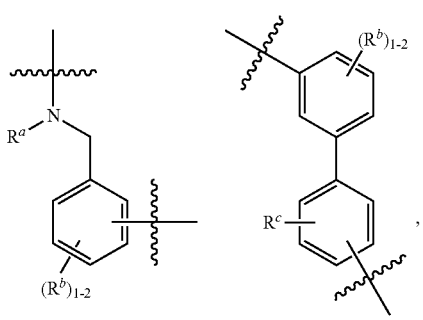

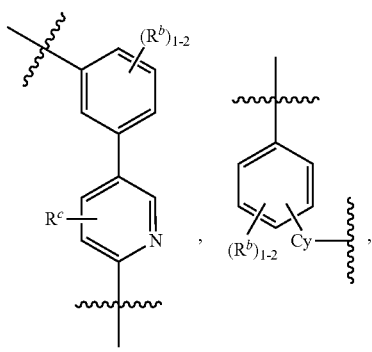

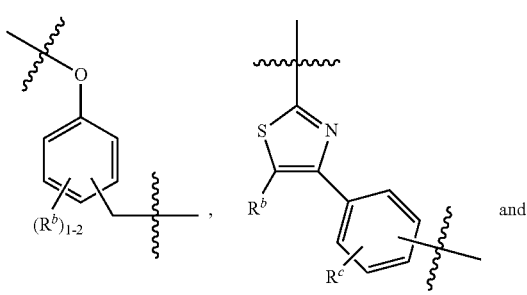

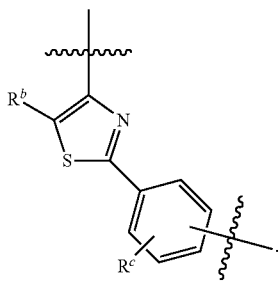

with the proviso that core C and L do not form a N—N bond or a N—O bond;

$X^1$ is absent or is $CR^6$ wherein $R^6$ forms with $R^1$ the following ring:

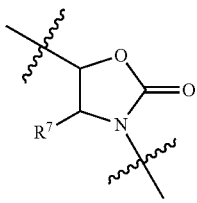

$R^1$ is C(O)O-alkyl, C(O)-alkyl or 5- or 6-membered heteroary optionally substituted with 1 to 3 substituents independently selected from $C_{1-7}$alkyl, hydroxy-$C_{1-7}$alkyl, $C_{1-7}$alkoxy, amino, $C_{1-7}$alkylamino, di-$C_{1-7}$alkylamino, amino-$C_{1-7}$alkyl, $C_{1-7}$alkylamino-$C_{1-7}$alkyl, di-$C_{1-7}$alkylamino-$C_{1-7}$alkyl, (hydroxy$C_{1-7}$alkyl)amino, hydroxy-$C_{1-7}$alkoxy, halo, benzyloxy, 5- or 6-membered heterocyclyl or 5- or 6-membered heteroaryl wherein each heteroaryl and heterocyclyl are optionally substituted with 1 to 3 substituents independently selected from oxo, $C_{1-7}$alkyl, $C_{1-7}$alkanoyl and hydroxy;

$R^5$ in each instance, is independently halo, halo-$C_{1-7}$alkyl, $NO_2$ or CN;

p is 0, 1 or 2;

n is 0, 1 or 2;

$R^2$, $R^3$ and $R^4$ are independently H, $C_{1-7}$alkyl, halo-$C_{1-7}$alkyl, $C_{1-7}$alkoxy-$C_{1-7}$alkyl or $C_{6-10}$aryl-$C_{1-7}$alkyl;

$R^7$ is H or $C_{1-7}$alkyl;

$R^a$ is H, $C_{1-7}$alkyl or $C_{3-7}$cycloalkyl, C(O)—$C_{1-7}$alkyl, C(O)O—$C_{1-7}$alkyl;

$R^b$, $R^c$ and $R^d$ are independently H, $C_{1-7}$alkyl, $C_{3-7}$cycloalkyl, CN, halo-$C_{1-7}$alkyl, $C_{1-7}$alkoxy, halo, halo-$C_{1-7}$alkoxy, $C_{3-7}$cycloalkyloxy, phenyl, 5- or 6-membered ring heteroaryl, or hydroxy;

$R^f$ is H, $C_{1-7}$alkyl or $C_{3-7}$cycloalkyl;

Ak is $C_{1-6}$ linear or branched alkyl;

Cy is $C_{3-7}$ cycloalkyl.

In embodiment 2, the invention provides a method of treating atherosclerosis or dyslipidemia, or a method of raising HDL-C and/or lowering LDL-C comprising:

1. Selecting subject with high triglycerides level; and

2. Administering to said subject a therapeutically effective amount of a compound of Formula I:

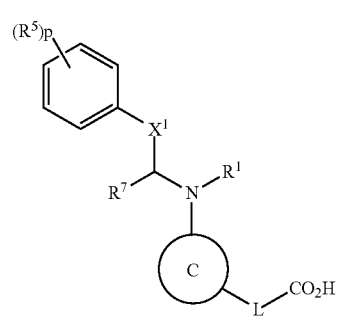

or a pharmaceutically acceptable salt thereof wherein:
C is a core structure selected from:

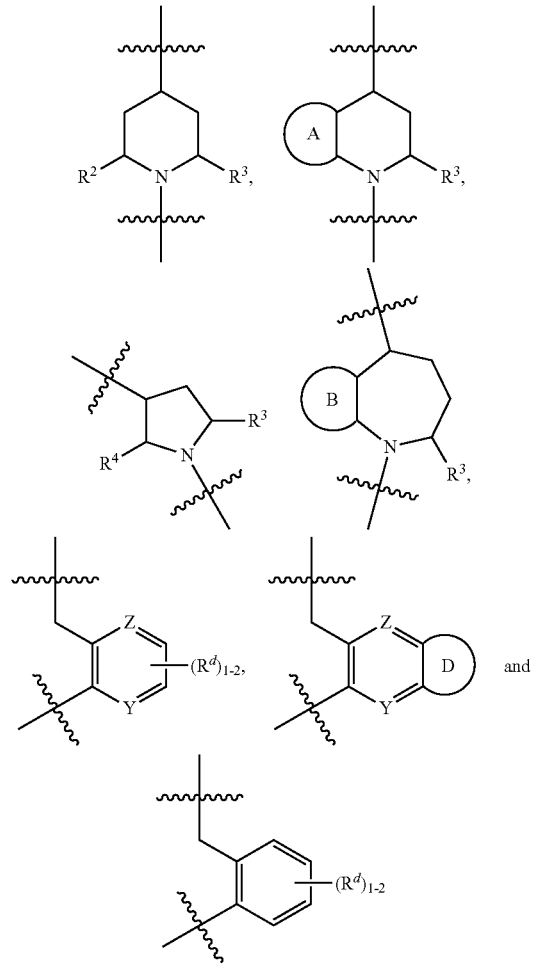

Y and Z are independently CH or N;

Rings A and B are independently phenyl or 5- or 6-membered heteroaryl wherein phenyl and hereroaryl are optionally substituted with 1 to 3 substituents independently selected from $C_{1-7}$alkyl, $C_{1-7}$alkoxy, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

D is $C_{3-7}$cycloalkyl, phenyl, 5- or 6-membered heteroaryl wherein phenyl and hereroaryl are optionally substituted with 1-3 substituents independently selected from 1 to 3 substituents independently selected from $C_{1-7}$alkyl, $C_{1-7}$alkoxy, CN, $NO_2$, $C_{3-7}$cycloalkyl-$C_{1-7}$alkyl, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;

L is a linker selected from $C_{1-7}$alkyl (straight or branched) or a linker selected from:

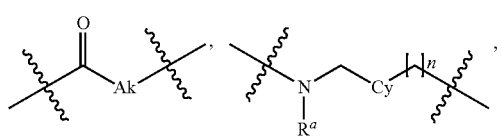

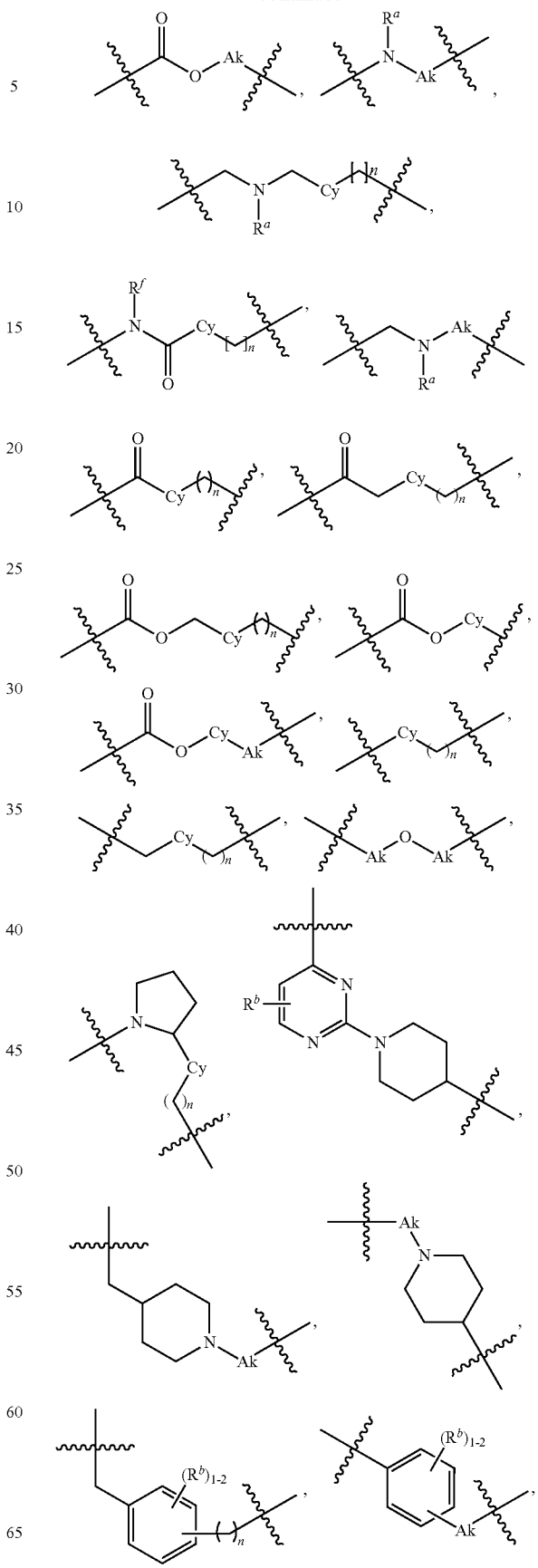

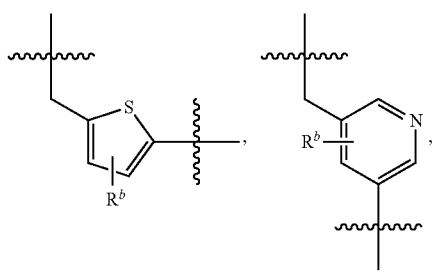
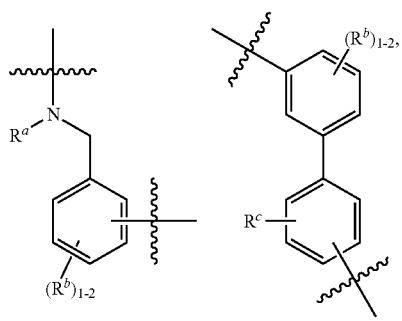
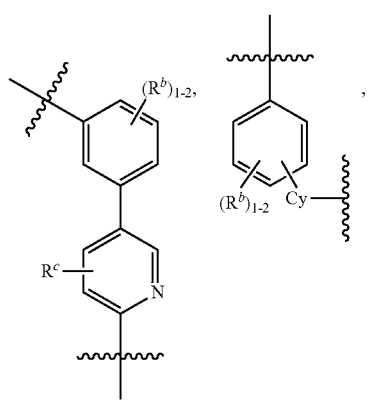
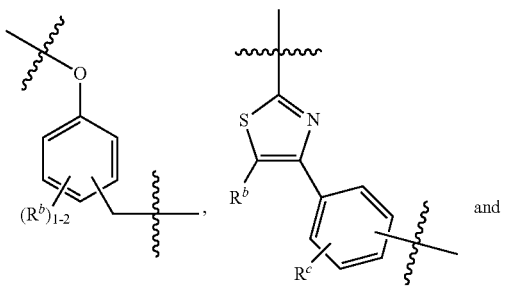
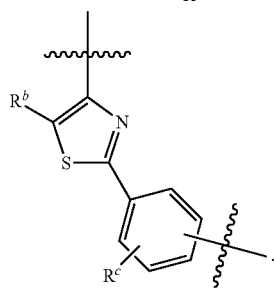

with the proviso that core C and L do not form a N—N bond or a N—O bond;

$X^1$ is absent or is $CR^6$ wherein $R^6$ forms with $R^1$ the following ring:

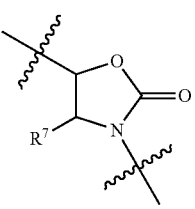

$R^1$ is C(O)O-alkyl, C(O)-alkyl or 5- or 6-membered heteroary optionally substituted with 1 to 3 substituents independently selected from $C_{1-7}$alkyl, hydroxy-$C_{1-7}$alkyl, $C_{1-7}$alkoxy, amino, $C_{1-7}$alkylamino, di-$C_{1-7}$alkylamino, amino-$C_{1-7}$alkyl, $C_{1-7}$alkylamino-$C_{1-7}$alkyl, di-$C_{1-7}$alkylamino-$C_{1-7}$alkyl, (hydroxy$C_{1-7}$alkyl)amino, hydroxy-$C_{1-7}$alkoxy, halo, benzyloxy, 5- or 6-membered heterocyclyl or 5- or 6-membered heteroaryl wherein each heteroaryl and heterocyclyl are optionally substituted with 1 to 3 substituents independently selected from oxo, $C_{1-7}$alkyl, $C_{1-7}$alkanoyl and hydroxy;

$R^5$ in each instance, is independently halo, halo-$C_{1-7}$alkyl, $NO_2$ or CN;

p is 0, 1 or 2;

n is 0, 1 or 2;

$R^2$, $R^3$ and $R^4$ are independently H, $C_{1-7}$alkyl, halo-$C_{1-7}$alkyl, $C_{1-7}$alkoxy-$C_{1-7}$alkyl or $C_{6-10}$aryl-$C_{1-7}$alkyl;

$R^7$ is H or $C_{1-7}$alkyl;

$R^a$ is H, $C_{1-7}$alkyl or $C_{3-7}$cycloalkyl, C(O)—$C_{1-7}$alkyl, C(O)O—$C_{1-7}$alkyl;

$R^b$, $R^c$ and $R^d$ are independently H, $C_{1-7}$alkyl, $C_{3-7}$cycloalkyl, CN, halo-$C_{1-7}$alkyl, $C_{1-7}$alkoxy, halo, halo-$C_{1-7}$alkoxy, $C_{3-7}$cycloalkyloxy, phenyl, 5- or 6-membered ring heteroaryl, or hydroxy;

$R^f$ is H, $C_{1-7}$alkyl or $C_{3-7}$cycloalkyl;

Ak is $C_{1-6}$ linear or branched alkyl;

Cy is $C_{3-7}$ cycloalkyl.

In embodiment 3, the invention pertains to a method or use according to embodiment 1, 1A or 2 wherein C is a core structure selected from:

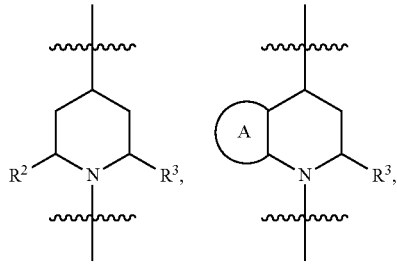
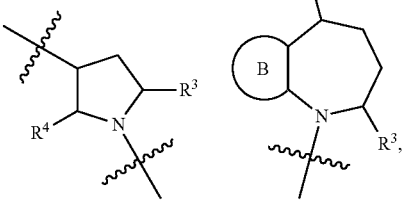

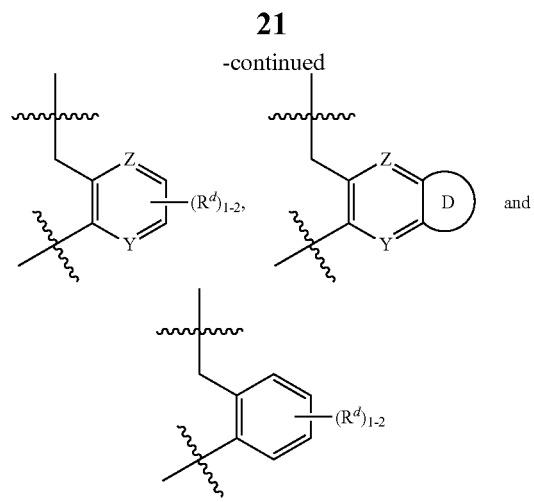

Y and Z are independently CH or N;
Rings A and B are independently phenyl or 5- or 6-membered heteroaryl wherein phenyl and hereroaryl are optionally substituted with 1 to 3 substituents independently selected from $C_{1-7}$alkyl, $C_{1-7}$alkoxy, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;
D is $C_{3-7}$cycloalkyl, phenyl, 5- or 6-membered heteroaryl wherein phenyl and hereroaryl are optionally substituted with 1-3 substituents independently selected from 1 to 3 substituents independently selected from $C_{1-7}$alkyl, $C_{1-7}$alkoxy, CN, $NO_2$, $C_{3-7}$cycloalkyl-$C_{1-7}$alkyl, halo, halo-$C_{1-7}$alkyl, halo-$C_{1-7}$alkoxy, amino, $C_{1-7}$alkylamino, di-$C_{1-7}$alkylamino, $C_{3-7}$cycloalkyl and $C_{3-7}$cycloalkoxy;
L is a linker selected from straight or branched $C_{1-7}$alkyl or a linker selected from:

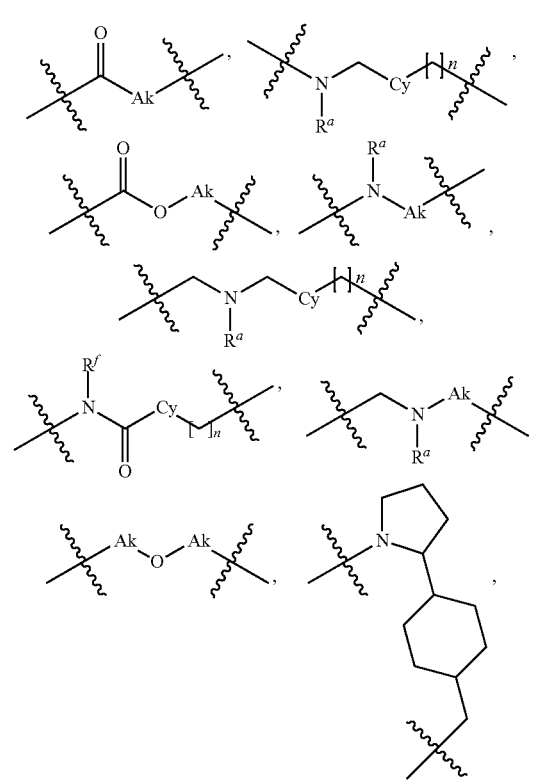

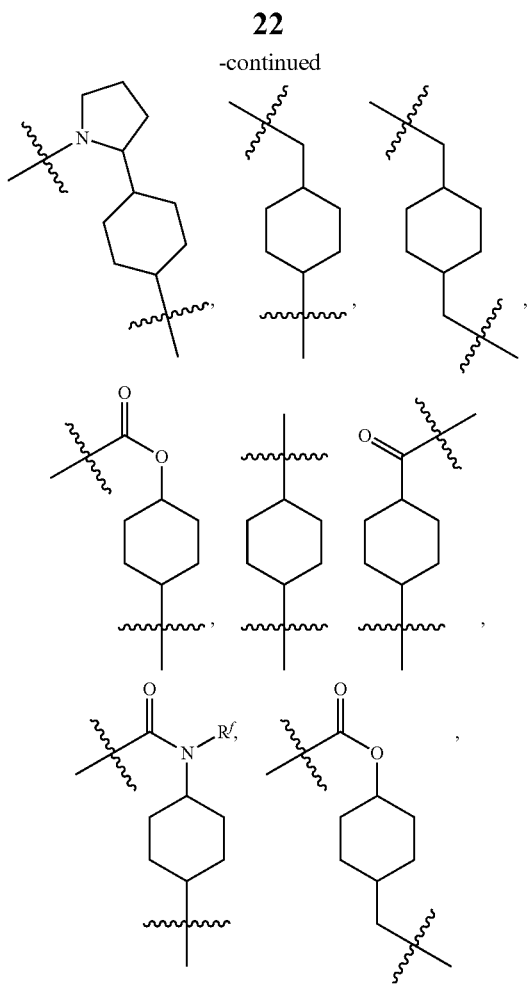

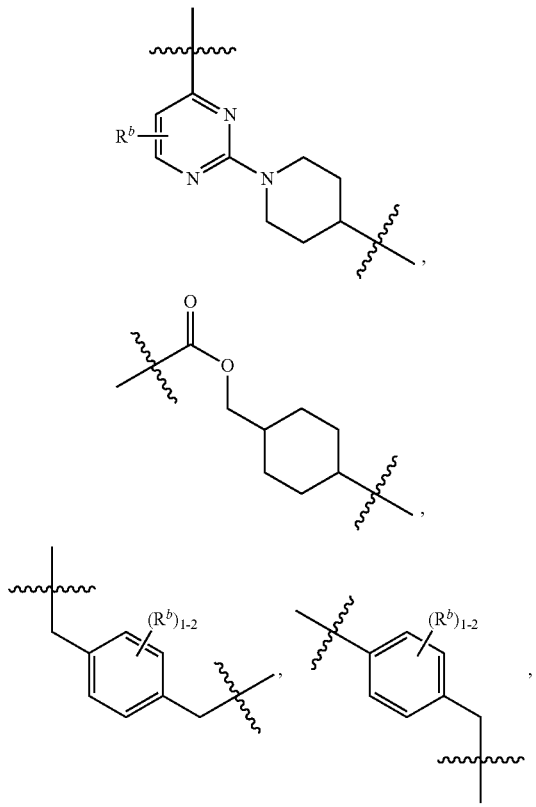

-continued
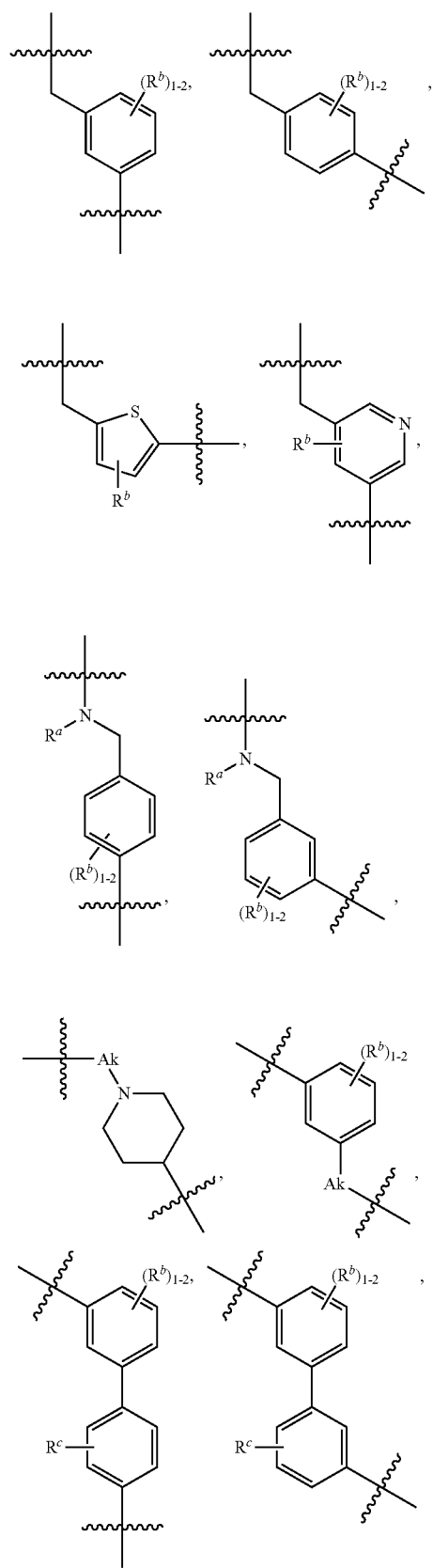
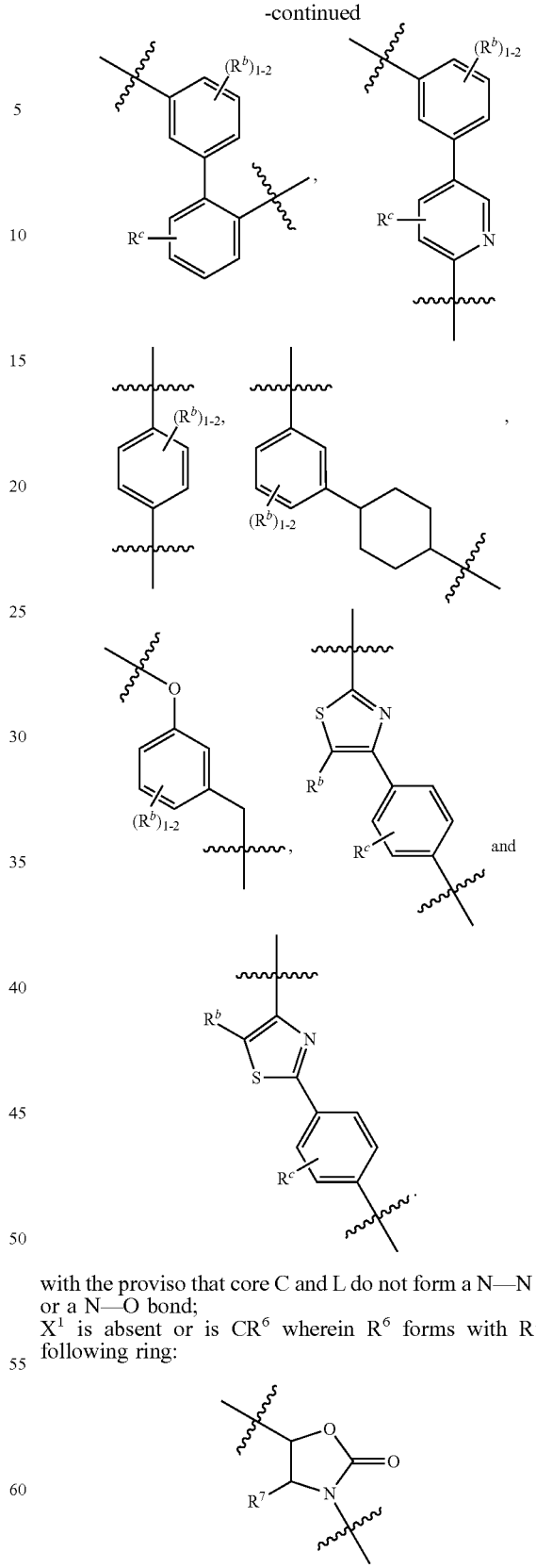
with the proviso that core C and L do not form a N—N bond or a N—O bond;
$X^1$ is absent or is $CR^6$ wherein $R^6$ forms with $R^1$ the following ring:
$R^1$ is C(O)O-alkyl, C(O)-alkyl or 5- or 6-membered heteroary optionally substituted with 1 to 3 substituents independently selected from $C_{1-7}$alkyl, hydroxy-$C_{1-7}$alkyl, $C_{1-7}$alkoxy, amino, $C_{1-7}$alkylamino, di-$C_{1-7}$alkylamino, amino-$C_{1-7}$alkyl, $C_{1-7}$alkylamino-$C_{1-7}$alkyl, di-$C_{1-7}$alkylamino-$C_{1-7}$alkyl, (hydroxy$C_{1-7}$alkyl)amino, hydroxy-$C_{1-7}$alkoxy, halo, benzyloxy, 5- or 6-membered heterocyclyl or 5- or 6-membered heteroaryl wherein each heteroaryl and heterocyclyl are optionally substituted with 1 to 3 substituents independently selected from oxo, $C_{1-7}$alkyl, $C_{1-7}$alkanoyl and hydroxy;

$R^5$ in each instance, is independently halo, halo-$C_{1-7}$alkyl, $NO_2$ or CN;

p is 0, 1 or 2;

n is 0, 1 or 2;

$R^2$, $R^3$ and $R^4$ are independently H, $C_{1-7}$alkyl, halo-$C_{1-7}$alkyl, $C_{1-7}$alkoxy-$C_{1-7}$alkyl or $C_{6-10}$aryl-$C_{1-7}$alkyl;

$R^7$ is H or $C_{1-7}$alkyl;

$R^a$ is H, $C_{1-7}$alkyl or $C_{3-7}$cycloalkyl, C(O)—$C_{1-7}$alkyl, C(O)O—$C_{1-7}$alkyl;

$R^b$, $R^c$ and $R^d$ are independently H, $C_{1-7}$alkyl, $C_{3-7}$cycloalkyl, CN, halo-$C_{1-7}$alkyl, $C_{1-7}$alkoxy, halo, halo-$C_{1-7}$alkoxy, $C_{3-7}$cycloalkyloxy, phenyl, 5- or 6-membered ring heteroaryl, or hydroxy;

$R^f$ is H, $C_{1-7}$alkyl or $C_{3-7}$cycloalkyl;

Ak is $C_{1-6}$ linear or branched alkyl;

Cy is $C_{3-7}$ cycloalkyl; or a pharmaceutically acceptable salt thereof.

In embodiment 4, the invention pertains to a method or use according to anyone of embodiment 1, 1A, 2 and 3 wherein the compound has Formula II:

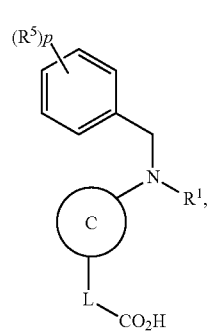

II or a pharmaceutically acceptable salt thereof, wherein $R^1$, $R^5$, C, L and p are as defined in embodiments 1, 1A, 2 or 3, supra.

In embodiment 5, the invention pertains to the method or use according to anyone of embodiments 1, 1A, 2, 3 and 4, wherein the compound has Formula III:

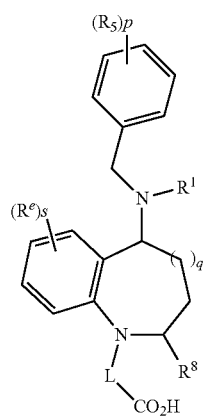

III wherein $R^1$, $R^5$, L and p are as defined in embodiment 1, 1A, 2 or 3, supra; and $R^e$ is $C_{1-7}$alkyl, $C_{1-7}$alkoxy, halo-$C_{1-7}$alkoxy, halo-$C_{1-7}$alkyl, hydroxy, q is 0 or 1; s is 0, 1, 2 or 3 and $R^8$ is H or $C_{1-7}$alkyl, or a pharmaceutically acceptable salt thereof.

In embodiment 5A, the invention pertains to the method or use according to embodiment 5 wherein the compounds are compounds of Formula III where q is 1, disclosed in US applications US 2007/244095 and US 2008/269284 (corresponding to WO 2006/002342) and PCT application WO 2011/002696, each of which are incorporated by reference herein. Examples of compounds of Formula III which are disclosed in WO 2006/002342 are compounds of examples 31, 32, 89, 91, 92, 94, 101, 111, 122, 123, 125, 130, 134, 141 to 143, 153, 154, 175, 176, 197, 198 and 201 to 204, or pharmaceutically acceptable salt thereof.

In embodiment 5B, the invention pertains to the method or use according to embodiment 5 wherein the compounds are compounds of Formula III where q is 0, disclosed in US 2006/0063803, which is incorporated by reference. Examples of compound of Formula III which are disclosed in US 2006/0063803 are compounds of examples 5, 6, 7, 10, 18, 26, 69, 70 to 74, 78 and 82 to 84, or a pharmaceutically acceptable salt thereof.

In embodiment 5C, the invention pertains to the method or use according to embodiment 5, wherein q is 1 and $R^8$ is H, represented by Formula IIIA:

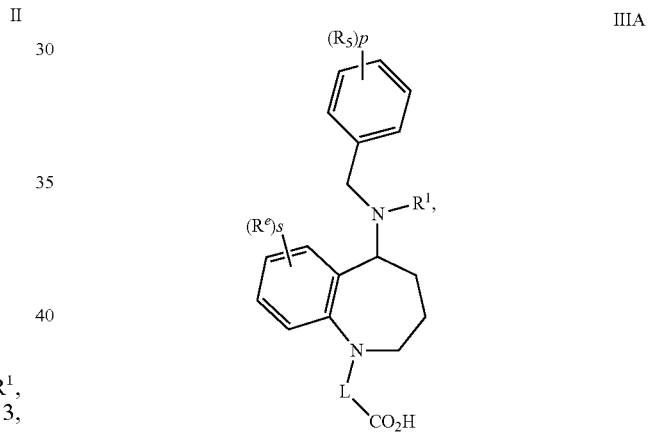

IIIA or a pharmaceutically acceptable salt thereof, wherein $R^5$, $R^1$, L, $R^e$, p and s are as defined in embodiments 1, 1A, 2, 3, 4 and 5, supra.

In embodiment 6, the invention pertains to embodiment 5 or 5C, wherein the Linker L is a $C_{1-6}$ alkyl or a linker selected from:

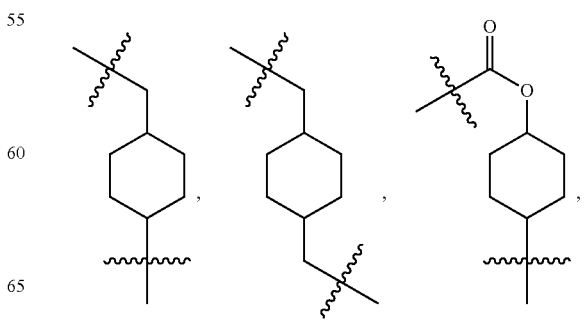

-continued

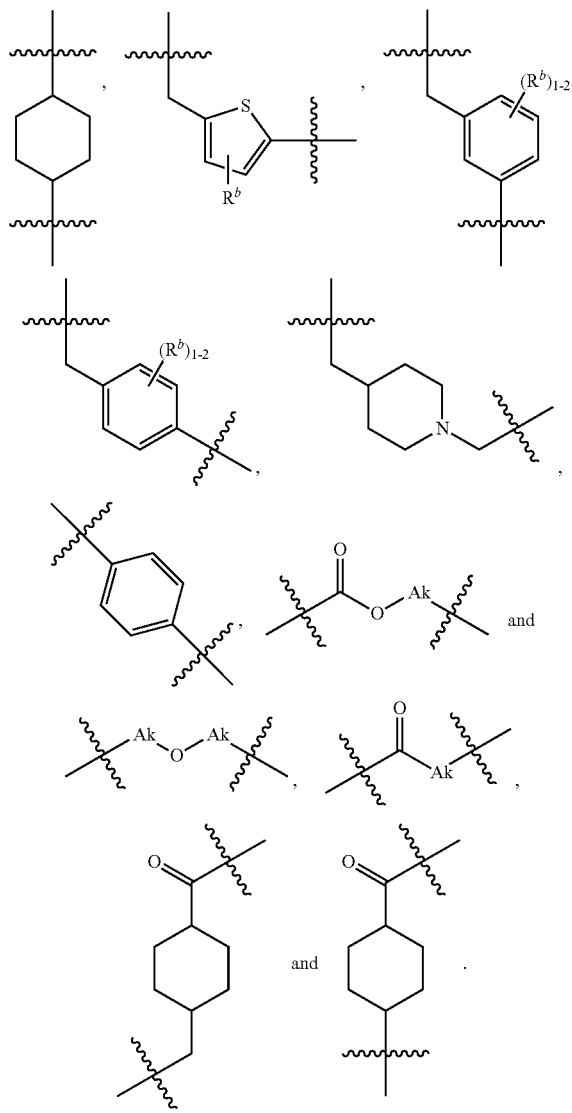

In embodiment 7, the invention pertains to the method or use according to embodiment 5, 5C or 6 wherein L is selected from:

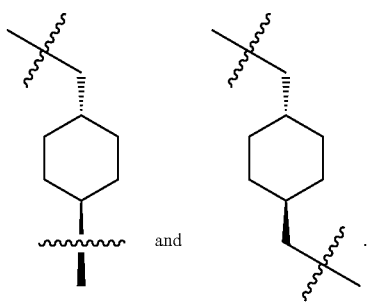

In embodiment 8, the invention pertains to the method or use according to any of embodiments 4 to 7 wherein $R^1$ is a tetrazole optionally substituted with $C_{1-4}$ alkyl; or a pharmaceutically acceptable salt thereof.

In embodiment 8A, the invention pertains to the method or use of embodiment 8, wherein the compound of Formula III is:

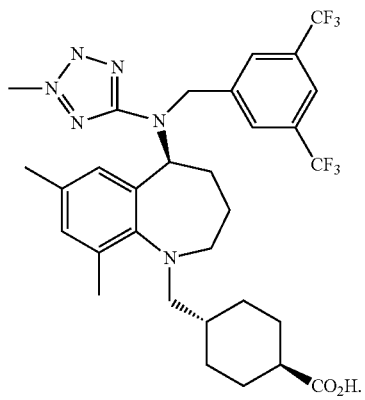

In embodiment 9, the invention pertains to the method or use according to anyone of embodiments 1, 1A, 2, 3 and 4 wherein the compound has Formula IV:

IV

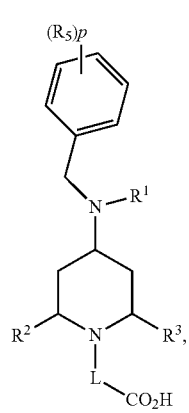

or a pharmaceutically acceptable salt thereof, wherein $R^1$, $R^2$, $R^3$, $R^5$, L and p are as defined in embodiment 1, 1A or 2, supra.

In embodiment 10, the invention pertains to the method or use according to embodiment 9, wherein the compound has the formula IVA:

IVA

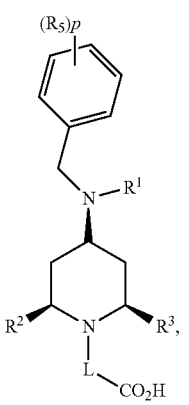

or a pharmaceutically acceptable salt thereof.

In embodiment 10A, the invention pertains to the method or use according to embodiment 10 wherein the compound of Formula IV or IVA are compounds disclosed in US 2009/0118287 (WO 2009/059943) which is incorporated by reference therein.

In embodiment 11, the invention pertains to the method or use according to embodiment 9 or 10, wherein L is selected from:

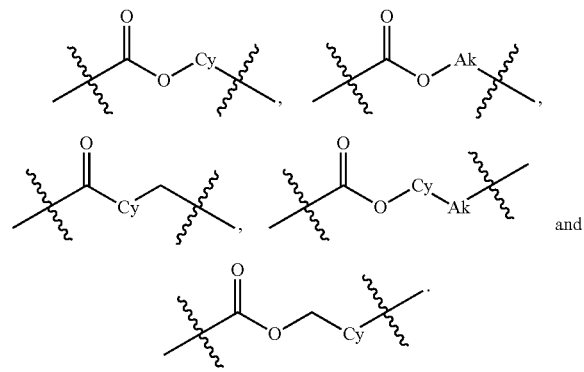

In embodiment 12, the invention pertains to the method or use according to embodiment 11 wherein L is selected from:

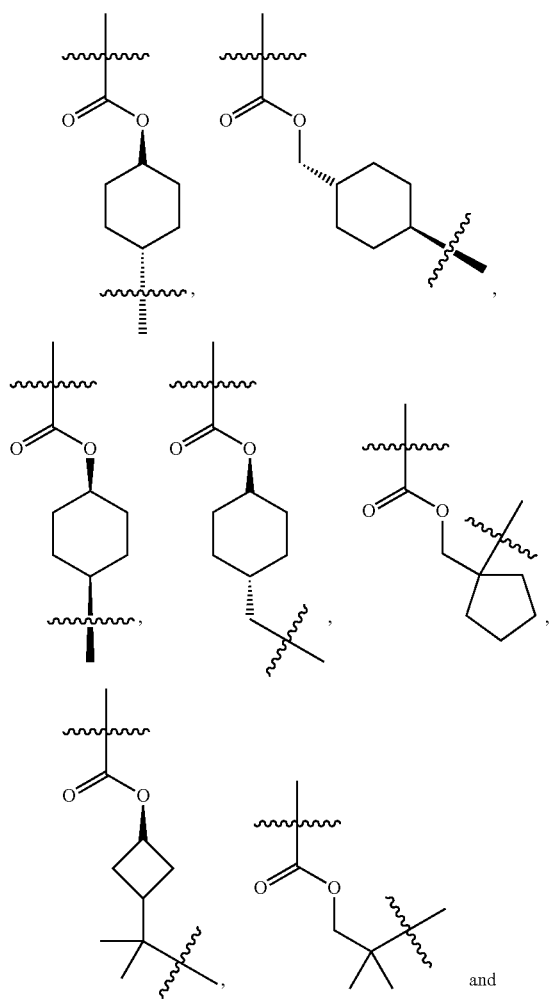

and

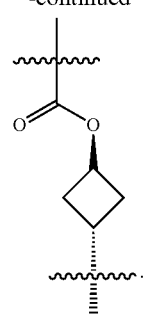

In embodiment 13, the invention pertains to the method or use according to anyone of embodiments 9 to 12 wherein $R^1$ is a 5- or 6-membered heteroaryl, wherein said heteroaryl is optionally substituted with one to three substituents selected from halogen, $C_{1-7}$alkyl, hydroxy-$C_{1-7}$alkyl, di-$C_{1-7}$alkylamino, $C_{1-7}$alkoxy, 5- or 6-membered heterocyclyl or 5- or 6-membered heteroaryl, wherein said heterocyclyl and heteroaryl are further optionally substituted with one to three substituents selected from $C_{1-7}$alkyl, $C_{1-7}$alkanoyl or hydroxy.

In embodiment 14, the invention pertains to the method or use according to embodiment 13, wherein $R^1$ is pyrimidine substituted with morpholino, imidazolyl, pyrazoyl or tetrazolyl wherein imidazolyl, pyrazoyl and tetrazolyl are optionally substituted with $C_{1-7}$alkyl.

In embodiment 15, the invention pertains to the method or use according to anyone of embodiments 9 to 14, wherein $R^2$ and $R^3$ are independently $C_{1-4}$alkyl.

In embodiment 16, the invention pertains to the method or use according to anyone of embodiments 1, 1A, 2, 3 and 4, wherein the compound has Formula V:

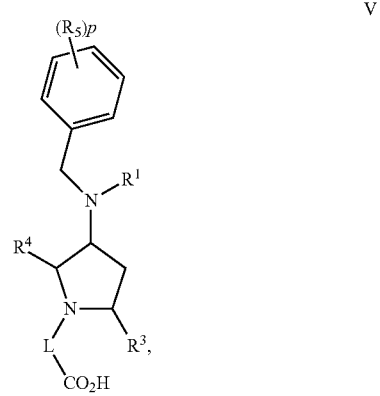

or a pharmaceutically acceptable salt thereof, wherein $R^1$, $R^3$, $R^4$, $R^5$, L and p are as defined in embodiment 1, 1A or 2, supra.

In embodiment 17, the invention pertains to the method or use according to embodiment 16 wherein the compound has Formula VA:

VA

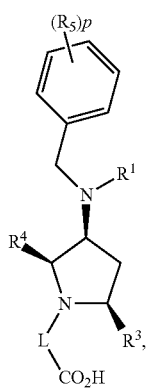

or pharmaceutically acceptable salt thereof.

In embodiment 17A, the invention pertains to the method or use according to embodiment 17, wherein the compound are the compounds of Formula V or VA disclosed in US 2010/0311750 (WO 2009/071509), which is incorporated by reference therein.

In embodiment 18, the invention pertains to the method or use according to embodiment 16 or 17 wherein L is selected from:

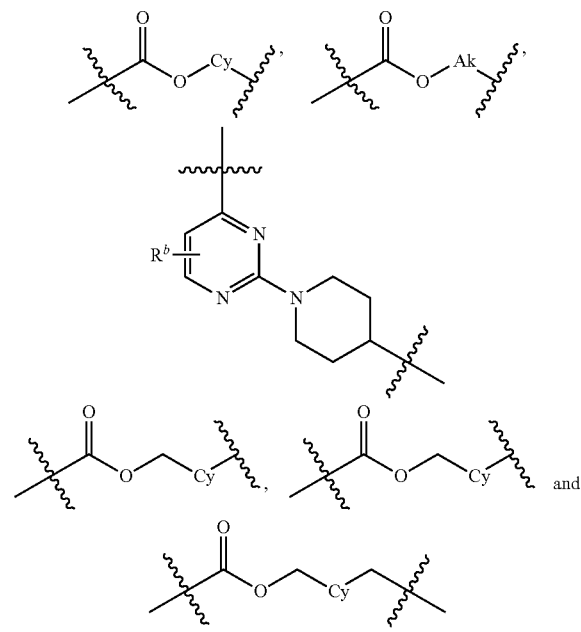

In embodiment 19, the invention pertains to the method or use according to embodiment 18 wherein L is selected from:

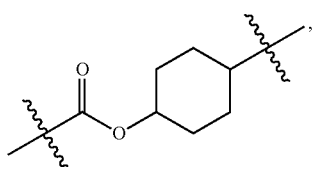

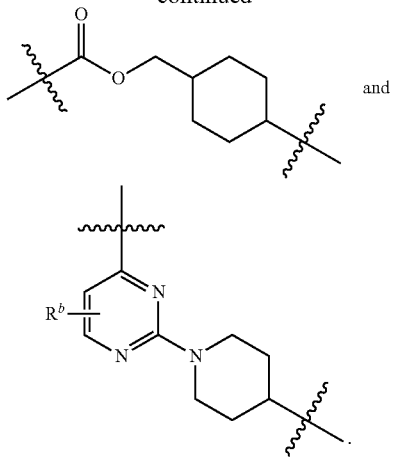

In embodiment 20, the invention pertains to the method or use according to anyone of embodiments 16 to 19 wherein $R^3$ is $C_{1-7}$alkyl and $R^4$ is H.

In embodiment 21, the invention pertains to the method or use according to anyone of embodiments 16 to 20 wherein $R^1$ is a 5- or 6-membered heteroaryl, wherein said heteroaryl is optionally substituted with one to three substituents selected from halogen, $C_{1-7}$alkyl, hydroxy-$C_{1-7}$alkyl, di-$C_{1-7}$alkylamino, $C_{1-7}$alkoxy, 5- or 6-membered heterocyclyl or 5- or 6-membered heteroaryl, wherein said heterocyclyl and heteroaryl are further optionally substituted with one to three substituents selected from $C_{1-7}$alkyl, $C_{1-7}$alkanoyl or hydroxy.

In embodiment 22, the invention pertains to the method or use according to embodiment 21 wherein $R^1$ is pyrimidine substituted with morpholino, imidazolyl, pyrazoyl or tetrazolyl wherein imidazolyl, pyrazoyl and tetrazolyl are optionally substituted with $C_{1-7}$alkyl.

In embodiment 23, the invention pertains to the method or use according to embodiment 1, 1A, 2, 3 or 4 wherein the compound has Formula VI:

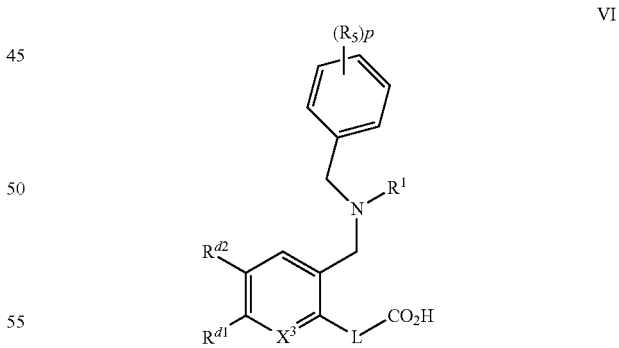

wherein $R^5$, $R^1$, L and p are as defined in embodiment 1, 1A or 2, supra; and $X^3$ is CH or N; and $R^{d1}$ and $R^{d2}$ are independently selected from H, $C_{1-7}$alkyl, halo, halo-$C_{1-7}$alkyl; or $R^{d1}$ and $R^{d2}$ form together with the atoms to which they are attached a phenyl optionally substituted with 1-3 substituents independently selected from halo, $C_{1-7}$alkyl, halo-$C_{1-7}$alkyl; or a pharmaceutically acceptable salt thereof.

In embodiment 23A, the invention pertains to method or use according to embodiment 23, wherein the compounds are compounds of Formula VI which are disclosed in US 2009/0075968 (WO 2007/073934); in US 2009/0227580 (WO 2007/128568) and in WO 2004/020393, each of which are incorporated by reference herein.

In embodiment 24, the invention pertains to the method or use according to embodiment 23, wherein L is selected from:

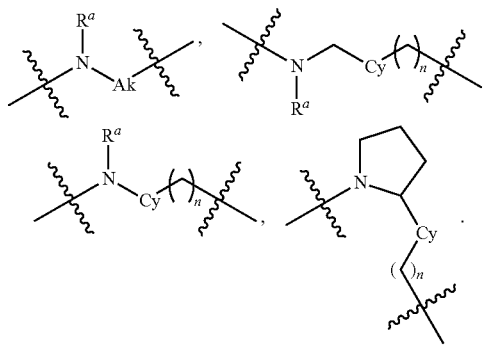

In embodiment 25, the invention pertains to the method or use according to embodiment 24, wherein L is selected from:

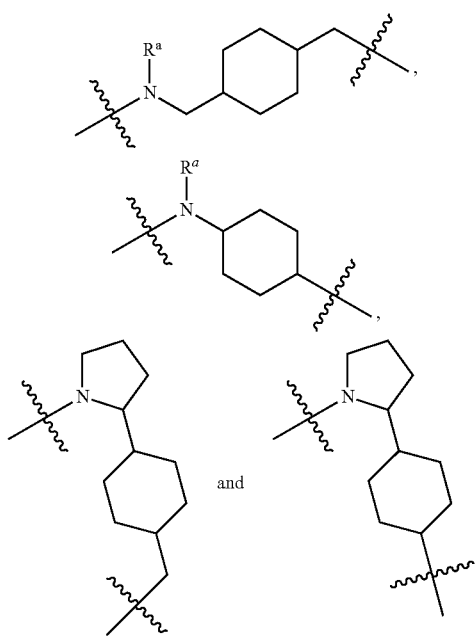

In embodiment 26, the invention pertains to the method or use according to anyone of embodiments 23 to 25 wherein $R^1$ is tetrazole optionally substituted with $C_{1-4}$alkyl.

In embodiment 27, the invention pertains to the method or use according to anyone of embodiments 23 to 26 wherein $X^3$ is N, $R^{d1}$ is H and $R^{d2}$ is halo-$C_{1-7}$alkyl; or $R^{d1}$ and $R^{d2}$ form together with the atoms to which they are attached a phenyl which is optionally substituted with 1 to 2 substituents independently selected from halo, $C_{1-7}$alkyl.

In embodiment 27A, the invention relates to the method or use according to anyone of embodiments 23 to 26, wherein $X^3$ is CH, $R^{d1}$ is H or $C_{1-7}$alkyl and $R^{d2}$ is halo or halo-$C_{1-7}$alkyl. In a further aspect of embodiment 27A, the invention pertains to method or use wherein the compounds are compounds of Formula VI as disclosed in WO2004/020393.

In embodiment 27B, the invention pertains to the method or use according to embodiment 1, 1A, 2 or 3 wherein the compound has Formula VIA:

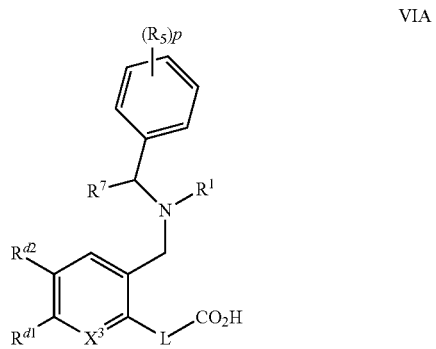

wherein $R^5$, $R^7$, $R^1$, L and p are as defined in embodiment 1, 1A or 2, supra; and $X^3$ is CH or N; and $R^{d1}$ and $R^{d2}$ are independently selected from H, $C_{1-7}$alkyl, halo, halo-$C_{1-7}$alkyl; or a pharmaceutically acceptable salt thereof.

In embodiment 27C, the invention pertains to method or use according to embodiment 27B, wherein the L is selected from:

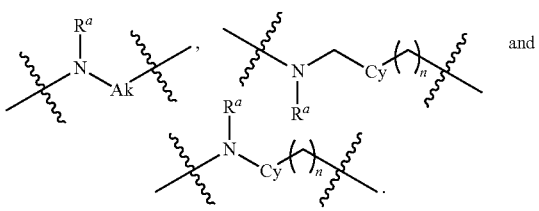

In embodiment 27D, the invention pertains to method or use wherein the compounds are compounds of Formula VIA which are disclosed in US2009/082352, which is incorporated by reference herein.

In embodiment 27E, the invention pertains to method or use according to embodiment 27B, 27C or 27D, wherein $R^7$ is alkyl and $R^1$ is pyrimidine optionally substituted with $C_{1-7}$alkoxy wherein alkoxy is further optionally substituted with —S(O)$_2$—C$_{1-4}$alkyl.

In embodiment 27F. the invention pertains to method or use according to embodiment 27B, 27C, 27D or 27E wherein $X^3$ is CH, $R^{d1}$ is H or $C_{1-7}$alkyl and $R^{d2}$ is halo-$C_{1-7}$alkyl.

In embodiment 28, the invention pertains to the method or use according to embodiment 1, 1A, 2 or 3 having Formula VII:

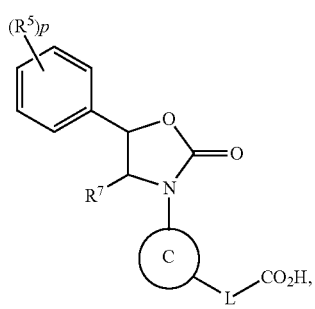

wherein $R^5$, $R^7$, L and p are as defined in embodiment 1, 1A or 2; supra; or a pharmaceutically acceptable salt thereof.

In embodiment 29, the invention pertains to the method or use according to embodiment 28 having formula VIIA:

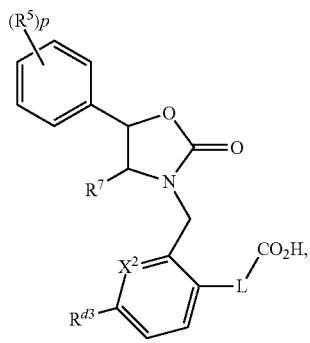

VIIA wherein $X^2$ is $CR^{d4}$ or N, $R^{d3}$ is $C_{1-7}$alkoxy, $C_{1-7}$alkyl, halo-$C_{1-7}$alkyl, halo-$C_{1-7}$alkoxy, $R^{d4}$ is H or $R^{d3}$ and $R^{d4}$ can form together a 5- or 6-membered heterocyclyl or heteroaryl, a phenyl or a cycloalkyl; or a pharmaceutically acceptable salt thereof.

In embodiment 29A, the invention pertains to the method or use according to embodiment 29, wherein the compounds are compounds of Formula VII which are disclosed in US applications US 2009/075979 (corresponding to WO2007/081571) and US 2009/042892 (corresponding to WO2007/081569), each of which is incorporated by reference. Examples of compounds of Formula VII which are disclosed in WO 2007/081571 are compounds of examples 13 to 15, 63 to 67, 69-77, 79 to 82, 84, 87 and 89, or pharmaceutically acceptable salt thereof. Examples of compounds of Formula VII which are disclosed in WO 2007/081569 are compounds of examples 62, 64, 108 to 111, 113 to 118, 120, 121, 123, 125 and 127, or pharmaceutically acceptable salt thereof.

In embodiment 30, the invention pertains to the method or use according to claim 28 or 29 wherein L is selected from:

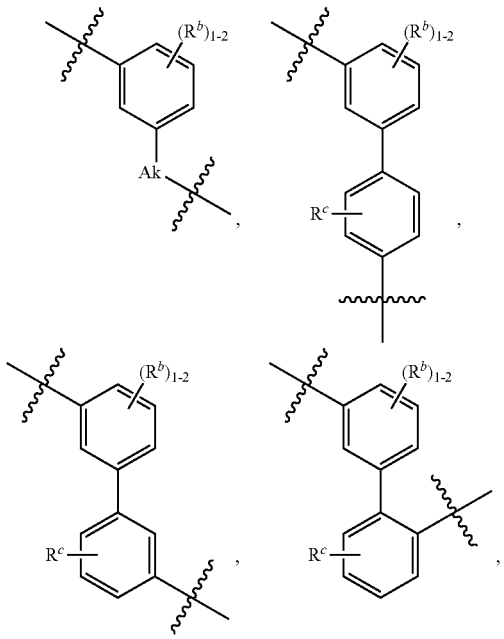

-continued

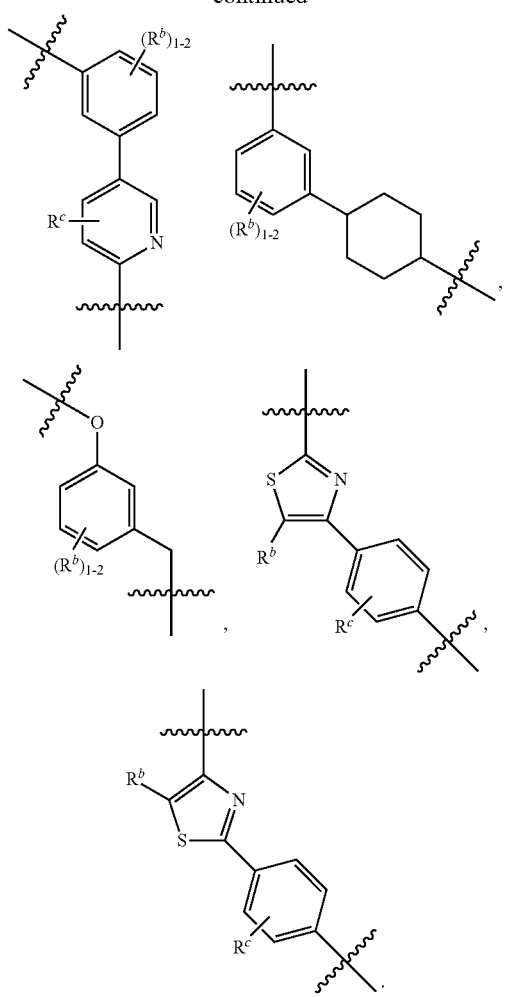

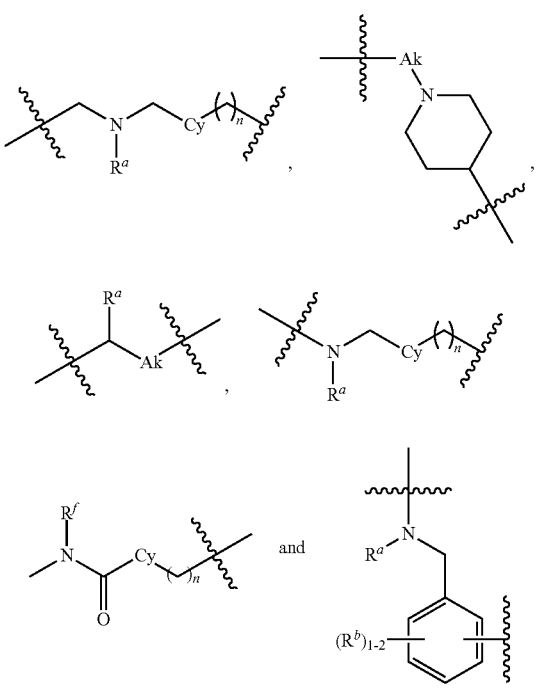

In embodiment 31, the invention pertains to the method or use according to anyone of embodiments 28 to 30 wherein L is
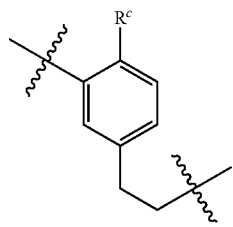
wherein $R^c$ is $C_{1-7}$alkoxy or halo-$C_{1-7}$alkoxy.
In embodiment 32, the invention pertains to the method or use according to embodiments 1, 1A or 2 wherein the compound is selected from:
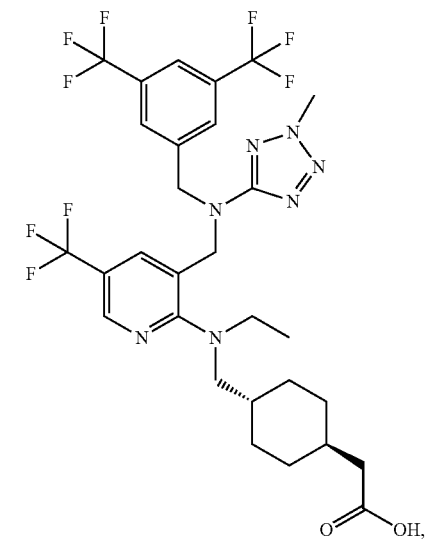
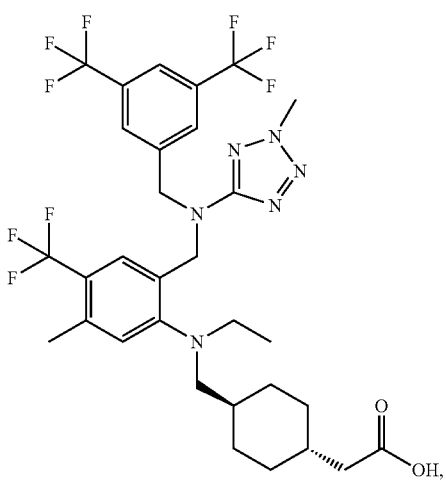
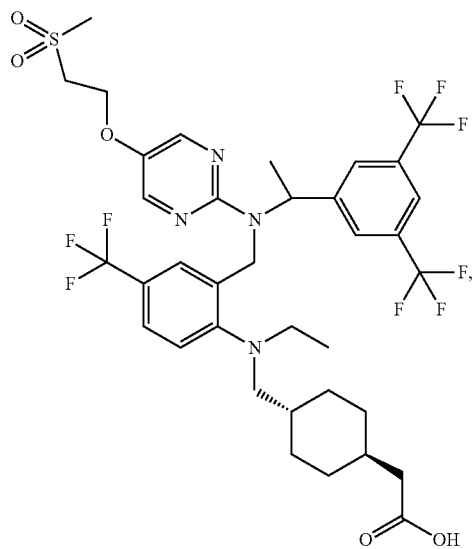
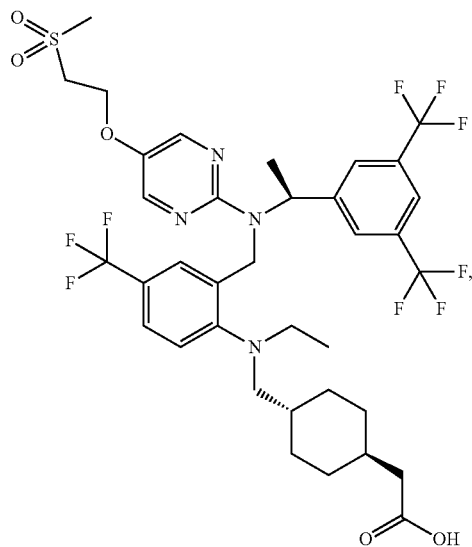
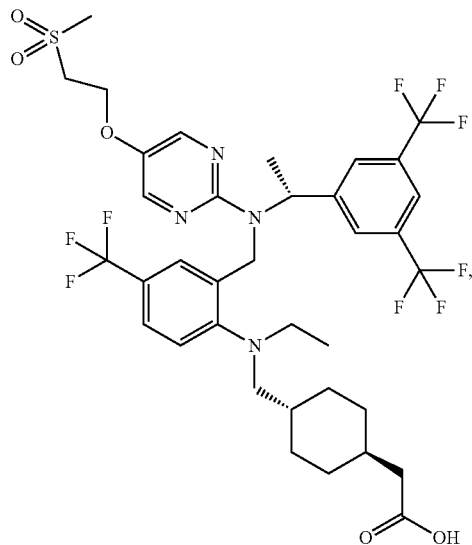

39
-continued
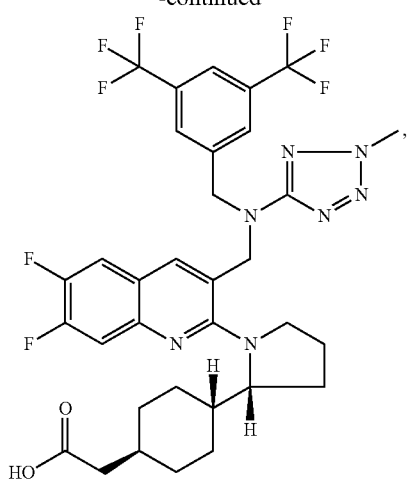
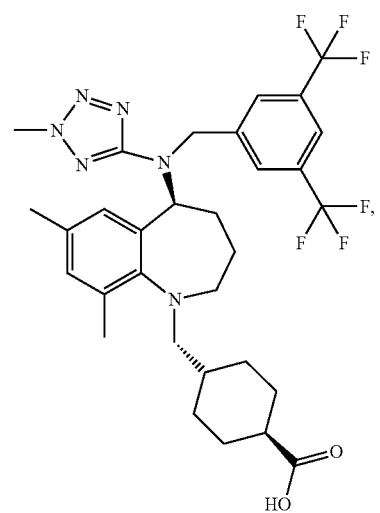
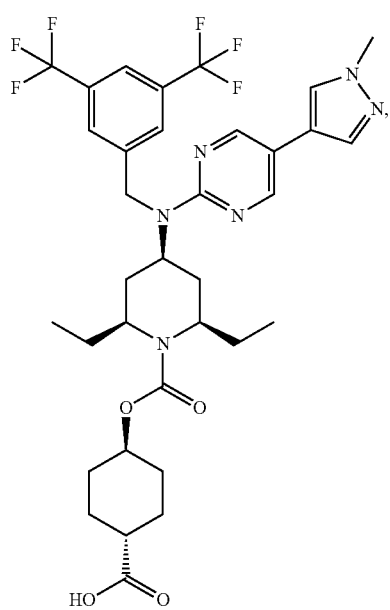
40
-continued
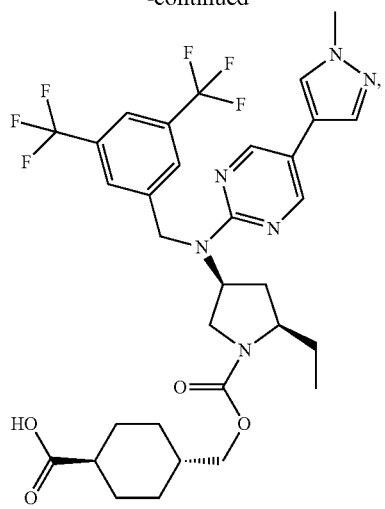
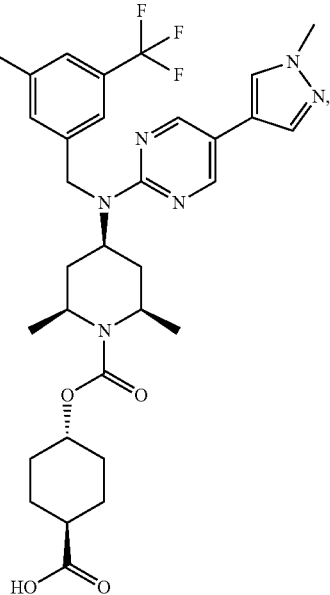

41
-continued
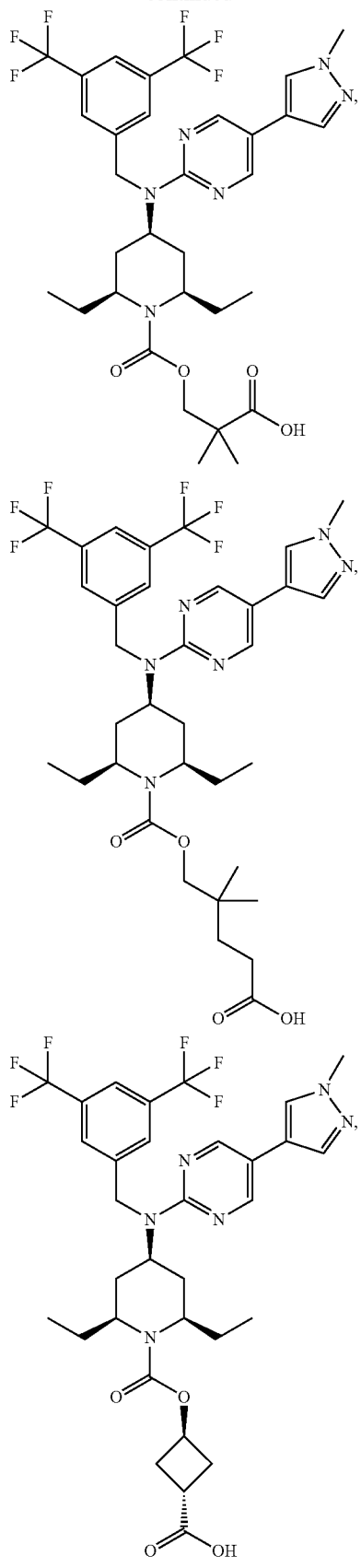
42
-continued
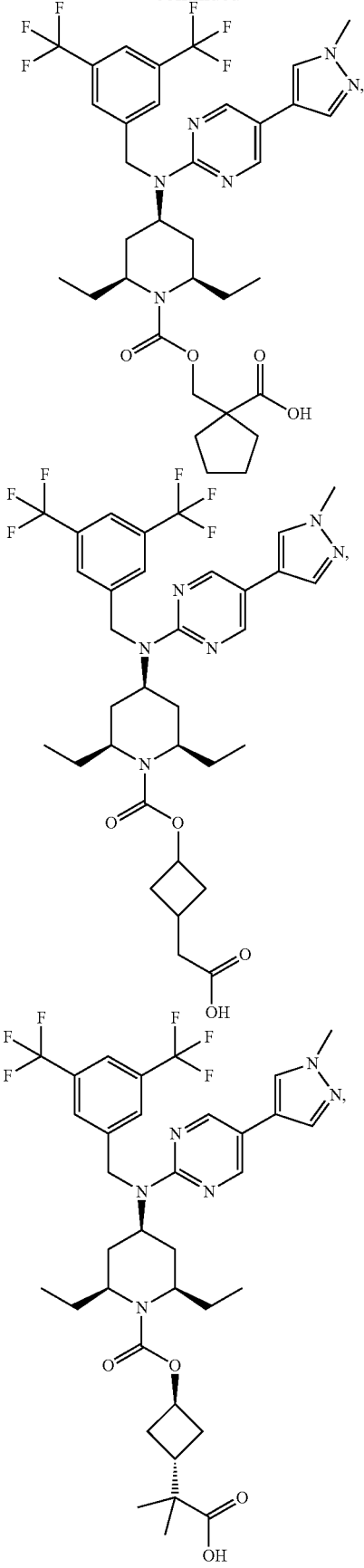

In embodiment 34, the invention pertains to the method or use according to embodiment 1, 1A or 2 wherein the compound is selected from:
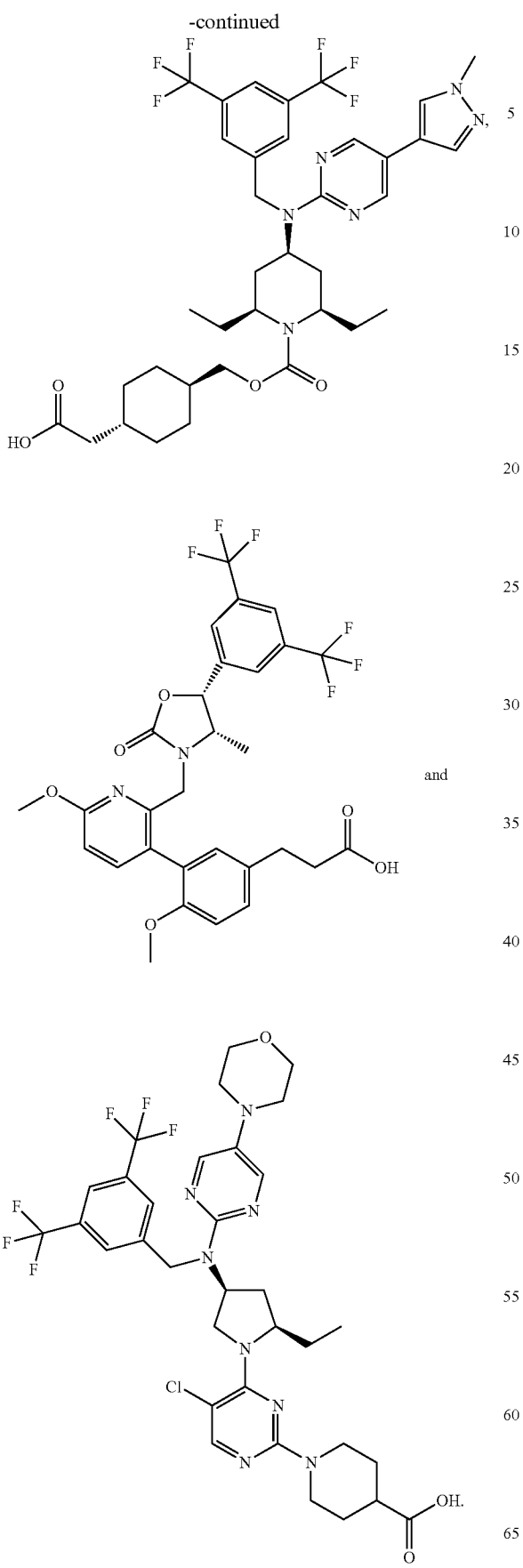
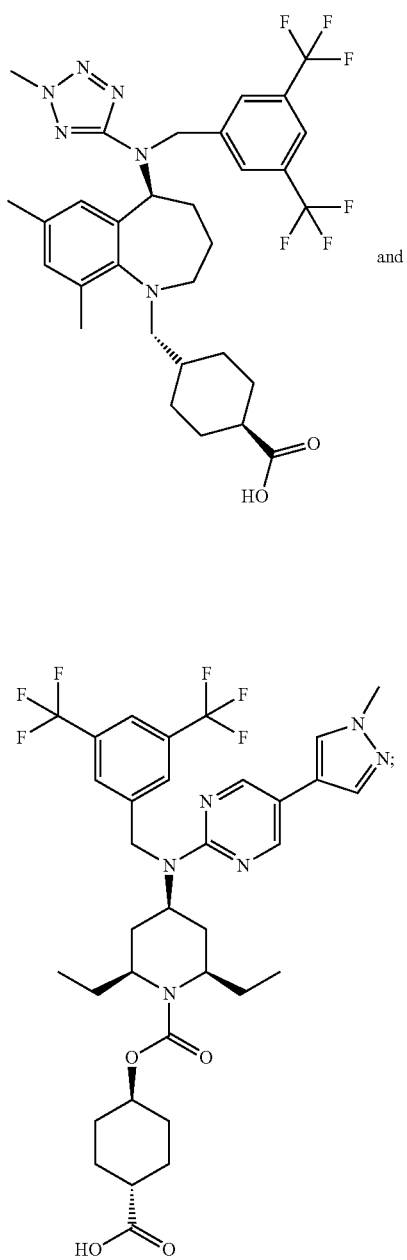
or a pharmaceutically acceptable salt thereof.
In embodiment 34A, the invention pertains to the method or use according to embodiment 1, 1A or 2 wherein the compound is:

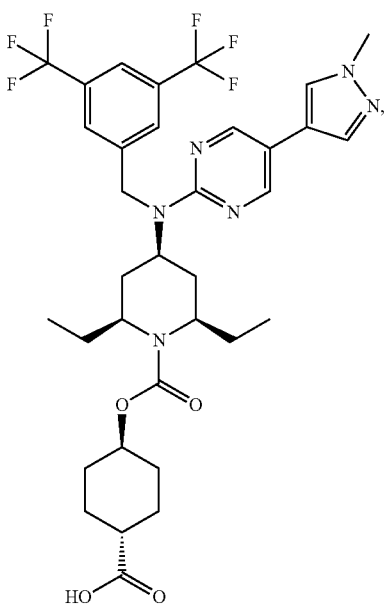

or a pharmaceutically acceptable salt thereof.

In embodiment 35, the invention pertains to the method or use of a compound according to anyone of the proceeding embodiments, in combination with at least one other therapeutic agent as a combined preparation for simultaneous, separate or sequential use in therapy.

In embodiment 36, the invention pertains to the method or use according to embodiment 35 wherein the other therapeutic agent is selected from statin, cholesterol absorption inhibitor, apoA-I up-regulator/inducer, pre-beta HDL mimetic, ABCA1 stabilizer or inducer, LXR agonist, FXR agonist, phospholipid transfer protein (PLTP) inhibitor, aldosterone synthase inhibitor (ASI), fibric acid derivative, fish oil, DGAT1 inhibitor and endothelial lipase inhibitor, or a pharmaceutically acceptable salt thereof.

In embodiment 37, the invention pertains to method or use according to anyone of the preceding embodiments wherein the triglyceride level is a fasting triglyceride level >150 mg/dL.

In embodiment 38, the invention pertains to method or use according to anyone of the preceding embodiments wherein the triglyceride level is a fasting triglyceride level >200 mg/d L.

In embodiment 39, the invention pertains to method or use according to anyone of the preceding embodiments wherein the triglyceride level is a fasting triglyceride level >500 mg/d L.

In embodiment 40, the invention pertains to method or use according to anyone of the preceding embodiments of raising HDL-C by 100%.

It will be noted that the structure of some of the compounds for use in this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts, for use in the invention, can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts for use in the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1H$, $^2H$ or D, $^3H$); any carbon represented by "C" in any of the formulae herein is intended to represent all isotopic forms of carbon (e.g. $^{11}C$, $^{12}C$, $^{13}C$, $^{14}C$); any nitrogen represented by "N" is intended to represent all isotopic forms of nitrogen (e.g. $^{14}N$, $^{15}N$). Other examples of isotopes that are included in the invention include isotopes of oxygen, sulfur, phosphorous, fluorine, iodine and chlorine, such as $^{18}F$ $^{31}P$, $^{32}P$, $^{35}S$, $^{36}Cl$, $^{125}I$. The invention includes various isotopically labeled compounds as defined herein, for example those into which radioactive isotopes, such as $^3H$, $^{13}C$, and $^{14}C$ are present. In one embodiment, the atoms in the formulae herein occur in their natural abundance. In another embodiment, one or more hydrogen atom may be enriched in $^2H$; or/and one or more carbon atom may be enriched in $^{11}C$, $^{13}C$ or $^{14}S$; or/and one or more nitrogen may be enriched in $^{14}N$. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to anyone of the formulae I to VIIA. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds according to anyone of formulae I to VIIA can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds for use in the invention, i.e. compounds according to anyone of formulae I to VIIA that contain groups capable of acting as donors and/or acceptors for hydrogen bonds may be capable of forming co-crystals with suitable co-crystal formers. These co-crystals may be prepared from compounds according to anyone of formulae I to VIIA by known co-crystal forming procedures. Such procedures include grinding, heating, co-subliming, co-melting, or contacting in solution compounds according to anyone of formulae I to VIIA with the co-crystal former under crystallization conditions and isolating co-crystals thereby formed. Suitable co-crystal formers include those described in WO 2004/078163. Hence the invention further provides co-crystals comprising a compound according to anyone of formulae I to VIIA or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, a disorder or a disease or a symptom thereof (i) ameliorated by the inhibition CETP or (ii) associated with CETP activity, or (iii) characterized by abnormal activity of CETP; or (2) reduce or inhibit the activity of CETP; or (3) reduce or inhibit the expression of CETP. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of CETP; or at least partially reduce or inhibit the expression of CETP.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds for use in the present invention are either used in the free form, as a salt thereof.

When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization.

In another aspect, the present invention provides a pharmaceutical composition comprising a compound of the present invention or a pharmaceutically acceptable salt thereof and one or more pharmaceutically acceptable carriers for use in the prevention, amelioration or treatment of atherosclerosis or dyslipidemia, or for raising HDL-C and/or lowering LDL-C, in subject with high triglyceride level. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds, for use in the invention.

Anhydrous pharmaceutical compositions and dosage forms for use in the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Suitable pharmaceutical composition includes composition comprising a solid amorphous dispersion which are prepared by hot melting extrusion processes. Examples of solid amorphous dispersion are represented below.

Formulation Example 1: Solid Amorphous Dispersion of Compound of Example 8

| Formulation | % wt |
|---|---|
| Intragranular | |
| Compound of Example 8 Free Form | 20 |
| Copovidone | 50 |
| Extragranular | |
| Microcrystalline Cellulose | 24 |
| Magnesium Sterate | 0.5 |
| Crospovidone | 5 |
| Colloidal Silicone Dioxide (Aerosil) | 0.5 |
| Total | 100 |

Formulation Example 2: Solid Amorphous Dispersion of Compound of Example 17

| Formulation Intragranular | % wt |
|---|---|
| Compound of Example 17 Free Form | 25 |
| Copovidone | 75 |
| Total | 100 |

Compounds for Use in the Invention:

The compounds of the invention can be synthesized using the methods described in the following applications, US 2009/0075968, US 2009/0227580, US 2006/0063803, US 2009/075979, US 2009/042892, US 2007/244095, WO 2011/028395, WO 2009/027785 and US 2008/269284 each of which is incorporated by reference herein.

The compounds according to anyone of formulae I to VIIA for use in the method of the invention, or a pharmaceutically acceptable salt thereof, in free form or in pharmaceutically acceptable salt form, exhibit valuable pharmacological properties, e.g. CETP inhibitory properties, e.g. as indicated in in vitro and in vivo tests as provided in the next sections and are therefore indicated for the treatment, amelioration and/or prevention of atherosclerosis or dyslipidemia, or for raising HDL-C and/or lowering LDL-C in subject with high triglyceride level.

The pharmaceutical composition or combination of the present invention for use in the method of the invention; can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the severity of the disorder. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Method of the Invention:

In Vitro and In Vivo Assays:

Preparation of Human Pro-Apolipoprotein A-I (Pro-apoA-I)

The cDNA of human pro-apoAI (NCBI accession number: NM_000039) was cloned from human liver QuickClone™ cDNA (Clontech, CA, Cat. No. 7113-1) and inserted to a pET28a vector (Novagen, Germany) for bacterial expression. Expressed protein as a fusion protein with 6×His-tag at N-terminus in BL-21 Gold (DE3) (Strategene, CA) was purified using HiTrap Chelating (GE Healthcare, CT).

Preparation of Donor Microemulsion

Pro-apoA-1 containing microemulsion as a donor particle was prepared following previous report (J. Biol. Chem., 280:14918-22). Glyceryl trioleate (500 ug, Sigma-Aldrich, Cat. No. T7140), 3-sn-phosphatidylcholine (4680 ug, Sigma, Cat. No. P2772), and cholesteryl BODIPY FL 012 (2 mg, Invitrogen, CA, Cat. No. C-3927MP) were dissolved in 1.5 mL of chloroform. The solution was evaporated, and residual solvent was removed under vacuum for more than 1 hr at room temperature. The dried lipid mixture was dissolved in 7 ml of the assay buffer (50 mM Tris-HCl (pH 7.4) containing 150 mM NaCl and 2 mM EDTA) and sonicated in water bath for 1 hr. The solution was split into two tubes of 3.5 ml each. Each tube was sonicated at 50° C. with a microtip (MICROSON™ ULTRASONIC CELL DISRUPTOR, Misonix, Farmingdale, N.Y.) at output power 006 for 10 min (every other 25 seconds). The solution was cooled to 40° C. and 400 ug of pro-apoA-1 was added to each tube (total volume of 4 mL). Then, the solution was sonicated at output power 004 for 20 min (every other 30 seconds). Final Concentration: Glyceryl Tiroleate: 62.5 ug/ml, PC: 585 ug/ml, Bodipy CE: 250 ug/ml, Pro-apoA-1: 100 ug/ml. Centrifuge solution at 5200×g for 5 minutes and store the supernatant at 4'C.

(1) In Vitro Experiments:

Human Serum Samples

Human serum samples were obtained from the Novartis Institutes for BioMedical Research donor program (normal triglyceride samples) or purchased from Bioreclamation (Westbury, N.Y.) or Uniglobe (Reseda, Calif.). General requirements for human serum donors included: male gender, 20-55 years of age, not currently on a lipid altering medication, non-fasting at time of blood collection, and a total cholesterol level between 200-300 mg/dL. Donor samples were selected primarily on the basis of serum triglyceride level, using the following classifications: normal triglycerides (<150 mg/dL); high triglycerides (300-500 mg/dL); and very high triglycerides (750-1200 mg/dL). A total of 4 individual serum samples from each classification were used in these experiments. For each of the 3 triglyceride classifications, two serum sample pools were prepared. The mean plasma triglyceride concentrations (mg/dL) for the pools were: Normal: 101.35; High: 347.5; Very high 1, 868.45; Very high 2, 1269.35.

In Vitro CETP Activity Assay in Human Plasma

Donor solution is prepared by a dilution of donor microemulsion with assay buffer (1.7 ul donor+8.3 ul Buffer). Human serum (25 µL), assay buffer (14 µL) and 50× test compound dissolved in 100% dimethylsulfoxide (1 µL) are added to each well of 384 well black, clear-bottom plate (NUNC. Thermo Fisher #242764). The reaction is started by the addition of donor solution (10 µL) into each well. Fluorescence intensities are measured every 10 min at 37° C. with excitation wave length of 485 nm and emission wavelength of 515 nm over an 80 minute period, using a SpectraMax M5 from Molecular Devices (Sunnyvale, Calif.). The CETP activity (RFU/min) is defined as the change of fluorescence intensity from 40 to 70 min. Percent CETP inhibition is calculated as follows: ((100% Act−Wellcmpnd)/100% Act))*100. IC50 values were calculated with GraphPad Prism 5 software.

Using the test assay (as described above) compounds of the invention exhibited inhibitory efficacy in accordance to Table 1, provided infra.

TABLE 1

Inhibitory Activity of Compounds

| | CETP IC$_{50}$ (nM) | | | |
|---|---|---|---|---|
| Example # | TG = 101.35 mg/dL | TG = 374.5 mg/dL | TG = 868.45 mg/dL | TG = 1269.35 mg/dL |
| Example 8 | 88.39 | 51.88 | 44.54 | 61.44 |
| Example 49 | 22.06 | 42.68 | 37.06 | 46.43 |
| Example 53 | 48.68 | 49.77 | 54.43 | 92.3 |
| Example 17 | 114 | 62.75 | 40.15 | 29.62 |
| Example 19 | 71.87 | 116.5 | 212.5 | 540.1 |
| Example 57A | 300.7 | 154.7 | 91.68 | 29.44 |
| Example 57B | 669.3 | 1297 | 2304 | 2701 |
| Example 58 | 82.18 | 151.3 | 280 | 371.9 |
| Anacetrapib (Merck) | 23.95 | 52.48 | 156.8 | 1263 |

These data demonstrate that the compounds of the instant invention retain CETP inhibitory activity in plasma isolated from hypertriglyceridemic human subjects as opposed to Anacetrapib (currently developed by Merck). The data show that the IC$_{50}$ shift from normal triglyceridemic plasma to high triglyceridemic plasma is small compared to the corresponding IC$_{50}$ shift for Anacetrapib. IC$_{50}$ shift is defined as:

$$\text{IC}_{50} \text{ shift} = \frac{\text{IC}_{50} \text{ in plasma isolated from hypertriglyceridemic human plasma}}{\text{IC}_{50} \text{ in plasma isolated from normal triglyceridemic human plasma}}$$

The IC$_{50}$ shift for the compounds of Formula I are less than 5, less than 10, less than 20 or less than 30. Preferably the IC$_{50}$ shift for the compounds of the instant invention is less than 5.

(2) In Vivo Experiments
Animals and Experimental Conditions

Nine- to ten-week-old, male golden Syrian hamsters were purchased from Japan SLC Inc. (Shizuoka, Japan). Animals underwent a more than 1-week acclimation period under the following conditions: 8:00/20:00 light/dark cycle, room temperature 23±2° C. (range), 55±15% (range) humidity. During this time, animals received filtered (0.5 µm) water and a standard chow diet ad libitum.

To induce an acute increase in plasma triglyceride levels, Triton WR-1339 (Cat. No. 35418-12, Nacalai Tesque Inc, Kyoto, Japan) was dissolved in saline (Otsuka Normal Saline, Otsuka Pharmaceuticals, Tokushima, Japan) at a concentration of 2.5 to 10% (w/w), and was intravenously administered at a volume of 2 mL/kg from the basilic vein under isoflurane (FORANE®, Abbott Japan Co. Ltd., Tokyo, Japan) inhalant anesthesia. Whole blood samples were collected using a heparin-washed syringe (Heparin sodium injection "Ajinomoto"; Ajinomoto, Tokyo, Japan) from the abdominal vein by venipuncture under isoflurane (Abbott Japan Co. Ltd.) inhalant anesthesia. After centrifugation at 15,000 rpm for 10 min at 4° C., heparinized plasma was prepared and stored at −80° C. until use.

Compounds (CETP inhibitors) were suspended in 0.5% methyl cellulose (Methyl cellulose 400 cP, Cat. No. 138-05072, Wako Pure Chemical Industries, Osaka, Japan) solution, which was used as a vehicle. Compound or vehicle (10 mL/kg) was administered once by oral gavage 5 h before administration of Triton WR-1339.

Determination of Total Cholesterol and Triglyceride Concentrations in Plasma

Cholesterol and triglyceride concentrations in plasma and serum were measured manually with kits (Cholesterol E-test, Cat. No. 439-17501, and Triglyceride E-test, Cat. No. 432-40201, Wako Pure Chemical, Osaka, Japan).

Ex Vivo CETP Activity in Plasma

Plasma CETP activity ex vivo was determined as followed: 50 µL of hamster plasma (final 80% plasma) was mixed with 10 µL of donor solution diluted with assay buffer composed of 50 mM Tris-HCl (pH7.4) containing 150 mM NaCl and 2 mM EDTA in a 96-well half area black flat bottom plate (Cat. No. 3686, Corning, Corning, N.Y.). Fluorescence intensity was measured every 15 min at an excitation wave length of 485 nm and an emission wavelength of 535 nm for 120 min at 37° C. using ARVO SX+L (PerkinElmer, Wellesley, Mass.). CETP activity (RFU/min) was defined as the change in fluorescence intensity from 30 to 90 min.

Plasma CETP Concentrations

Plasma CETP concentrations were measured using an enzyme-linked immunosolvent assay (ELISA) kit (Cat No. 278181, Daiichi Pure Chemicals, Tokyo, Japan). Recombinant human CETP protein was used as a standard. Hamster plasma was diluted 250-fold by the dilution buffer in the kit, and then CETP concentration was measured according to the manufacturer's protocol.

High Performance Liquid Chromatography (HPLC) System for Lipoprotein Analysis in Hamster Plasma An HPLC-size exclusion chromatography system with an on-line enzymatic dual detection system for lipids has been used for lipoprotein analysis. Plasma samples were diluted (5-fold) with saline after filtration (0.45 µm, Millipore Co, Cat. No. UFC30HV00) and injected into the HPLC system at a volume of 100 µL (as 20 µL of plasma), every 95 min, using an auto-sampler. Plasma lipoproteins were separated using a single Superose 6 column and filtered phosphate buffered saline (0.45 µm, Millipore Co., Bedford, Mass., Cat. No. SJHVM4710; PBS, Dainippon Pharmaceutical, Osaka, Japan Cat. No. 28-103-05 FN) at a flow rate of 0.5 mL/min. Each enzymatic reagent was pumped at a flow rate of 0.25 mL/min. Both enzymatic reactions proceeded at 37° C. in a reactor coil (Teflon tube, 15 m×0.4 mm id) in the column oven. The color developed after the enzyme reaction was measured at 580 nm, and the electric signal was monitored (every 0.5 second).

A control pooled EDTA-plasma sample was used to standardize the cholesterol and phospholipid levels in lipoproteins. Cholesterol and phospholipid levels in the control plasma were measured manually with kits (Cholesterol E-test, Cat. No. 439-17501, and Phospholipid C-test, Cat. No. 433-36201, respectively, Wako Pure Chemical Industries), and the concentrations were 121.8 and 216.8 mg/dL, respectively. Concentrations of VLDL, LDL, and HDL-cholesterol and -phospholipid levels were calculated using chromatogram areas observed for control hamster plasma samples. With this methodology, the retention times of control hamster VLDL, LDL, and HDL were 18.5-24.0, 24.0-30.5, and 31.5-42.0 min, respectively.

Data Analysis

Data are expressed as mean and standard error of the mean (SEM). To assess statistical significance for the multiple groups, Dunnett's multiple comparisons test was used, after one-way analysis of variance (ANOVA). Student's t test was used for statistical analysis between two groups. Statistical significance was defined as $P<0.05$.

Acute Hypertriglyceridemia in Hamsters

In order to determine the effects of acute changes in plasma triglyceride levels on CETP activity in vivo, Triton WR-1339 was injected intravenously to hamsters fed a standard chow diet. Triton WR-1339 increases plasma triglyceride levels via inhibition of the lipoprotein lipase pathway and, in turn, VLDL lipolysis (Borensztajn, Rone, and Kotlar, "The inhibition in vivo of lipoprotein lipase (clearing-factor lipase) activity by triton WR-1339", Biochem J. 1976; 156:539-543).

The intravenous administration of Triton WR-1339 at doses of 50, 100, or 200 mg/kg resulted in dose-dependent increases of plasma triglyceride levels compared to the saline-treated group. The maximum increase in triglyceride levels was observed 8 hours after administration of Triton. Consistent with the increase in triglyceride levels, plasma CETP activity also increased dose-dependently. Based on these results, pharmacodynamic parameters were determined 3 h after administration of Triton WR-1339 in subsequent studies.

3 h after administration, Triton WR-1339 at doses of 50 and 100 mg/kg increased plasma concentrations of triglycerides (2.0 and 4.0-fold), total cholesterol (1.2 and 1.4-fold) and CETP activity (1.7 and 3.7-fold) with statistical significance. The increase in CETP activity was associated more with the change in triglyceride levels than the change in total cholesterol levels. Interestingly, Triton WR-1339 did not significantly affect plasma CETP concentrations at any dose, suggesting that the increase in CETP activity by Triton WR-1339 is due to the acute increase of acceptor in the cholesterol transfer process, but not due to the increase in the production of CETP protein.

The effect of intravenous administration of Triton WR-1339 on the plasma lipoprotein profile was determined by HPLC analysis. Compared to the saline group, Triton WR-1339 increased the cholesterol content of VLDL and increased VLDL particle size. Notably, HDL-cholesterol was not changed by 50 mg/kg treatment, but was reduced in the 100 mg/kg group. LDL-cholesterol was reduced by the administration of Triton WR-1339. These results suggest that Triton WR-1339 treatment increased CETP activity primarily by increasing triglyceride-rich particles.

Effect of Treatment with Triton WR-1339 on the Inhibition of CETP Activity by Torcetrapib The effect of an acute increase of plasma triglycerides in vivo (acute increase in triglyceride-rich particles) on the ability of Torcetrapib to alter plasma CETP activity, triglyceride and total cholesterol levels was investigated. Torcetrapib at doses of 3, 10 or 30 mg/kg or vehicle was administered once by gavage to hamsters fed a standard chow diet. Triton WR-1339 (50 or 100 mg/kg) or saline was injected intravenously 5 h after the administration of torcetrapib. Plasma parameters were measured 3 h after the injection of Trion WR-1339.

Torcetrapib dose-dependently, and significantly, inhibited plasma CETP activity in the saline group. The inhibitory effects at doses of 3, 10 and 30 mg/kg were 38, 74, and 88%, respectively. Relative to the saline group, the ability of Torcetrapib to inhibit CETP activity was decreased in animals treated with WR-1339. Differences between the saline and W-1339 groups in the extent of inhibition observed with doses of 3, 10, and 30 mg/kg of Torcetrapib were 5.5%, 13%, 35% ($P<0.01$), respectively. Moreover, the inhibitory effect of Torcetrapib at a dose of 10 mg/kg was decreased by treatment with Triton WR-1339. Relative to the saline group (74% inhibition), the extent of inhibition was reduced by 44 and 13% at the 50 and 100 mg/kg doses, respectively.

The effect of Torcetrapib on plasma triglyceride and total cholesterol levels in the saline and Triton WR-1339 groups was also determined. Torcetrapib treatment slightly, but significantly, lowered plasma triglyceride levels in the saline group at the 3 and 30 mg/kg doses. On the other hand, Torcetrapib did not affect plasma triglycerides in the Triton WR-1339 treatment groups. Total cholesterol levels were not changed by treatment with Torcetrapib in either the saline or Triton WR-1339 groups.

Based on these results, the 100 mg/kg dose of Triton WR-1339 was selected for further comparative studies of CETP inhibitors.

Effect of Triton WR-1339 on the Inhibition of CETP Activity Caused by Anacetrapib, Compound of Example 49 and Compound of Example 8

The effect of an acute increase of plasma triglycerides in vivo on the extent of CETP inhibition caused by Torcetrapib, Anacetrapib, compound of Example 49 or compound of Example 8 were investigated. Compound or vehicle was administered once by gavage to hamsters fed a standard chow diet. Triton WR-1339 (100 mg/kg) or saline was injected intravenously 5 h after administration of compound. Plasma parameters were measured 3 h after injection of Trion WR-1339. Two doses for each inhibitor were selected: around 55-75% (lower dose) or 75-80% (higher dose) inhibition in CETP activity in the saline group.

In the lower dose group, Torcetrapib (5 mg/kg), Anacetrapib (1.5 mg/kg), compound of Example 49 (1.5 mg/kg) and compound of Example 8 (0.75 mg/kg) significantly inhibited CETP activity by 60, 56, 63, and 72% in the saline group, respectively. Triton WR-1339 reduced the inhibitory effects of all compounds up to 13, 8, 26, and 20%, respectively, without statistical significance relative to the vehicle group.

In contrast to the lower dose group, In the higher dose group, Torcetrapib (10 mg/kg), Anacetrapib (3 mg/kg), compound of Example 49 (3 mg/kg) and compound of Example 8 (1.5 mg/kg) significantly inhibited CETP activity by 75, 78, 77, and 79% in the saline group, respectively. Triton WR-1339 markedly reduced the inhibitory effects of torcetrapib and anacetrapib in CETP activity up to 8 and 13%, respectively, without statistical significance relative to the vehicle group. However, compound of Example 49 and compound of Example 8 significantly inhibited CETP activity by 38 and 47%, with the administration of Triton WR-1339 modestly reducing their inhibitory effects.

These results suggest that the inhibition of CETP activity by Torcetrapib and Anacetrapib, even at higher doses, was decreased by the acute increase of plasma triglycerides in hamsters treated with Triton-WR-1339. Compared with Torcetrapib and Anacetrapib, hypertriglyceridemia had less of an effect on the potency of compound of Example 49 and compound of Example 8 in terms of CETP inhibition.

To determine maximum inhibition, in the ex vivo assay, Torcetrapib or compound of example 49 was exogenously added (because the difference in assay condition was in between in vitro (50% plasma) and ex vivo (80% plasma) plasma CETP activity assay. Both compounds at the concentration of 10 µM inhibited by almost 100% in the saline group. In the Triton WR-1339 group, compound of Example 49 inhibited by almost 100% but the inhibition by Torcetrapib was around 75%. These results suggested that the selective CETP inhibition by compounds in the in vivo study is likely due to the other mechanism but not due to the compound dependent decreased inhibition of CETP activity.

Additionally, in vivo experiments were conducted in order to assess the exposure and efficacy of Example 8 and Anacetrapib (Merck) in normal monkeys fed a high carbohydrate diet.

Animals and Diet

Normal male cynomolgus monkeys (n=17) weighing between 8-14 kg are placed on a high-carbohydrate, low-fat diet. The caloric composition of the diet is approximately 13.4% protein, 79.1% carbohydrate (sugar to starch ratio 50:50) and 7.5% fat. Calories are derived from standard monkey chow (LabDiet® 5047, PMI, Richmond, Ind. or LabDiet® 5000, Balanced Fiber diet, PMI, Richmond, Ind.) in quantities necessary to meet the protein and fat requirements, with the remaining calories provided by sugar-sweetened cereals, candies, and fruit (banana, orange, cantaloupe, honeydew, pineapple). The high-carbohydrate (CHO) diet will be fed for 18 days (4 days of pre-drug diet, 14 days of drug treatment), after which time they will return to their regular chow diets for a 14 day washout period followed by a second 14 day dosing phase of the study (normal diet).

| Compound | Dose Level (mg/kg) | Number of animals |
|---|---|---|
| Example 8 | 3 | n = 9 |
| Anacetrapib | 10 | n = 8 |

Assignment of compound treatment groups will be based on triglyceride responses to the 3 days on the high carbohydrate diet. Animals will act as their own control during the high CHO drug phase and the normal chow diet drug phase.

Compound Formulation

Compound of Example 8 is dissolved at 30 mg/mL in 1M NaOH+ethanol:maisoel glyceride:propylene glycol:cremophor RH40 (10:36:9:45) and diluted 1:10 in ddH2O. Anacetrapib is dissolved at 85 mg/mL in cremophor EL:Span80:Corn oil (1:1:1) and diluted to 10 mg/mL in ddH2O. The formulations are prepared each day (weekend doses are prepared on Friday) and stored stirring and protected from light at room temperature until dosing. Artificial flavor and color will be added to the dose when prepared.

Compound Administration

The animals will ingest the compounds (1 mL/kg) voluntarily from a plastic syringe offered at their home cage at approximately 8 am daily. Animals will be fed 60 minutes after the dose is administered.

Blood Collection

Blood collection will take place weekly during each dosing phase. Animals are fasted overnight (approximately 16 hours) prior to blood collection. Blood samples are collected from a saphenous vein via needle and syringe and put into 2 mL EDTA-coated tubes that are immediately placed on ice until centrifugation. Samples are centrifuged at 3,000 rpm for 20 minutes. The plasma is collected, divided into aliquots (listed below), and stored at −70° C. until analysis.

Sample Distribution

| | |
|---|---|
| 100 µl Plasma drug concentration | 150 µl FPLC |
| 100 µl TG, apoA-I, apoB (Chad) | 100 µl Extra plasma (×2 or 3) |
| 100 µl TC, HDL-C, LDL-C, TG (Dan) | 100 µl CETP activity |

Body Weights

Non-fed body weights (BW) will be measured and recorded once per week by Lab Animal Services.

The results are summarized in table 2 below:

TABLE 2

| | Example 8 | | Anacetrapib | |
|---|---|---|---|---|
| | Chow (n = 9) | High CHO (n = 7) | Chow (n = 8) | High CHO (n = 8) |
| | Plasma [drug] ng/mL | | | |
| Day 7 | 983 ± 408 | 1706 ± 949 | 272 ± 74 | 1836 ± 3694 |
| Day 14 | 1015 ± 398 | 1709 ± 800 | 320 ± 93 | 1437 ± 2935 |
| | CETP activity % Δ vs day 0 | | | |
| Day 7 | −78 ± 7 | −72 ± 7 | −62 ± 15 | −33 ± 23 |
| Day 14 | −73 ± 9 | −66 ± 10 | −59 ± 19 | −24 ± 22 |
| | HDL-C % Δ vs day 0 | | | |
| Day 7 | 144 ± 57 | 210 ± 24 | 141 ± 45 | 172 ± 34 |
| Day 14 | 142 ± 33 | 241 ± 29 | 136 ± 28 | 184 ± 45 |

The results are expressed by mean ± SD (Standard deviation).

The results indicate that in monkeys with diet-induced hypertriglyceridemia (TG>500 mg/dL), compound of example 8 retains CEPT inhibitory activity, and showed a greater maximal inhibition of CETP activity when compared to Anacetrapib.

In conclusion, in vivo and in vitro data have shown that the compounds of the invention retain inhibitory activity as opposed to other CETP inhibitors (anacetrapib and torcetrapib) compound currently or previously being developed.

Clinical Experiment:

In the initial proof of concept (PoC) study, subjects with mixed dyslipidemia and severe hypertriglyceridemia, no history of acute coronary syndrome (ACS), coronary artery disease (CAD), myocardial infarction (MI), or stroke are enrolled. The fasting lipid parameters in these patients are to meet the following criteria: LDL-C 100-150 mg/dL, HDL-C<40 mg/dL, TG>500 mg/dL. The PoC study is planned as a randomized, double-blind, placebo-controlled 2-period crossover design (14 days treatment in each period and 14 days washout in between) to assess pharmacokinetics and pharmacodynamics parameters in hypertriglyceridemic (TG>500 mg/dL) patients along with concomitant ambulatory blood pressure monitoring (ABPM) to assess effects on blood pressure, plasma aldosterone and cortisol concentrations.

After treatment with a CETP inhibitor of Formula I, the lipid parameters will be determined for patients with normal fasting triglyceride level and for people with high fasting triglyceride level and will be compared. Based on in vitro and in vivo data presented herein, the pharmacodynamic effect of compounds of Formula I in high or severely high triglyceride patients are expected to be similar in CETP inhibition and HDL increase than in patients with normal triglycerides level.

The study is aimed to demonstrate the retained CETP inhibitory efficacy of the compounds of Formula I in high triglyceride patients as well as safety (absence of increased blood pressure or aldosterone) in the targeted patient population. Retained CETP inhibitory efficacy can be defined as the ability of a compound of Formula I to maintain ≥50%, preferably ≥65%, or more preferably more ≥75% inhibition of CETP inhibitory activity in subjects with high plasma triglycerides when compared to subject with normal plasma triglycerides. In a preferred embodiment, retained CETP inhibitory efficacy can be defined as the ability of a compound of Formula I to maintain ≥50%, preferably ≥65%, or more preferably more ≥75% inhibition of CETP inhibitory activity without the need for dose escalation, in subjects with high plasma triglycerides when compared to subject with normal plasma triglycerides. The study is also aimed to demonstrate that the compound of Formula I increase HDL-C level by 80%, 90% or 100% in patients with high triglyceride level (>300 mg/dL) and most preferably in patients with very high triglyceride levels (>750 mg/dL).

A subject with an elevated triglyceride level includes a patient for which the fasting serum triglyceride level is higher than 150 mg/dL (milligrams per deciliter). High and very high fasting triglyceride levels are defined as ≥200 mg/dL and ≥500 mg/dL, respectively.

Current designations for fasting triglyceride levels according to the NCEP (National Cholesterol Education Program) are as follows: 150 to 199 mg/dL is borderline high; 200-499 mg/dL is high and ≥500 mg/dL is considered very high (Triglyceride and cardiovascular diseases, Journal of the American Heart Association, *Circulation,* 2011, 123, 2293-2333.)

A subject with high triglyceride levels includes a patient for which fasting serum triglyceride level is higher than 150 mg/dL (milligrams per deciliter). In one embodiment, the subject with high triglyceride levels include patient for which fasting triglyceride level is higher than 200 mg/dL, or higher than 300 mg/dL, or higher than 750 mg/dL.

Patient Population:

Evidence from epidemiological and controlled clinical trials have demonstrated that triglyceride levels are markedly affected by body weight status and body fat distribution, Ford ES, Li C, Zhao G, Pearson W S, Mokdad A H. Hyperglyceridemia and its pharmacologic treatment among US adults. *Arch Intern Med.* 2009; 169: 572-578. In This study, it was demonstrated that 80% of the participants classified as overweight (BMI 25 to 30 Kg/m$^2$) and obese (BMI>30 Kg/m$^2$) had triglyceride levels over 150 mg/dL, and with a cut point of triglyceride level >200 mg/dL, 83% of participants were classified as overweight.

Hypertriglyceridemia is seen in many patients with lipodystrophic disorders, a rare genetic disorder, often in association with low HDL-C (Simha V, Gard A. Lipodystrophy: lessons in lipid and energy metabolism. *Curr Opin Lipidol.* 2006; 17:162-169).

High triglyceride levels also are known to accompany either normal or impaired fasting glucose. 35% of type 2 Diabetes Mellitus adults have fasting triglyceride levels >200 mg/dL associated with a decreased HDL-C (Resnick H E, Foster G L, Bardsley J, Ratner R E. Achievement of American Diabetes Association clinical practice recommendations among US adults with diabetes, 1999-2002: The National Health and Nutrition Examination Survey. *Diabetes Care,* 2006; 29:531-537). Patients with poorly controlled type 1 diabetes Mellitus may exhibit a similar pattern of dylipidemia. Causes of hypertriglyceridemia in Diabetes Mellitus patients, include increased hepatic VLDL (very low density lipoprotein) production and defective removal of chylomicrons and CMR (chylomicron remnant) (Kreisberg R A. Diabetic dyslipidemia *Am. J. Cardiol.* 1998; 82:67U-73U).

Elevated triglyceride levels, along with increased waist circumference, elevated fasting glucose, elevated blood pressure, or reduced HDL-C levels, are known to be metabolic syndrome risk factors (Ninomiya J K, L'Italien G, Criqui M H, Whyte J L, Gamst A, Chen R S. Association of the metabolic syndrome with history of myocardial infarction and stroke in the third national health and nutrition examination Survey. *Circulation.* 2004; 109:42-46). The prevalence of elevated triglyceride levels is nearly twice as high in subjects with metabolic syndrome as in those without metabolic syndrome (Schwartz G G, Olson A G, Szarek M, Sasiela W J. Relation of characteristics of metabolic syndrome to short-term prognosis and effects of intensive statin therapy after acute coronary syndrome: and analysis of the myocardial ischemia reduction with aggressive cholesterol lowering (MIRACL) trial. *Diabetes Care.* 2005; 28: 2508-2513). Among individuals with components of metabolic syndrome, high triglyceride levels was the second most common after elevated blood pressure. (Kasai T, Miyauchi K, Kurata T, Ohta H, Okazaki S, Miyazaki T, Kajimoto K, Kubota N, Daida H. Prognostic value of the metabolic syndrome for long-term outcomes in patients undergoing percutaneous coronary intervention *Circ. J.* 2006; 70:1531-1537).

Markedly elevated triglyceride levels are also seen in patients with genetic syndromes of triglyceride metabolism. These genetic syndromes includes chylomicronemia syndrome due to a deficiency of lipoprotein lipase, or due to a deficiency of apolipoprotein C-II or due to APOA5 and GP1 HBP1 loss-of-function mutations. (Brunzell J D. Familial lipoprotein lipase deficiency and other causes of chylomicronemia syndrome. In: Scriver C R et al. The metabolic and molecular base of inherited diseases. New York, N.Y.: McGraw-Hill; 1995; 1913-1932; Priore Oliva C. et al. inherited apolipoprotein A-V deficiency in severe hypertriglyceridemia. *Arterioscler Thromb Vasc Biol.* 2005; 25:411-417; Olivecrona G et al. Mutation of conserved cysteines in Ly6 domain of GPIHBP1 in familial chylomicronemia. *J. Lipid Res.* 2010; 51:1535-1545; Beigneux A P et al. Chylmicronemia with a mutant GPIHBP1 (Q115P) which can not bind lipoprotein lipase. *Arterioscler Thromb Vasc. Biol.* 2009; 29:956-962) Additional genetic syndromes associated with hypertriglyceridemia include familial hypertriglyceridemia, familial combined hyperlipdidemia or type III dysbetalipoproteninemia. (Goldstein J L et al. genetic analysis of lipid levels in 176 families and delineation of a new inherited disorder, combined hyperlipidemia. *J. Clin. Invest.* 1973; 52: 1544-1568; Brunzell J D et al. Myocardial infraction in the familial forms of hypertriglyceridemia. *Metabolism.* 1976; 25: 313-320)

Therefore, subject with high triglyceride levels may include patient with familial chylomicronemia syndrome due to a deficiency of lipoprotein lipase, or due to a deficiency of apolipoprotein C-II or due to APOA5 and GP1 HBP1 loss-of-function mutations, patients with coronary artery diseases, patient with acute coronary syndrome, patients with myocardial infraction, patients with diabetes, patients with obesity, patients with lypodystrophic disorders, patients with chronic kidney disease, patients with metabolic syndrome, patients with other genetic syndromes that usually require an acquired cause to raise triglyceride such as familial hypertriglyceridemia, familial combined hyperlipdidemia or type III dysbetalipoproteninemia.

The compound for use in the present invention may be administered either simultaneously with, or before or after, one or more other therapeutic agent. The compound of the present invention may be administered separately, by the same or different route of administration, or together in the same pharmaceutical composition as the other agents.

In one embodiment, the invention pertains to the method or use according to anyone of embodiments 1 to 34A, comprising administering to the subject a product comprising a compound according to anyone of formulae I to VIIA or a pharmaceutically acceptable salt thereof, and at least one other therapeutic agent as a combined preparation for simultaneous, separate or sequential use in therapy.

Products provided as a combined preparation for use in the method of the invention, include a composition comprising the compound according to anyone of formulae I to VIIA, or a pharmaceutically acceptable salt thereof, and the other therapeutic agent(s) together in the same pharmaceutical composition, or the compound according to anyone of formulae I to VIIA, or a pharmaceutically acceptable salt thereof, and the other therapeutic agent(s) in separate form, e.g. in the form of a kit.

In one embodiment, the invention pertains to the method or use according to anyone of embodiments 1 to 34A, comprising administering to the subject a pharmaceutical composition comprising a compound according to anyone of formulae I to VIIA, or a pharmaceutically acceptable salt thereof, and at least one other therapeutic agent as a combined preparation for simultaneous, separate or sequential use in therapy. Optionally, the pharmaceutical composition for use in the method of the invention may comprise a pharmaceutically acceptable excipient, as described above.

In one embodiment, the invention provides a kit for use in the method of the invention, comprising two or more separate pharmaceutical compositions, at least one of which contains a compound according to anyone of formulae I to VIIA, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic agent may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the method or use according to anyone of embodiments 1 to 34A, comprising administering a compound according to anyone of formulae I to VIIA, or a pharmaceutically acceptable salt thereof, wherein the medicament is prepared for administration with another therapeutic agent.

The invention also provides a compound according to anyone of formulae I to VIIA, or a pharmaceutically acceptable salt thereof, for use in the method of the invention, wherein the compound according to anyone of formulae I to VIIA, or a pharmaceutically acceptable salt thereof, is prepared for administration with another therapeutic agent. The invention also provides another therapeutic agent for use in the method of the invention, wherein the other therapeutic agent is prepared for administration with a compound according to anyone of formulae I to VIIA, or a pharmaceutically acceptable salt thereof.

The invention also provides the use of a compound according to anyone of formulae I to VIIA, or a pharmaceutically acceptable salt thereof, for treatment, prevention and/or amelioration of atherosclerosis or dyslipidemia, or for raising HDL-C and/or lowering LDL-C, in a subject with high triglyceride level, wherein the patient has previously (e.g. within 24 hours) been treated with another therapeutic agent. The invention also provides the use of another therapeutic agent treatment, prevention and/or amelioration of atherosclerosis or dislipedemia, or for raising HDL-C and/or lowering LDL-C in a patient with high triglycerides level, wherein the patient has previously (e.g. within 24 hours) been treated with a compound according to anyone of formulae I to VIIA, or a pharmaceutically acceptable salt thereof.

In one embodiment, the other therapeutic agent is selected from: statin, cholesterol absorption inhibitor, apoA-1 up-regulator/inducer, pre-beta HDL mimetic, ABCA1 stabilizer or inducer, LXR agonist, FXR agonist, phospholipid transfer protein (PLTP) inhibitor, aldosterone synthase inhibitor (ASI), fibric acid derivative, fish oil, DGAT1 inhibitor and endothelial lipase inhibitor.

The term "in combination with" a second agent or treatment includes co-administration of the compound of the invention (e.g., a compound according to anyone of Formulae I to VIIA or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of atherosclerosis or dyslipidemia.

Examples of second agents include:
i). statin (also known as HMG-CoA reductase inhibitor);
ii) cholesterol absorption inhibitor;
iii) apoA-1 up-regulator/inducer;
iv) pre-beta HDL mimetic;
v) ABCA1 stabilizer or inducer;
vi) LXR agonist;
vii) FXR agonist;
viii) phospholipid transfer protein (PLTP) inhibitor;
ix) aldosterone synthase inhibitor;
x) fibric acid derivative;
xi) fish oil;
xii) DGAT1 inhibitor;
xiii) endothelial lipase inhibitor;
or a pharmaceutically acceptable salt thereof.

i) Statins (or HMG-CoA reductase inhibitors) are a class of drugs used to lower cholesterol levels by inhibiting the enzyme HMG-CoA reductase, which plays a central role in the production of cholesterol in the liver. Increased cholesterol levels have been associated with cardiovascular diseases and statins are therefore used in the prevention of these diseases. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

ii) Cholesterol absorption inhibitors are a class of compounds that prevents the uptake of cholesterol from the small intestine into the circulatory system, and, in turn, reduce plasma LDL-C concentrations Increased cholesterol levels are associated with increased CVD risk; thus, cholesterol absorption inhibitors are used with the goal of reducing CVD risk. An example of a cholesterol absorption inhibitor is Ezetimibe, previously known as "Sch-58235". Another example is Sch-48461. Both compounds are developed by Schering-Plough.

iii) Apolipoprotein A-I is a protein that in humans is encoded by the APOA1 gene. It has a specific role in lipid metabolism. Apolipoprotein A-I is the major protein component of high density lipoprotein (HDL) in plasma. Chylomicrons secreted from the intestinal enterocyte also contain ApoA1 but it is quickly transferred to HDL in the bloodstream. The protein promotes cholesterol efflux from tissues to the liver for excretion. It is a cofactor for lecithin cholesterolacyltransferase (LCAT) which is responsible for the formation of most plasma cholesteryl esters. Infusion of a variant of apoA-I in humans has been shown to regress atherosclerotic plaque, as assessed by intravascular ultrasound; thus, apoA-I reduces CVD risk and has the ability to both slow progression and induce regression of atherosclerosis. An example of an apoA-1 up-regulator/inducer is RVX208.

iv) An example of a pre-beta HDL mimetic is CER-001. CER-001 is an innovative complex of recombinant human ApoA-I, the major structural protein of HDL, and phospholipids. It has been designed to mimic the structure and function of natural, nascent HDL, also known as pre-beta HDL, which is believed to be protective against atherosclerosis. It is hoped that CER-001 will further reduce cardiovascular events in high-risk patients by promoting removal of cholesterol from the vessel wall.

v) ATP-binding cassette transporter ABCA1 (member 1 of human transporter sub-family ABCA), also known as the cholesterol efflux regulatory protein (CERP) is a protein which in humans is encoded by the ABCA1 gene. This transporter is a major regulator of cellular cholesterol and phospholipid homeostasis. An example of ABCA1 regulator is Probucol. Probucol lowers the level of cholesterol in the bloodstream by increasing the rate of LDL catabolism. Additionally, probucol may inhibit cholesterol synthesis and delay cholesterol absorption. Probucol is a powerful antioxidant which inhibits the oxidation of cholesterol in LDLs; this slows the formation of foam cells, which contribute to atherosclerotic plaques.

vi) The liver X receptor (LXR) is a member of the nuclear receptor family of transcription factors and is closely related to nuclear receptors such as PPAR, FXR and RXR. Liver X receptors (LXRs) are important regulators of cholesterol, fatty acids and glucose homeostasis. LXR agonists are effective for treatment of murine models of atherosclerosis, diabetes, anti-inflammation and Alzheimer's disease. Treatment with LXR agonists (hypocholamide, T0901317, GW3965, or N,N-dimethyl-3beta-hydroxy-cholenamide (DMHCA)) lowers the cholesterol level in serum and liver and inhibits the development of atherosclerosis in murine disease models. Examples of LXR agonists are GW3965 (a synthetic nonsteroidal liver X receptor (LXR) agonist/activator) and T0901317 (a dual LXR, FXR agonist).

vii) The farnesoid X receptor (FXR), also known as NR1H4 (nuclear receptor subfamily 1, group H, member 4) is a nuclear hormone receptor with activity similar to that seen in other steroid receptors such as estrogen or progesterone but more similar in form to PPAR, LXR and RXR. Activation of the nuclear receptor FXR is known to improve hyperglycemia and hyperlipidemia. An example of FXR agonist is GW4064 (3-(2,6-Dichlorophenyl)-4-(3'-carboxy-2-chlorostilben-4-yl)oxymethyl-5-isopropylisoxazole).

viii) Phospholipid transfer protein (PLTP) is a protein that in humans is encoded by the PLTP gene. The protein encoded by this gene is one of at least two lipid transfer proteins found in human plasma, with CETP being the other The encoded protein transfers phospholipids from triglyceride-rich lipoproteins to high density lipoprotein (HDL). In addition to regulating the size of HDL particles, this protein may be involved in cholesterol metabolism. At least two transcript variants encoding different isoforms have been found for this gene. Because PLTP influences the metabolism of both triglyceride-rich lipoproteins and HDL, modulation of this transfer protein has the potential to alter cardiovascular disease risk.

ix) The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. The most preferred non-steroidal aldosterone synthase inhibitor is the (+)-enantiomer of the hydrochloride of fadrozole (U.S. Pat. Nos. 4,617,307 and 4,889,861) of formula

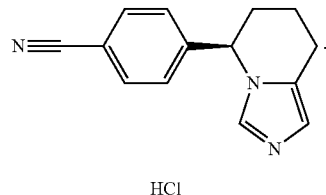 [SMILES: N#Cc1ccc([C@H]2CCCc3cncn32)cc1 ; Cl]

HCl or, if appropriable, a pharmaceutically acceptable salt thereof.

Aldosterone synthase inhibitors useful in said combination are compounds and analogs generically and specifically disclosed e.g. in US200710049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methyl-benzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluorobenzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US200710225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5,1-c][1,4] oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C, C, C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl(5-(1H-indol-5-yl)pyridin-3-yl)methyl)ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

x) fibric acid derivatives lower triglycerides and raise HDL cholesterol. They may have little effect on LDL cholesterol. For example, Gemfibrozil or fenofibrate is prescribed for people who have very high triglycerides or who have low HDL and high triglycerides. Gemfibrozil may be used to reduce the risk of heart attack in people with coronary artery disease (CAD) who have low HDL and high triglycerides.

xi) fish oil is an oil derived from the tissues of oily fish. Fish oils contain the omega-3 fatty acids eicosapentaenoic acid (EPA), and docosahexaenoic acid (DHA), precursors of eicosanoids that are known to have have many health benefits. Fish oil and other omega-3 sources are most highly recommended for the following conditions: hypertriglyceridemia, secondary cardiovascular disease and prevention of high blood pressure. For example, Lovaza is used along with a low-fat and low-cholesterol diet to lower very high triglycerides (fats) in your blood.

xii) DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol. Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggest that a DGAT1 inhibitor has utility for the treatment of obesity and obesity-associated complications. DGAT1 inhibitors useful in said combination are compounds and analogs generically and specifically disclosed e.g. in WO2007/126957 and WO2009/040410, in particular in the compound claims and the final products of the working examples, the subject-matter of the final products, the pharmaceutical preparations and the claims. Preferred DGAT1 inhibitors suitable for use in the present invention include, {4-[4-(3-Methoxy-5-phenylamino-pyridin-2-yl)-phenyl]-cyclohexyl}-acetic acid, (4-{4-[5-(1-Methyl-1H-pyrazol-3-ylamino)-pyridin-2-yl]-phenyl}-cyclohexyl)-acetic acid, (4-{4-[5-(5-Fluoro-6-methoxy-pyridin-3-ylamino)-pyridin-2-yl]-phenyl}-cyclohexyl)-acetic acid, (4-{5-[5-(6-Trifluoromethyl-pyridin-3-ylamino)-pyridin-2-yl]-spirocyclohexylidenyl-1,1'-indanyl}-acetic acid, (4-{4-[5-(Benzooxazol-2-ylamino)-pyridin-2-yl]-phenyl}-cyclohexyl)-acetic acid, 4-(4-{4-[2-(3-Chlorophenylamino)-oxazol-5-yl]-phenyl}-cyclohexyl)-butyric acid, (4-{4-[5-(6-Trifluoromethyl-pyridin-3-ylamino)-pyridin-2-yl]-phenyl}-cyclohexyl)-acetic acid, (6-{4-[4-(2H-Tetrazol-5-ylmethyl)-cyclohexyl]-phenyl}-pyridazin-3-yl)-(6-trifluoromethyl-pyridin-3-yl)-amine, 3-(4-{4-[6-(6-Trifluoromethyl-pyridin-3-ylamino)-pyridazin-3-yl]-phenyl}-cyclohexylmethyl)-4H-[1,2,4]oxadiazol-5-one, (1-{4-[6-(3-Trifluoromethyl-phenylamino)-pyridazin-3-yl]-phenyl}-piperidin-4-yl)-acetic acid, (4-{4-[4-Methyl-6-(6-trifluoromethyl-pyridin-3-ylamino)-pyridazin-3-yl]-phenyl}-cyclohexyl)-acetic acid, (4-{4-[5-(6-Trifluoromethyl-pyridin-3-ylamino)-pyrazin-2-yl]-phenyl}-cyclohexyl)-acetic acid, 6-[5-(4-Chloro-phenyl)-[1,3,4]oxadiazol-2-yl]-2-(2,6-dichloro-phenyl)-1H-benzoimidazole, 6-(5-Cyclohexyl-[1,3,4]oxadiazol-2-yl)-2-

(2,6-dichloro-phenyl)-1H-benzoimidazole, 6-(5-Butyl-[1,3,4]oxadiazol-2-yl)-2-(2,6-dichloro-phenyl)-1H-benzoimidazole, 2-(2,6-Dichloro-phenyl)-6-[5-(5-methyl-pyridin-3-yl)-[1,3,4]oxadiazol-2-yl]-1H-benzoimidazole, 6-[5-(4-Chloro-phenyl)-[1,3,4]oxadiazol-2-yl]-2-(2,6-dimethyl-4-morpholin-4-yl-phenyl)-1H-benzoimidazole, 6-[5-(4-Chloro-phenyl)-[1,3,4]oxadiazol-2-yl]-2-(3,5-dichloro-pyridin-4-yl)-1H-benzoimidazole, 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid, 3-(4-{6-[5-(4-Methoxy-phenyl)-[1,3,4]oxadiazol-2-yl]-1H-benzoimidazol-2-yl}-3,5-dimethyl-phenyl)-propionic acid, 3-(4-{6-[5-(4-methoxyphenylamino)-[1,3,4]oxadiazol-2-yl]-1H-benzimidazol-2-yl}-3,5-dimethylphenyl)-propionic acid, [3-(4-{6-[5-(4-Chloro-phenyl)-[1,3,4]oxadiazol-2-yl]-1H-benzoimidazol-2-yl]-3,5-dimethyl-phenyl)-propyl]-phosphonic acid, 2-(2,6-Dichloro-phenyl)-6-(4,5-diphenyl-oxazol-2-yl)-1H-benzoimidazole, (4-{6-[5-(4-Chloro-phenyl)-[1,3,4]oxadiazol-2-yl]-1H-benzoimidazol-2-yl}-3,5-dimethyl-phenoxy)-acetic acid, 2-(2,6-Dichloro-phenyl)-6-(5-pyrrolidin-1-yl-[1,3,4]oxadiazol-2-yl)-1H-benzoimidazole, and 3,5-Dimethyl-4-{6-[5-(4-trifluoromethyl-phenylamino)-[1,3,4]oxadiazol-2-yl]-1H-benzoimidazol-2-yl}-phenol.

xiii) Endothelial lipase (EL) activity has been implicated in HDL catabolism, vascular inflammation, and atherogenesis. EL knockout mice have a pronounced elevation in HDL cholesterol relative to wild type mice. Inhibitors are therefore expected to be useful for the treatment of cardiovascular disease.

Second agent of particular interest includes statin and cholesterol absorption inhibitor.

Exemplification of the Invention:

The following examples are intended to illustrate the invention and are not to be construed as being limitations thereon.

Exemplification of the Invention:

Examples 1-27 are Compounds Disclosed in US in US 2009/0118287 (WO 2009/059943)

1

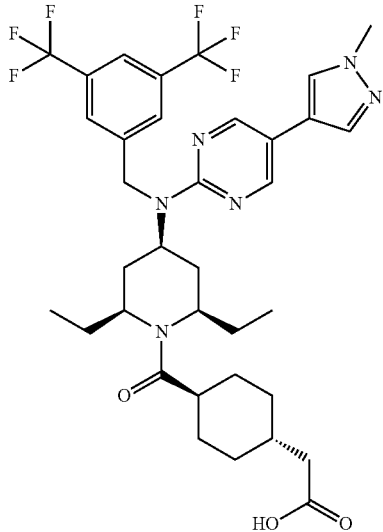

2

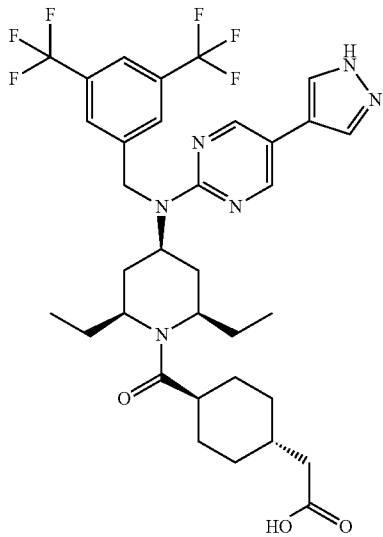

3

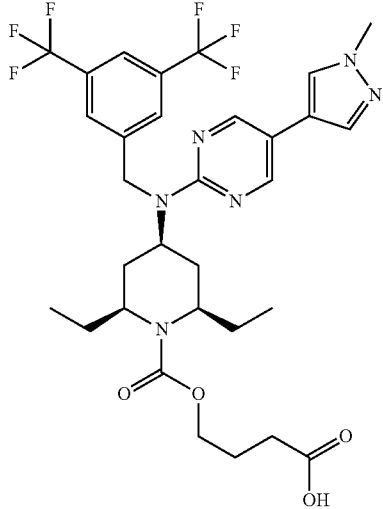

4

71
-continued
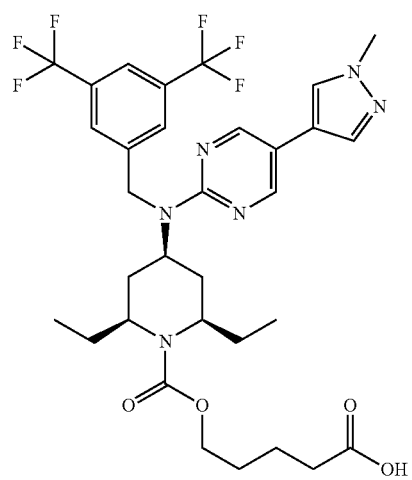
5
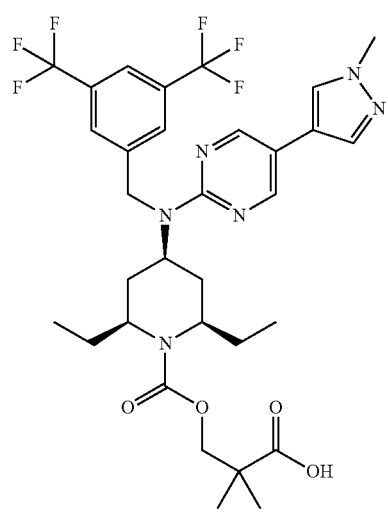
6
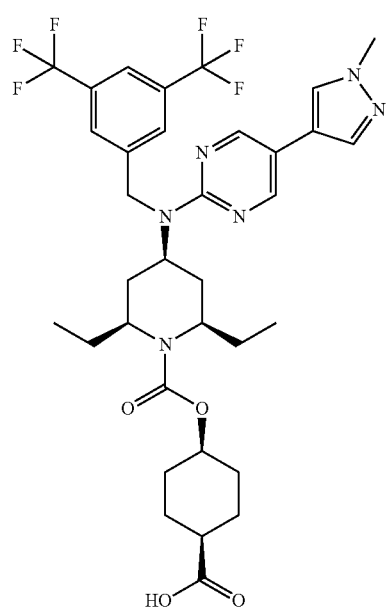
7
72
-continued
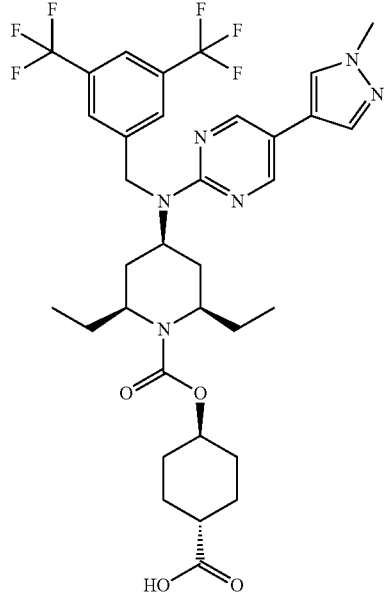
8
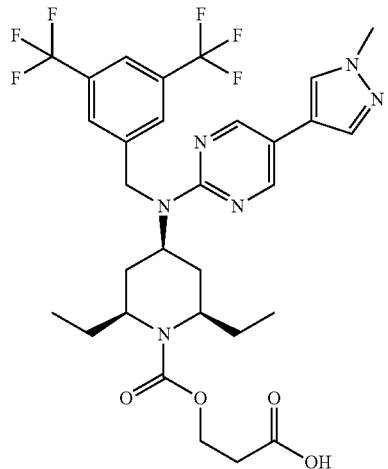
9
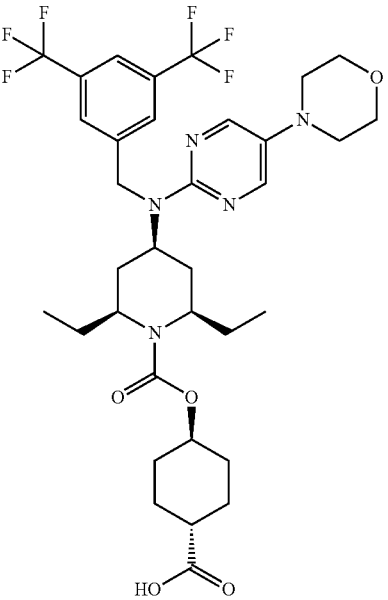
10

11
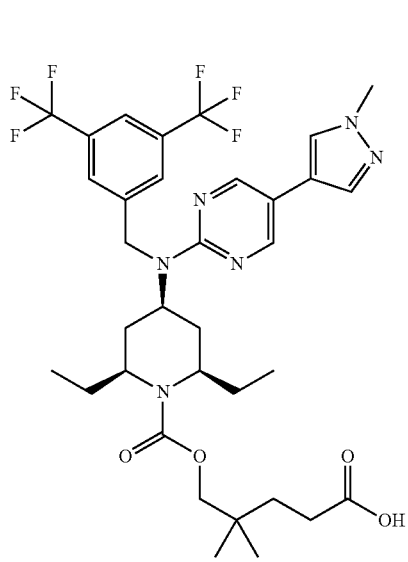
12
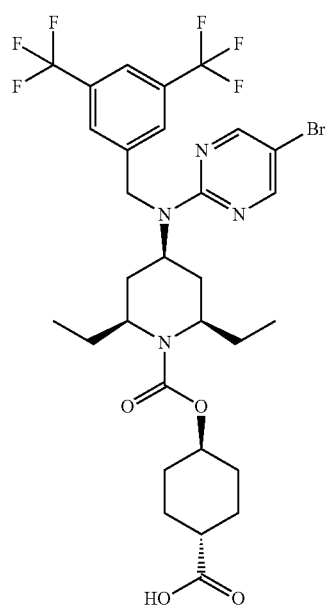
13
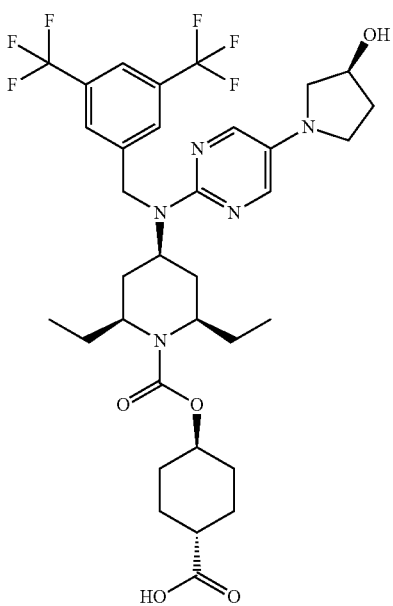
14
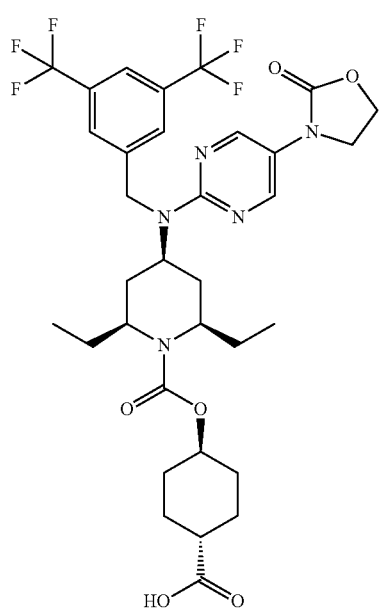

15
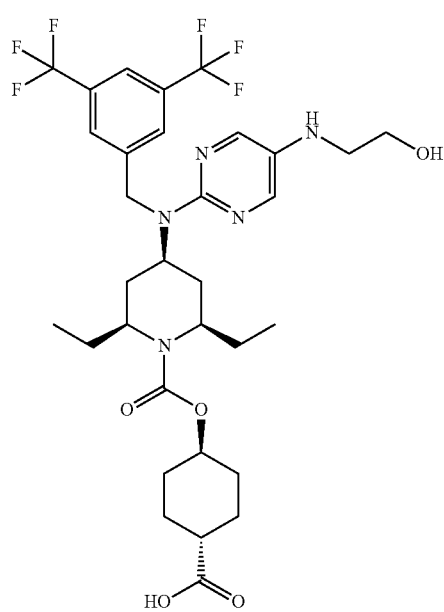
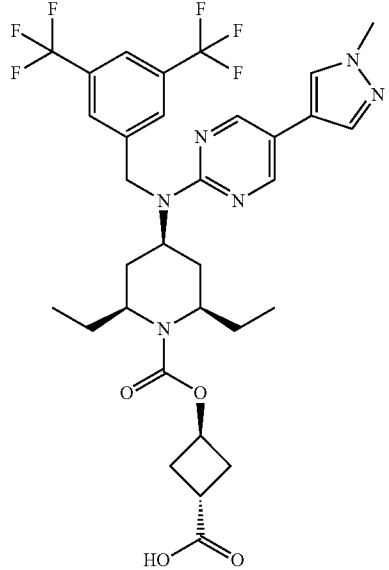
16
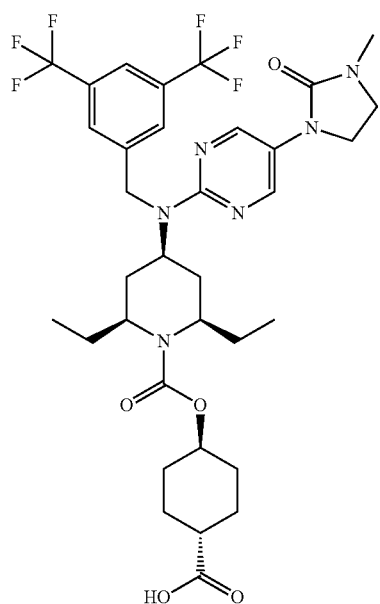
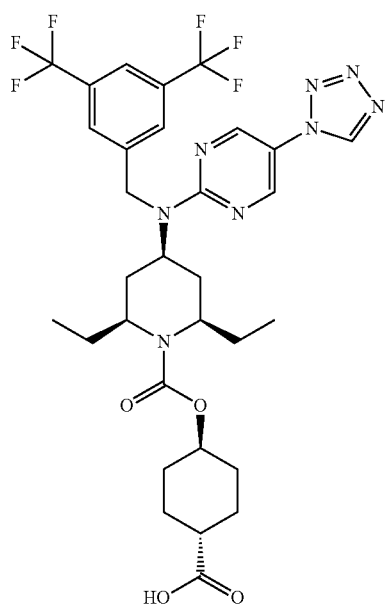

19
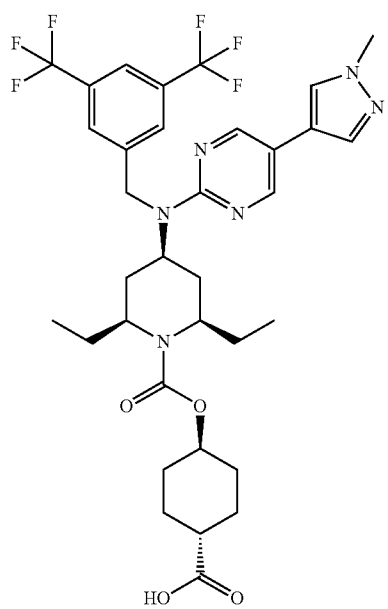
21
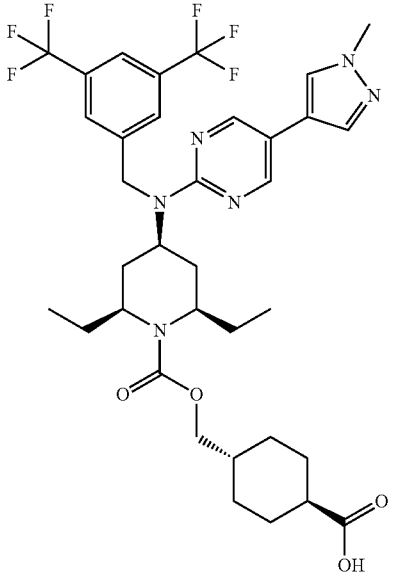
20
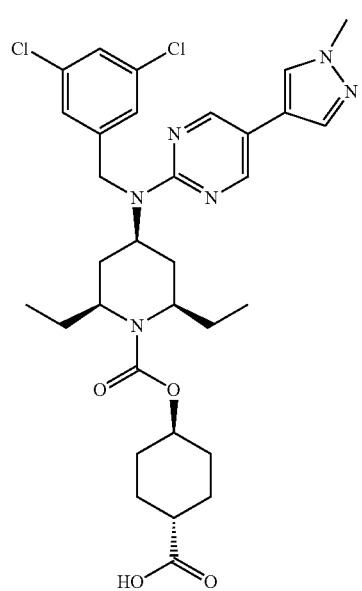
22
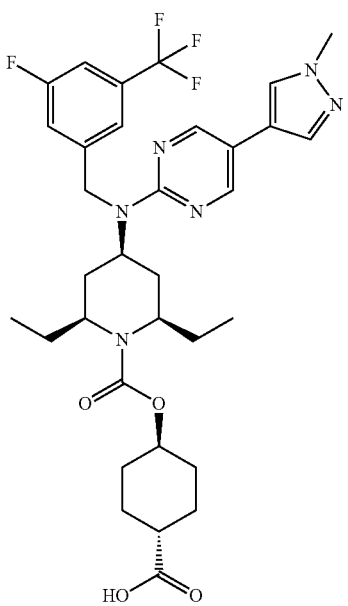

23
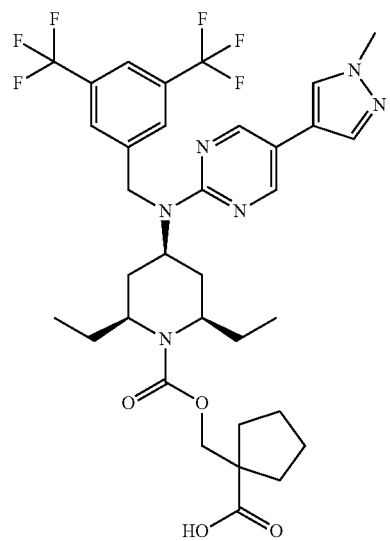
25
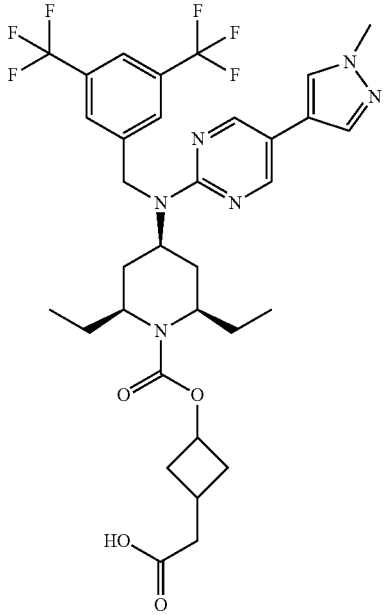
24
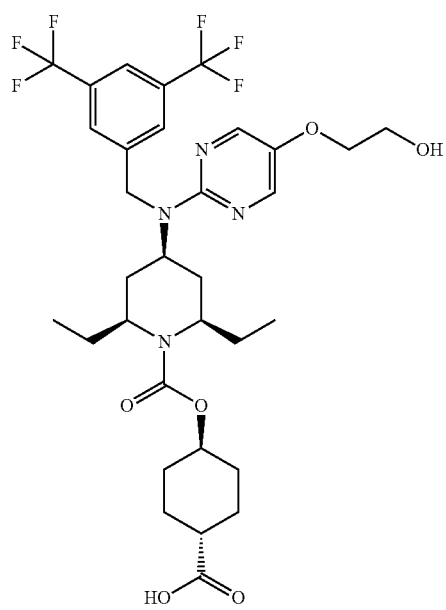
26
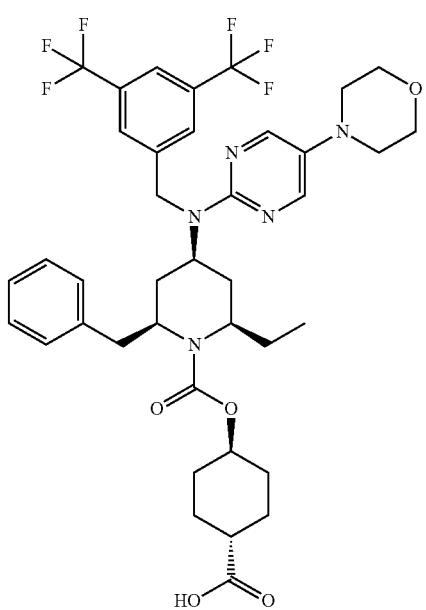

-continued
27
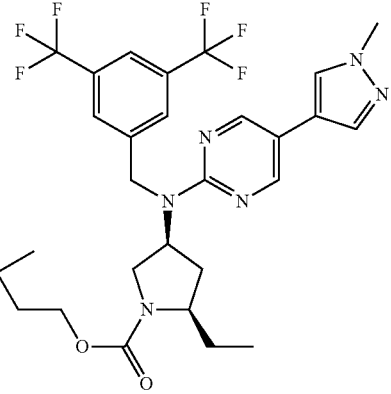
30
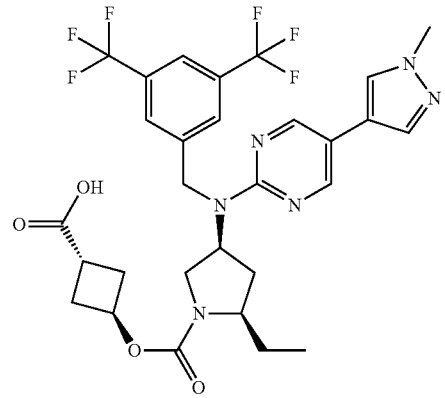
31
Examples 28-41 are Compounds Disclosed in US 2010/0311750 (WO 2009/071509)
28
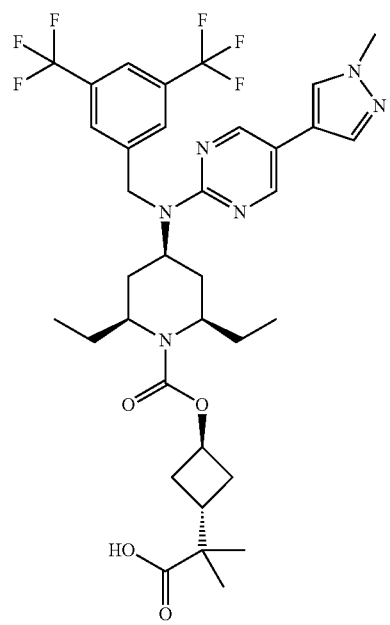
32
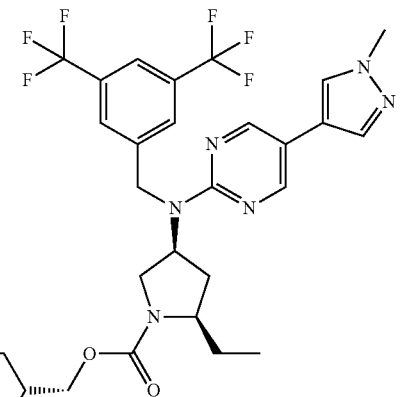
29
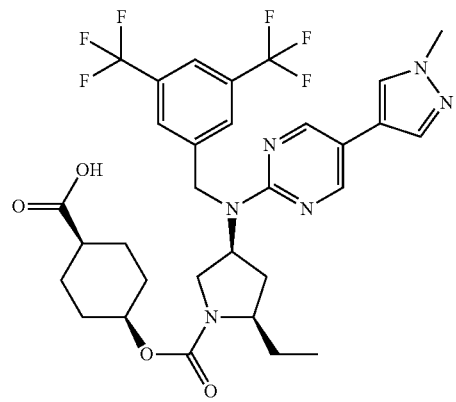
33
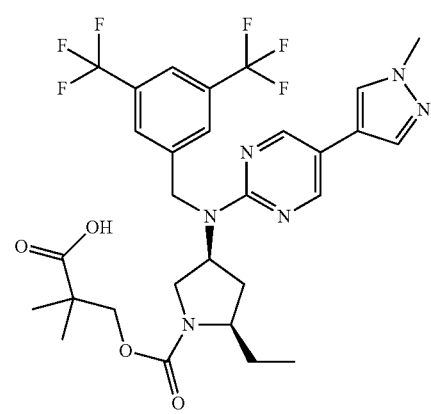

83
-continued
34
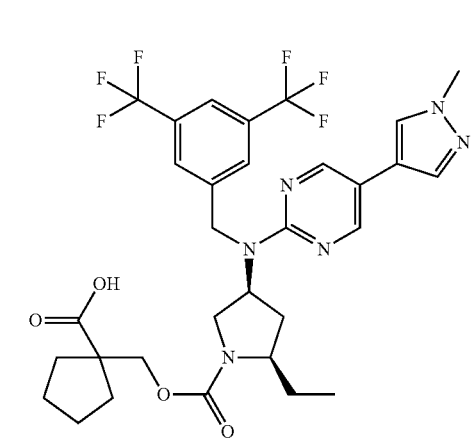
35
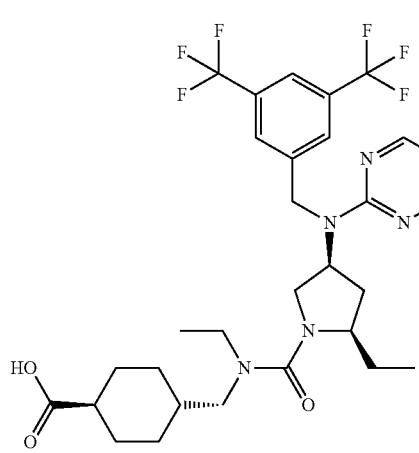
36
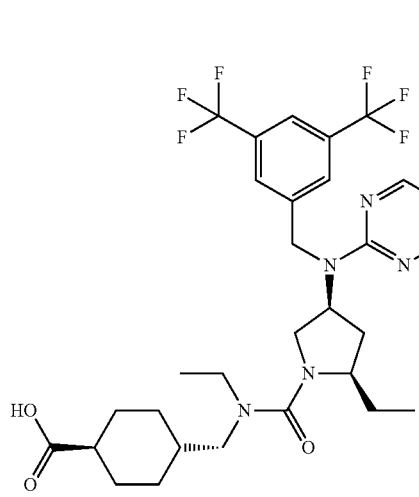
84
-continued
37
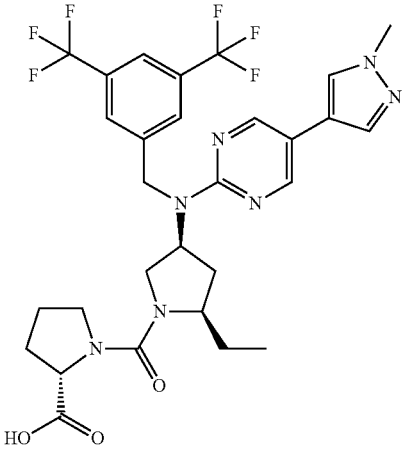
38
39
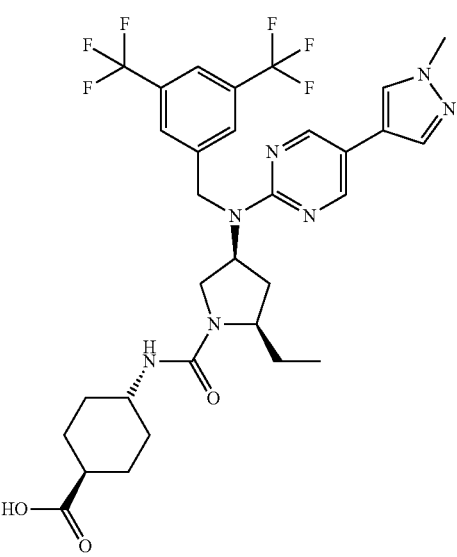

-continued
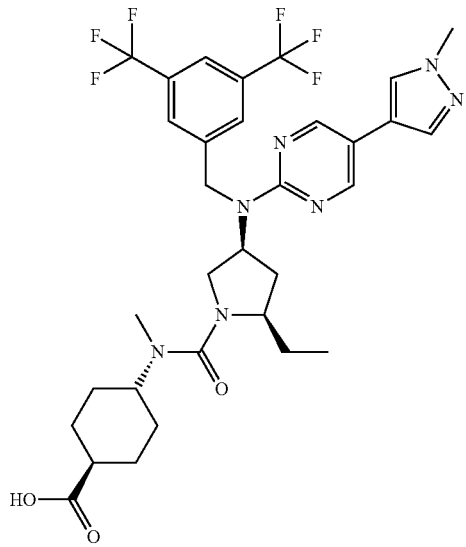
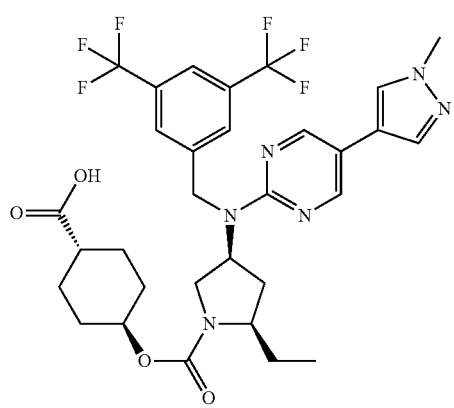
Examples 42-46 are Compounds Disclosed in US 2009/0075968 (WO 2007/073934)
Example 42
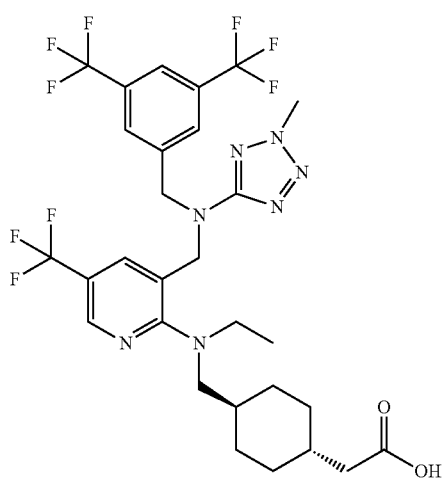 [SMILES: CCN(C[C@H]1CC[C@H](CC(=O)O)CC1)c1ncc(C(F)(F)F)cc1CN(Cc1cc(C(F)(F)F)cc(C(F)(F)F)c1)c1nnn(C)n1]
Example 43
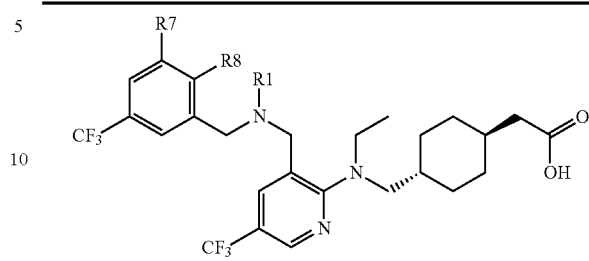
| No. | R7 | R8 | R1 |
|---|---|---|---|
| 43-1 | Cl | H | 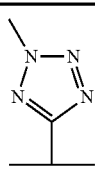 |
| 43-2 | NO2 | H | 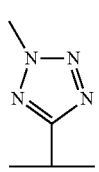 |
| 43-3 | CN | H | 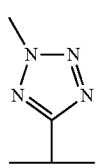 |
| 43-4 | Cl | F | 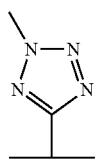 |
| 43-5 | CF3 | H | 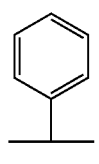 |
| 43-6 | Cl | H | 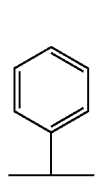 |

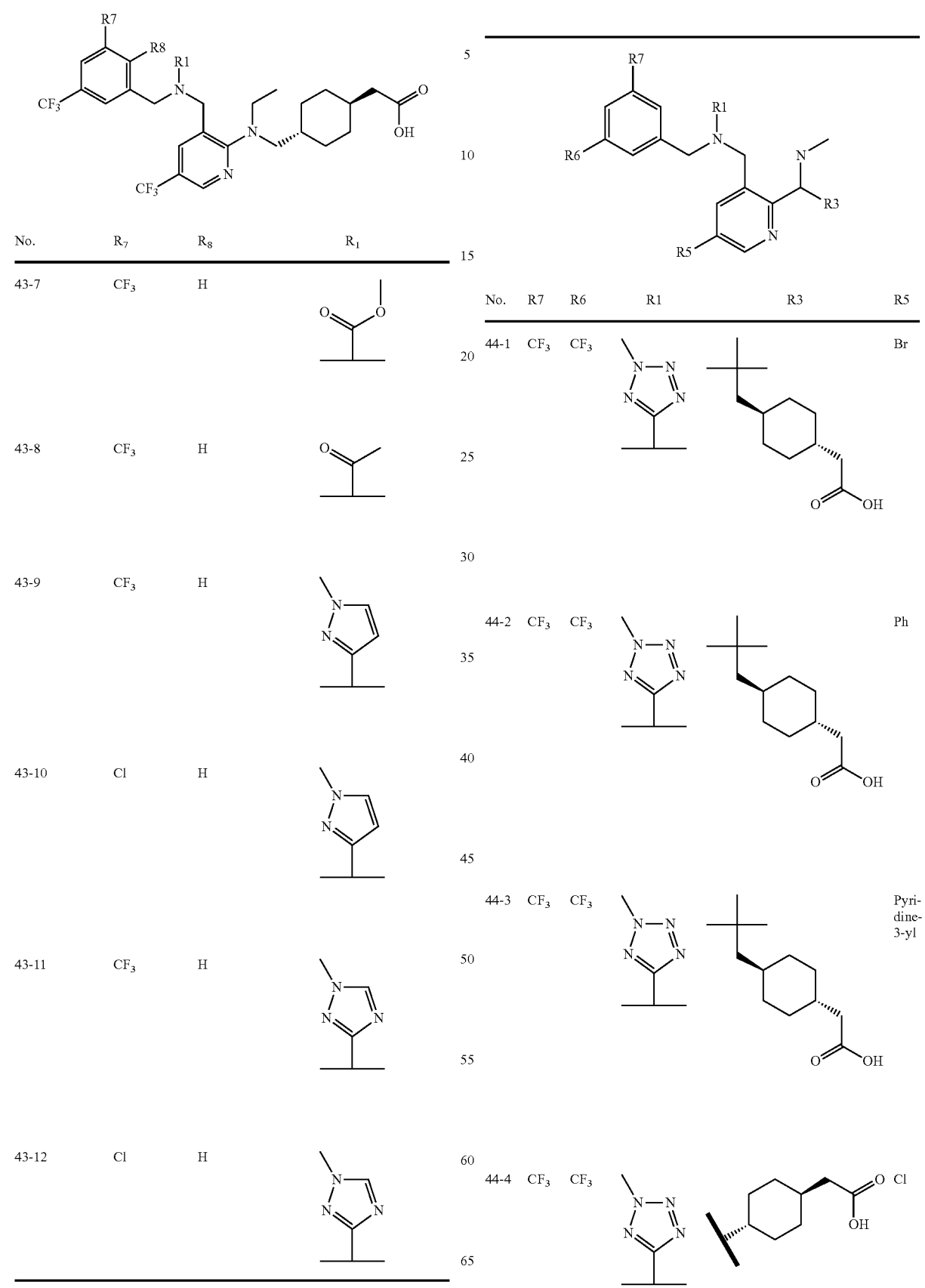

-continued
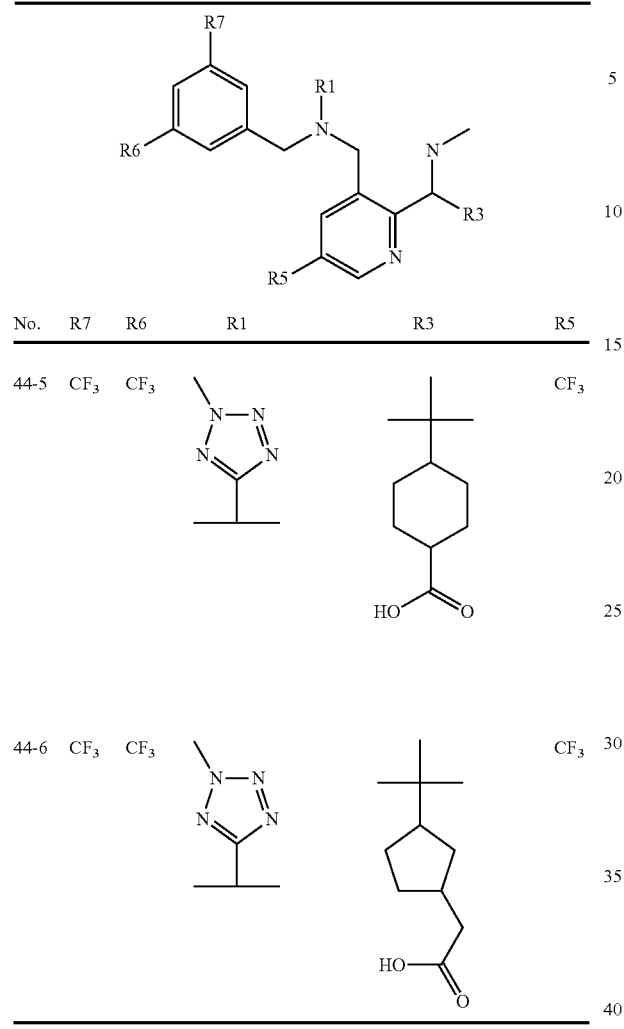
| No. | R7 | R6 | R1 | R3 | R5 |
|---|---|---|---|---|---|
| 44-5 | CF₃ | CF₃ | | | CF₃ |
| 44-6 | CF₃ | CF₃ | | | CF₃ |
Example 45
Example 46
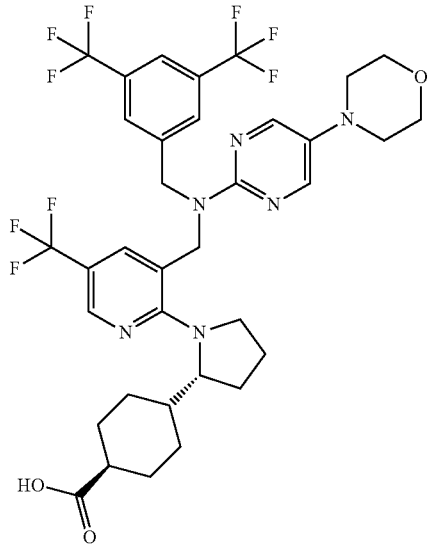
Example 47-52 are Compounds Disclosed in US 2009/0227580 (WO 2007/128568)
Example 47
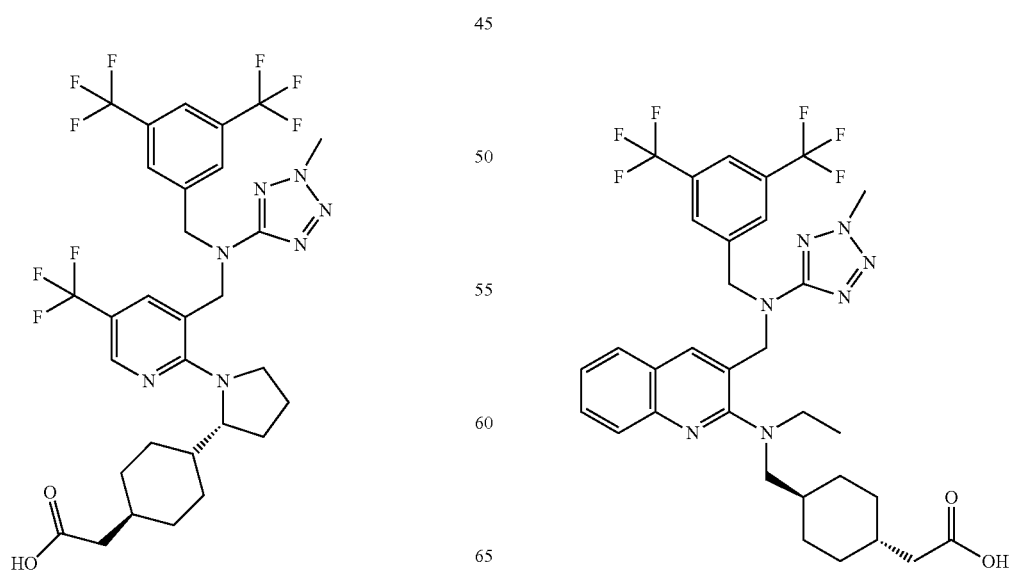

| 91 | 92 |
|---|---|
| Example 48 | Example 50 |
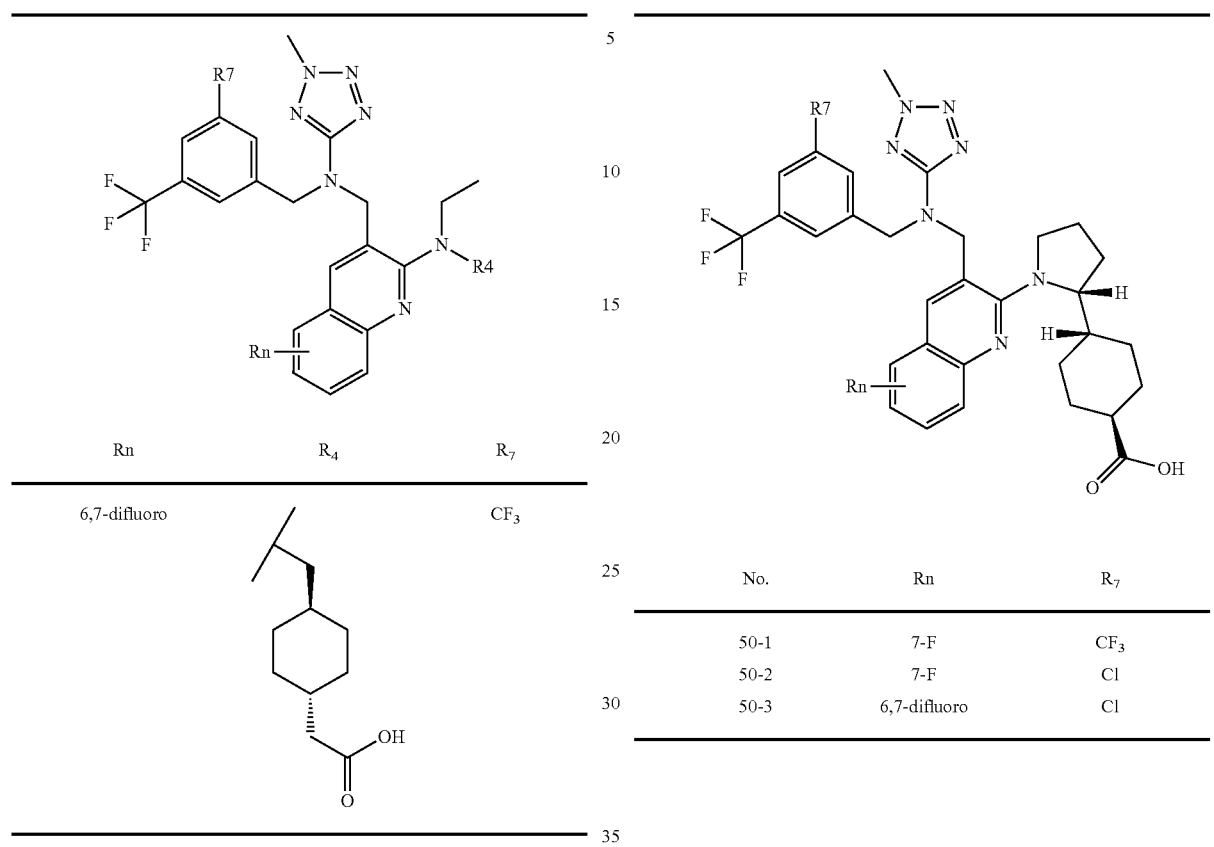
Example 49
| No. | Rn | R7 |
|---|---|---|
| 50-1 | 7-F | CF3 |
| 50-2 | 7-F | Cl |
| 50-3 | 6,7-difluoro | Cl |
Example 51
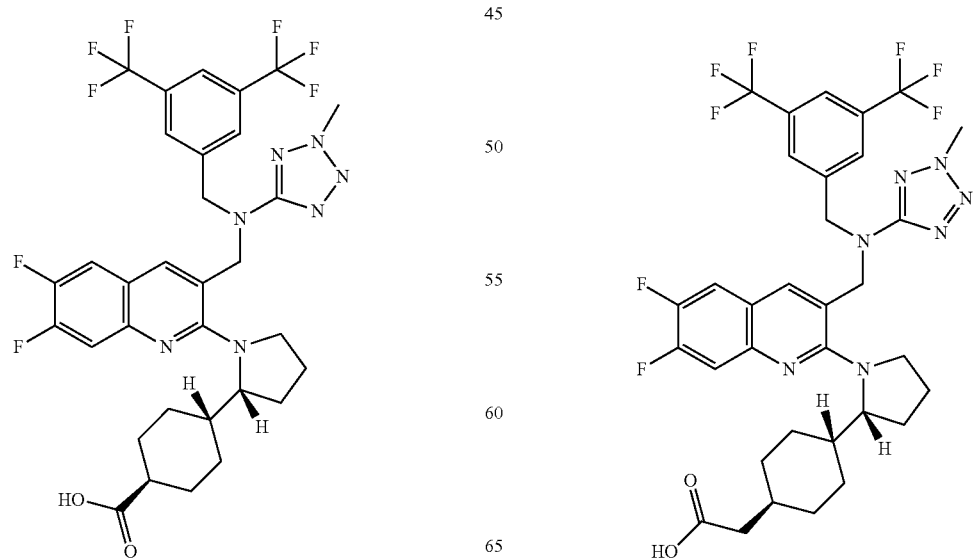

Example 52
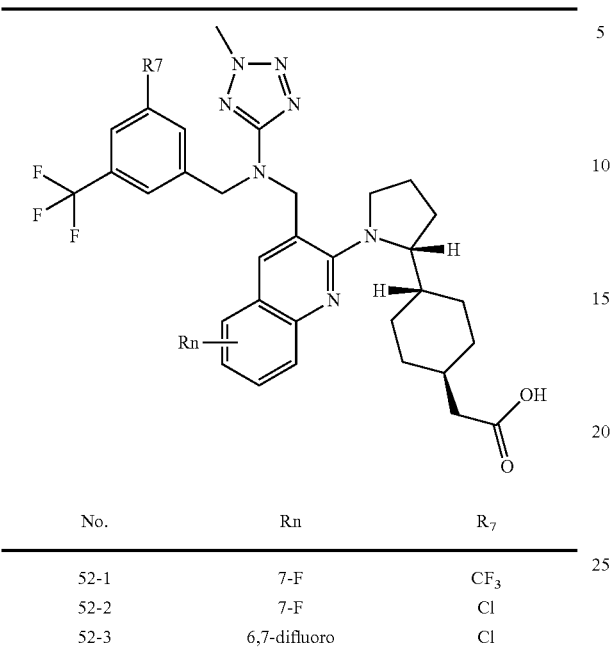
| No. | Rn | R7 |
|---|---|---|
| 52-1 | 7-F | CF3 |
| 52-2 | 7-F | Cl |
| 52-3 | 6,7-difluoro | Cl |
Example 54: Disclosed in WO 2007/081569 (US 2009/042892)
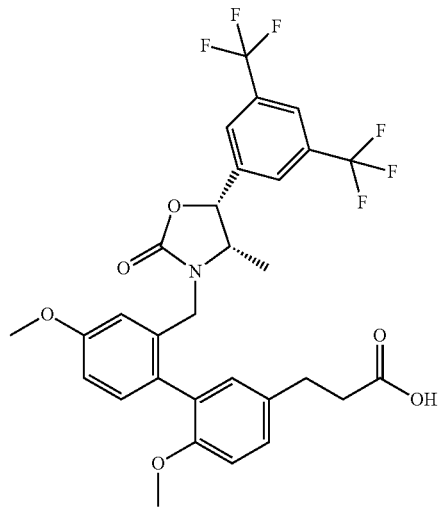
Example 53: Disclosed in WO 2006/002342 (US 2008/269284)
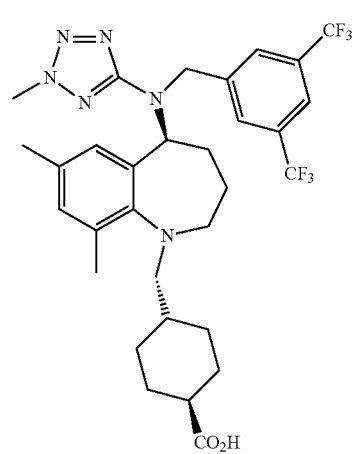
Example 55: Disclosed in WO 2007/081571 (US 2009/075979)—Example 64
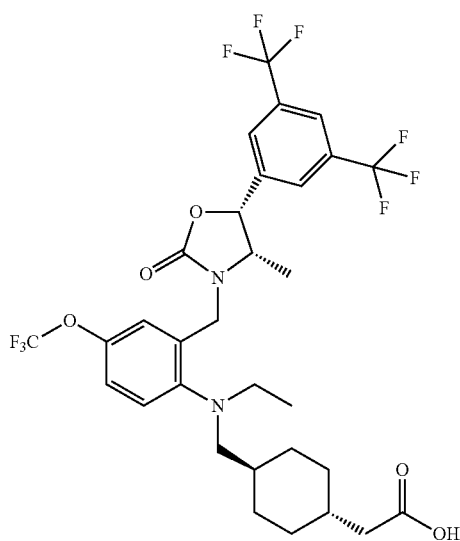 [SMILES: CCN(C[C@H]1CC[C@H](CC(=O)O)CC1)c1ccc(OC(F)(F)F)cc1CN1C(=O)O[C@H](c2cc(C(F)(F)F)cc(C(F)(F)F)c2)[C@@H]1C]

Example 56: Disclosed in US 2009/082352—Example 45

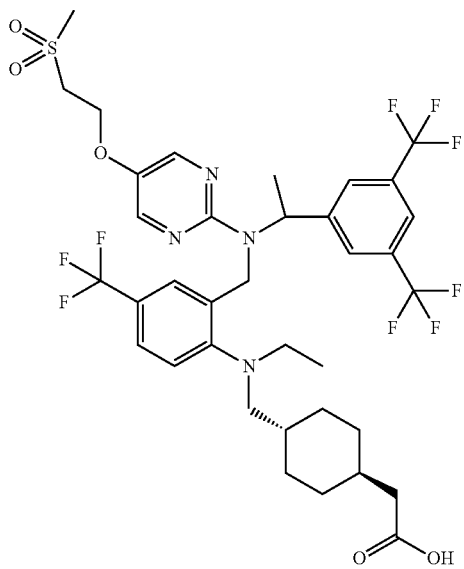 [SMILES: CCN(C[C@H]1CC[C@H](CC(=O)O)CC1)c1ccc(C(F)(F)F)cc1CN(c1ncc(OCCS(C)(=O)=O)cn1)C(C)c1cc(C(F)(F)F)cc(C(F)(F)F)c1]

Example 57

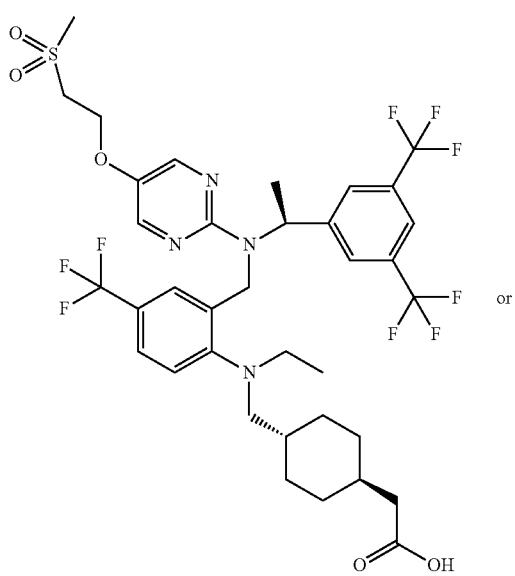

or

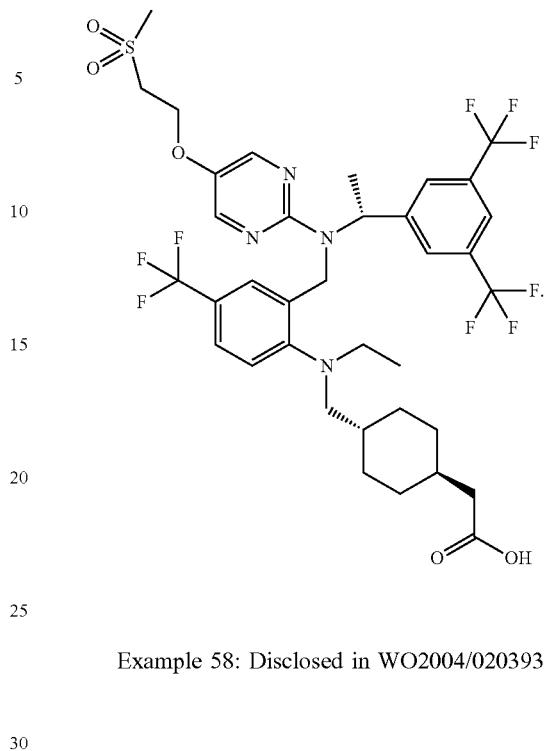

Example 58: Disclosed in WO2004/020393

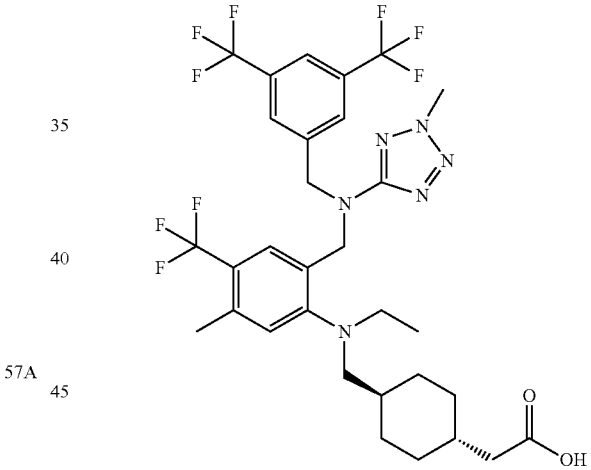

It can be seen that the compounds of the invention are useful as CETP inhibitors and useful in the treatment of diseases and conditions associated with CETP activity such as the diseases disclosed herein in a subject with high triglycerides level.

It will be understood that the invention has been described by way of example only and modifications may be made whilst remaining within the scope and spirit of the invention.

What is claimed is:

1. A method of treating or ameliorating atherosclerosis by raising HDL-C and/or lowering LDL-C, in a subject comprising, administering to the subject a therapeutically effective amount of the following compound:

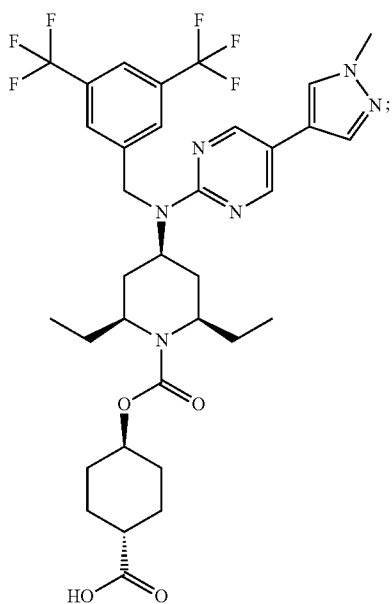

or a pharmaceutically acceptable salt thereof, wherein the subject's triglyceride level is a fasting triglyceride level greater than 500 mg/dL.

2. A method of treating atherosclerosis by raising HDL-C and/or lowering LDL-C comprising:
 a. selecting a subject with a fasting triglyceride level greater than 500 mg/dL; and
 b. administering to said subject a therapeutically effective amount of a compound of the formula:

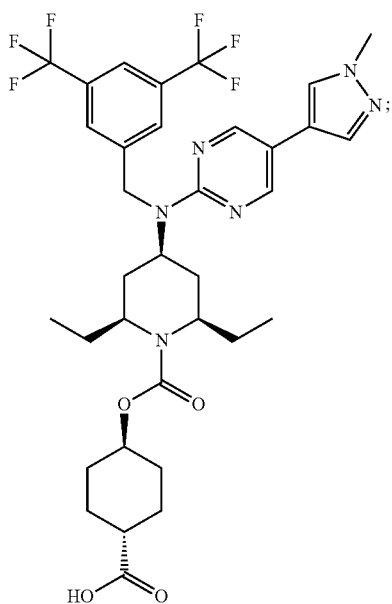

or a pharmaceutically acceptable salt thereof.

3. The method according to claim 1 or claim 2 further comprising administering at least one other therapeutic agent selected from: statin, cholesterol absorption inhibitor, apoA-I up-regulator/inducer, pre-beta HDL mimetic, ABCA1 stabilizer or inducer, LXR agonist, FXR agonist, phospholipid transfer protein (PLTP) inhibitor, aldosterone synthase inhibitor (ASI), fibric acid derivative, fish oil, DGAT1 inhibitor and endothelial lipase inhibitor, or a pharmaceutically acceptable salt thereof.

4. The method according to claim 1 wherein the compound maintains greater than or equal to 50% inhibition of CETP inhibitory activity in subjects with high plasma triglycerides when compared to subject with normal plasma triglycerides.

5. The method according to claim 2 wherein the compound maintains greater than or equal to 50% inhibition of CETP inhibitory activity in subjects with high plasma triglycerides when compared to subject with normal plasma triglycerides.

6. The method of claim 3, wherein the at least one other therapeutic agent is a statin or a pharmaceutically acceptable salt thereof.

7. The method of claim 3, wherein the at least one other therapeutic agent is a cholesterol absorption inhibitor or a pharmaceutically acceptable salt thereof.

8. The method of claim 3, wherein the at least one other therapeutic agent is a apoA-I up-regulator/inducer or a pharmaceutically acceptable salt thereof.

9. The method of claim 3, wherein the at least one other therapeutic agent is a pre-beta HDL mimetic or a pharmaceutically acceptable salt thereof.

10. The method of claim 3, wherein the at least one other therapeutic agent is a ABCA1 stabilizer or inducer or a pharmaceutically acceptable salt thereof.

11. The method of claim 3, wherein the at least one other therapeutic agent is a LXR agonist or a pharmaceutically acceptable salt thereof.

12. The method of claim 3, wherein the at least one other therapeutic agent is a FXR agonist or a pharmaceutically acceptable salt thereof.

* * * * *